United States Patent [19]

Vogel et al.

[11] Patent Number: 5,679,320

[45] Date of Patent: Oct. 21, 1997

[54] FIBRIN BINDING DOMAIN POLYPEPTIDES AND USES AND METHODS OF PRODUCING SAME

[75] Inventors: Tikva Vogel; Avigdor Levanon, both of Rehovot; Moshe M. Werber, Tel Aviv; Rachel Guy, Rehovot; Amos Panet, Jerusalem; Jacob Hartman, Holon; Hadassa Shaked, Ramat Gan, all of Israel

[73] Assignee: Bio-Technology General Corp., Iselin, N.J.

[21] Appl. No.: 259,569

[22] Filed: Jun. 14, 1994

Related U.S. Application Data

[63] Continuation of Ser. No. 703,842, May 21, 1991, abandoned, which is a continuation-in-part of Ser. No. 526,397, May 21, 1990, Pat. No. 5,270,030, which is a continuation-in-part of Ser. No. 345,952, Apr. 28, 1989, abandoned, which is a continuation-in-part of Ser. No. 291,951, Dec. 29, 1988, abandoned.

[30] Foreign Application Priority Data

Dec. 29, 1989 [CA] Canada ................................ 2006929

[51] Int. Cl.⁶ ...................................................... A61K 51/08
[52] U.S. Cl. .......................... 424/1.69; 424/9; 530/380; 530/381; 530/382; 514/2
[58] Field of Search ...................... 424/1.37, 9, 1.69; 530/300, 380, 381, 382; 514/2, 14

[56] References Cited

U.S. PATENT DOCUMENTS 4,663,146  5/1987  Morser et al. ............................ 424/1.1

FOREIGN PATENT DOCUMENTS 0207751  7/1987  European Pat. Off. .
8901942  9/1989  WIPO .

OTHER PUBLICATIONS

Uehara et al. J. Nucl. Med. 29 (1988) pp. 1264–1267.

*Primary Examiner*—Toni R. Scheiner
*Attorney, Agent, or Firm*—John P. White

[57] ABSTRACT

This invention provides an imaging agent which comprises a polypeptide labeled with an imageable marker, such polypeptide having an amino acid sequence substantially present in the fibrin binding domain of naturally-occurring human fibronectin and being capable of binding to fibrin. The invention further provides a method wherein the imaging agent is used for imagifig a fibrin-containing substance, i.e., a thrombus or atherosclerotic plaque. Further provided are plasmids for expression of polypeptides having an amino acid sequence substantially present in the fibrin binding domain of naturally-occurring human fibronectin and being capable of binding to fibrin, hosts containing these plasmids, methods of producing the polypeptides, methods of treatment using the polypeptides, and methods of recovering, refolding and reoxidizing the polypeptides. The invention also provides for purified polypeptides substantially free of other substances of human origin which have an amino acid sequence substantially present in the fibrin binding domain of naturally-occurring human fibronectin and which are capable of binding to fibrin.

13 Claims, 66 Drawing Sheets

FIG. 2A-1

FIRST SEQ. NO.=

```
    S   K   R   1Q   A   Q   Q   M   V   Q   P   Q   S   P   V
  AAG AGC AAG AGG CAG GCT CAG CAA ATG GTT CAG CCC CAG TCC CCG GTG         49
    1                   5                  10                  15

A   V   S   Q   S   K   P   G 2  C   Y   D   N   G   K   H   Y
  GCT GTC AGT CAA AGC AAG CCC GGT TGT TAT GAC AAT GGA AAA CAC TAT         97
                   20                  25                  30

Q   I   N   Q   Q   W   E   R   T   Y   L   G   N   V   L   V
  CAG ATA AAT CAA CAG TGG GAG CGG ACC TAC CTA GGT AAT GTG TTG GTT        145
                   35                  40                  45

C   T   C   Y   G   G   S   R   G   F   N   C   E   S   K   P
  TGT ACT TGT TAT GGA GGA AGC CGA GGT TTT AAC TGC GAA AGT AAA CCT        193
                   50                  55                  60

E   A   E   T  3C   F   D   K   Y   T   G   N   T   Y   R
  GAA GCT GAA GAG ACT TGC TTT GAC AAG TAC ACT GGG AAC ACT TAC CGA        241
                   65                  70                  75

V   G   D   T   Y   E   R   P   K   D   S   M   I   W   D   C
  GTG GGT GAC ACT TAT GAG CGT CCT AAA GAC TCC ATG ATC TGG GAC TGT        289
                   80                  85                  90                  95
```

FIG. 2A-2

```
    T   C   I   G   A   G   R   G   R   I   S   C   T   I   A   N
    ACC TGC ATC GGG GCT GGG CGA GGG AGA ATA AGC TGT ACC ATC GCA AAC    337
                        100             105             110

R   C   H   E   G   G   Q   S   Y   K   I   G   D   T   W   R
    CGC TGC CAT GAA GGG GGT CAG TCC TAC AAG ATT GGT GAC ACC TGG AGG    385
            115             120             125

R   P   H   E   T   G   G   Y   M   L   E   C   V   C   L   G
    AGA CCA CAT GAG ACT GGT GGT TAC ATG TTA GAG TGT GTG TGT CTT GGT    433
        130             135             140

N   G   K   G   E   W   T   C   K   P   I   A   E   K   C   F
    AAT GGA AAA GGA GAA TGG ACC TGC AAG CCC ATA GCT GAG AAG TGT TTT    481
    145             150             155

D   H   A   A   G   T   S   Y   V   V   G   E   T   W   E   K
    GAT CAT GCT GCT GGG ACT CCC TAT GTG GTC GGA GAA ACG TGG GAG AAG    529
    160             165             170             175
```

FIG. 2A-3

```
 P   Y   Q   G   W   M   M   V   D   C   T   C   L   G   E   G
CCC TAC CAA GGC TGG ATG ATG GTA GAT TGT ACT TGC CTG GGA GAA GGC    577
            180                 185                 190

S   G   R   I   T   C   T   S   R   N   R   C   N   D   Q   D
AGC GGA CGC ATC ACT TGC ACT TCT AGA AAT AGA TGC AAC GAT CAG GAC    625
            195          6      200                 205

T   R   T   S   Y   R   I   G   D   T   W   S   K   K   D   N
ACA AGG ACA TCC TAT AGA ATT TGA GAC ACC TGG AGC AAG AAG GAT AAT    673
            210                 215                 220

R   G   N   L   L   Q   C   I   C   T   G   N   G   R   G   E
CGA GGA AAC CTG CTC CAG TGC ATC TGC ACA GGC AAC GGC CGA GGA GAG    721
            225                 230                 235

W   K   C   E   R   H   T   S   V   Q   T   T   S   S   G   S
TGG AAG TGT GAG AGG CAC ACC TCT GTG CAG ACC ACA TCG AGC GGA TCT    769
            240     7          245                 250          255

G   P   F   T   D   V   R   A   A   V   Y   Q   P   Q   P   H
GGC CCC TTC ACC GAT GTT CGT GCA GCT GTT TAC CAA CCG CAG CCT CAC    817
            260                 265                 270
```

FIG. 2B-1

```
      P   Q   P   P   Y   G   H   C   V   T   D   S   G   V   V
      CCC CAG CCT CCT TAT GGC CAC TGT GTC ACA GAC AGT GGT GTG GTC   865
                      275             8 280                 285

Y   S   V   G   M   Q   W   L   K   T   Q   N   K   Q   M
      TAC TCT GTG GGG ATG CAG TGG TTG AAG ACA CAA AAT AAG CAA ATG   913
              290             295             300

L   C   T   C   L   G   N   G   V   S   C   Q   E   A   V
      CTT TGC ACG TGC CTG GGC AAC GGA GTC AGC TGC CAA GAG ACA GCT GTA   961
      305             310             315      9

T   Q   T   Y   G   G   N   L   N   G   E   P   C   V   L   P
      ACC CAG ACT TAC GGT GGC AAC TTA AAT GGA GAG CCA TGT GTC TTA CCA  1009
      320             325             330             335

F   T   Y   N   G   R   T   F   Y   S   C   T   T   E   G   R
      TTC ACC TAC AAT GGC AGG ACG TTC TAC TCC TGC ACC ACG GAA GGG CGA  1057
                      340             345             350
```

FIG. 2B-2

```
      Q   D   G   H   L   W   C   S   T   T   S   N   Y   E   Q   D
      CAG GAC GGA CAT CTT TGG TGC AGC ACA ACT TCG AAT TAT GAG CAG GAC    1105
                      355             360             365

10
      Q   K   Y   S   F   C   T   D   H   T   V   L   V   Q   T   Q
      CAG AAA TAC TCT TTC TGC ACA GAC CAC ACT GTT TTG GTT CAG ACT CAA    1153
                      370             375             380

G   G   N   S   N   G   A   L   C   H   F   P   F   R   R   N
      GGA GGA AAT TCC AAT GGT GCC TTG TGC CAC TTC CCC TTC CTA TAC AAC    1201
                      385             390             395

N   H   N   Y   T   D   C   T   S   E   G   R   R   D   N   M
      AAC CAC AAT TAC ACT GAT TGC ACT TCT GAG GGC AGA AGA GAC AAC ATG    1249
                      400             405             410             415

K   W   C   G   T   T   Q   N   Y   D   A   D   Q   K   F   G
      AAG TGG TGT GGG ACC ACA CAG AAC TAT GAT GCC GAC CAG AAG TTT GGG    1297
                      420             425             430

F   C   P   M   A   A   H   E   E   I   C   T   T   N   E   G
      TTC TGC CCC ATG GCT GCC CAC GAG GAA ATC TGC ACA ACC AAT GAA GGG    1345
                      435             440             445
```
11

FIG. 2B-3

```
V   M   Y   R   I   G   D   Q   W   D   K   Q   H   D   M   G
GTC ATG TAC CGC ATT GGA GAT CAG TGG GAT AAG CAG CAT GAC ATG GGT   1393
    450                 455                 460

H   M   M   R   C   T   C   V   G   N   G   R   G   E   W   T
CAC ATG ATG AGG TGC ACG TGT GTT GGG AAT GGT CGT GGG GAA TGG ACA   1441
465                 470                 475

12
C   I   A   Y   S   Q   L   R   D   Q   C   I   V   D   D   I
TGC ATT GCC TAC TCG CAA CTT CGA GAT CAG TGC ATT GTT GAT GAC ATC   1489
480                 485                 490                 495

T   Y   N   V   N   D   T   F   H   K   R   H   E   E   G   H
ACT TAC AAT GTG AAC GAC ACA TTC CAC AAG CGT CAT GAA GAG GGG CAC   1537
                500                 505                 510

M   L   N   C   T   C   F   G   Q   G   R   G   R   W   K   C
ATG CTG AAC TGT ACA TGC TTC GGT CAG CAG GGT CGG AGG TGG AAG TGT   1585
            515                 520                 525
```

FIG. 2B-4

```
     D   P   V   D   Q  ¹³C   Q   D   S   E   T   G   T   F   Y   Q
    GAT CCC GTC GAC CAA TGC CAG GAT TCA GAG ACT GGG ACG TTT TAT CAA   1633
            530             535             540

I   G   D   S   W   E   K   Y   V   H   G   V   R   Y   Q   C
    ATT GGA GAT TCA TGG GAG AAG TAT GTG CAT GGT GTC AGA TAC CAG TGC   1681
            545             550             555

Y   C   Y   G   R   G   I   G   E   W   H   C   Q   P   L   Q
    TAC TGC TAT GGC CGT GGC ATT GGG GAG TGG CAT TGC CAA CCT TTA CAG   1729
            560             565             570             575

T   Y   P   S  ¹⁴S   G   P   V   E   V   F   I   T   E   T
    ACC TAT CCA AGC TCA GGT CCT GTC GAA GTA TTT ATC ACT GAG ACT       1777
            580             585             590

P   S   Q   P   N   S   H   P   I   Q   W   N   A   P   Q   P
    CCG AGT CAG CCC AAC TCC CAC CCC ATC CAG TGG AAT GCA CCA CAG CCA   1825
            595             600             605

S   H   I   S   K   Y   I   L   R   W   R   P   K   N   S   V
    TCT CAC ATT TCC AAG TAC ATT CTC AGG TGG AGA CCT AAA AAT TCT GTA   1873
            610             615             620
```

FIG. 2C-1

```
    G   R   W   K   E   A   T   I   P   G   H   L   N   S   Y   T
    GGC CGT TGG AAG GAA GCT ACC ATA CCA GGC CAC TTA AAC TCC TAC ACC     1921
                625             630             635
    I   K   G   L   K   P   G   V   V   Y   E   G   Q   L   I   S
    ATC AAA GGC CTG AAG CCT GGT GTG GTA TAC GAG GGC CAG CTC ATC AGC     1969
    640             645             650             655
    I   Q   Q   Y   G   H   Q   E   V   T   R   F   D   F   T   T
    ATC CAG CAG TAC GGC CAC CAA GAA GTG ACT CGC TTT GAC TTC ACC ACC     2017
                660             665             670
       15  S   T   S   T   P   V   T   S   N   T   V   T   G   E   T
    T  ACC AGC ACC AGC ACA CCT GTG ACC AGC AAC ACC GTG ACA GGA GAG ACG  2065
            675             680             685
       16
    T  P   F  S   P   L   V   A   T   S   E   S   V   T   E   I
    ACT CCC TTT TCT CCT CTT GTG GCC ACT TCT GAA TCT GTG ACC GAA ATC     2113
            690             695             700
```

FIG. 2C-2

```
T   A   S   S   F   V   V   S   W   V   S   A   S   D   T   V
ACA GCC AGT AGC TTT GTG GTC TCC TGG GTC TCA GCT TCC GAC ACC GTG    2161
705                     710                 715

S   G   F   R   V   E   Y   E   L   S   E   E   G   D   E   P
TCG GGA TTC CGG GTG GAA TAT GAG CTG AGT GAG GAG GGA GAT GAG CCA    2209
720                     725                 730                 735

Q   Y   L   D   L   P   S   T   A   T   S   V   N   I   P   D
CAG TAC CTG GAT CTT CCA AGC ACA GCC ACT TCT GTG AAC ATC CCT GAC    2257
                740                 745                 750

L   L   P   G   R   K   Y   I   V   N   V   Y   Q   I   S   E
CTG CTT CCT GGC CGA AAA TAC ATT GTA AAT GTC TAT CAG ATA TCT GAG    2305
        755                 760                 765

D   G   E   Q   S   L   I   L   S   T   S   Q   T   A   P
GAT GGG GAG CAG AGT TTG ATC CTG TCT ACT TCA CAA ACA ACA GCG CCT    2353
                770                 775                 780

D   A   P   P   D   P   T   V   D   Q   V   D   D   T   S   I
GAT GCC CCT CCT GAC CCG ACT GTG GAC CAA GTT GAC GAT ACC TCA ATT    2401
785                     790                 795
```

FIG. 2C-3

```
    V   V   R   W   S   R   P   Q   A   P   I   T   G   Y   R   I
    GTT GTT CGC TGG AGC AGA CCC CAG GCT CCC ATC ACA GGG TAC AGA ATA   2449
    800             805             810             815

V   Y   S   P   S   V   E   G   S   S   T   E   L   N   L   P
    GTC TAT TCG CCA TCA GTA GAA GGT AGC AGC ACA GAA CTC AAC CTT CCT   2497
                    820             825             830

E   T   A   N   S   V   T   L   S   D   L   Q   P   G   V   Q
    GAA ACT GCA AAC TCC GTC ACC CTC AGT GAC TTG CAA CCT GGT GTT CAG   2545
            835             840             845

Y   N   I   T   I   Y   A   V   E   E   N   Q   E   S   T   P
    TAT AAC ATC ACT ATC TAT GCT GTG GAA GAA AAT CAA GAA AGT ACA CCT   2593
    850             855             860

18
    V   V   I   Q   Q   E   T   T   G   T   P   R   S   D   T   V
    GTT GTC ATT CAA CAA GAA ACC ACT GGC ACC CCA CGC TCA GAT ACA GTG   2641
            865             870             875
```

FIG. 2D-1

```
  P   S   P   R   D   L   Q   F   V   E   V   T   D   V   K   V
CCC TCT CCC AGG GAC CTG CAG TTT GTG GAA GTG ACA GAC GTG AAG GTC    2689
880             885             890             895

T   I   M   W   T   P   P   E   S   A   V   T   G   Y   R   V
ACC ATC ATG TGG ACA CCG CCT GAG AGT GCA GTG ACC GGC TAC CGT GTG    2737
        900             905             910

D   V   I   P   V   N   L   P   G   E   H   G   Q   R   L   P
GAT GTG ATC CCC GTC AAC CTG CCT GGC GAG CAC GGG CAG AGG CTG CCC    2785
            915             920             925

I   S   R   N   T   F   A   E   V   T   G   L   S   P   G   V
ATC AGC AGG AAC ACC TTT GCA GAA GTC ACC GGG CTG TCC CCT GGG GTC    2833
        930             935             940

T   Y   Y   F   K   V   F   A   V   S   H   G   R   E   S   K
ACC TAT TAC TTC AAA GTC TTT GCA GTG AGC CAT GGG AGG GAG AGC AAG    2881
        945             950             955

P   L   T   A   Q   Q   T   ¹⁹K   L   D   A   P   T   N   L
CCT CTG ACT GCT CAA CAG ACA ACC AAA CTG GAT GCT CCC ACT AAC CTC    2929
960             965             970             975
```

FIG. 2D-2

```
Q   F   V   N   E   T   D   S   T   V   L   R   W   T   P
CAG TTT GTC AAT GAA ACT GAT TCT ACT GTC CTG AGA TGG ACT CCA    2977
            980                 985                 990

P   R   A   Q   I   T   G   Y   R   L   T   V   G   L   T   R
CCT CGG GCC CAG ATA ACA GGA TAC CGA CTG ACC GTG GGC CTT ACC CGA    3025
            995                 1000                1005

R   G   Q   P   R   Q   Y   N   V   G   P   S   V   S   K   Y
AGA GGC CAG CCC AGG CAG TAC AAT GTG GGT CCC TCT GTC TTC AAG TAC    3073
            1010                1015                1020

P   L   R   N   L   Q   P   A   S   E   Y   T   V   S   L   V
CCC CTG AGG AAT CTG CAG CCT GCA TCT GAG TAC ACC GTA TCC CTC GTG    3121
            1025                1030                1035

A   I   K   G   N   Q   E   S   P   K   A   T   G   V   F   T
GCC ATA AAG GGC AAC CAA GAG AGC CCC AAA GCC ACT GGA GTC TTT ACC    3169
            1040                1045                1050                1055
```

FIG. 2D-3

```
      20
 T   L   Q   P   G   S   S   I   P   P   Y   N   T   E   V   T
ACA CTG CAG CCT GGG AGC TCT ATT CCA CCT TAC AAC ACC GAG GTG ACT    3217
                1060            1065            1070

E   T   T   I   V   I   T   W   T   P   A   P   R   I   G   F
GAG ACC ACC ATC GTG ATC ACA TGG ACG CCT GCT CCA AGA ATT GGT TTT    3265
            1075            1080            1085

K   L   G   V   R   P   S   Q   Q   G   G   E   A   P   R   E   V
AAG CTG GGT GTA CGA CCA AGC CAG CAG GGA GGA GAG GCA CCA CGA GAA GTG  3313
        1090            1095            1100

T   S   D   S   G   S   I   V   V   S   G   L   T   P   G   V
ACT TCA GAC TCA GGA AGC ATC GTT GTG TCC GGC TTG ACT CCA GGA GTA    3361
        1105            1110            1115

E   Y   V   Y   T   I   Q   V   L   R   D   G   Q   E   R   D
GAA TAC GTC TAC ACC ATC CAA GTC CTG AGA GAT GGA CAG GAA AGA GAT    3409
        1120            1125            1130        1135

21
 A   P   I   V   N   K   V   V   T   P   L   S   P   P   T   N
GCG CCA ATT GTA AAC AAA GTG GTG ACA CCA TTG TCT CCA CCA ACA AAC    3457
        1140            1145            1150
```

FIG. 2D-4

```
     L   H   L   E   A   N   P   D   T   G   V   L   T   V   S   W
     TTG CAT CTG GAG GCA AAC CCT GAC ACT GGA GTG CTC ACA GTC TCC TGG    3505
                     1155                1160                1165

E   R   S   T   T   P   D   I   T   G   Y   R   I   T   T   T
     GAG AGG AGC ACC ACC CCA GAC ATT ACT GGT TAT AGA ATT ACC ACA ACC    3553
                     1170                1175                1180

P   T   N   G   Q   Q   N   S   L   E   E   V   H   A
     CCT ACA AAC GGC CAG CAG GGA AAT TCT TTG GAA GAA GTG GTC CAT GCT    3601
                     1185                1190                1195

D   Q   S   S   C   T   F   D   N   L   S   P   G   L   E   Y
     GAT CAG AGC TCC TGC ACT TTT GAT AAC CTG AGT CCC GGC CTG GAG TAC    3649
             1200                1205                1210        1215

N   V   S   V   Y   T   V   K   D   K   E   S   V   P   I
     AAT GTC AGT GTT TAC ACT GTC AAG GAC AAG GAA AGT GTC CCT ATC        3697
                     1220                1225                1230
```

FIG. 2E-1

```
  S   D   T   I   I   P  22A   V   P   P   P   T   D   L   R   F
TCT GAT ACC ATC ATC CCA GCT GTT CCT CCT CCC ACT GAC CTG CGA TTC    3745
                    1235                    1240                1245

T   N   I   G   P   D   T   M   R   V   T   W   A   P   P   P
ACC AAC ATT GGT CCA GAC ACC ATG CGT GTC ACC TGG GCT CCA CCC CCA    3793
                    1250                    1255                1260

S   I   D   L   T   N   F   L   V   R   Y   S   P   V   K   N
TCC ATT GAT TTA ACC AAC TTC CTG GTG CGT TAC TCA CCT GTG AAA AAT    3841
                    1265                    1270                1275

E   E   D   V   A   E   L   S   I   S   P   S   D   N   A   V
GAG GAA GAT GTT GCA GAG TTG TCA ATT TCT CCT TCA GAC AAT GCA GTG    3889
                    1280                    1285                1290    1295

V   L   T   N   L   L   P   G   T   E   Y   V   V   S
GTC TTA ACA AAT CTC CTG CCT GGT ACA GAA TAT GTA GTG AGT GTC TCC    3937
                    1300                    1305                1310

S   V   Y   E   Q   H   E   S   T   P   L   R   G   R   Q   K
AGT GTC TAC GAA CAA CAT GAG AGC ACA CCT CTT AGA GGA AGA CAG AAA    3985
                    1315                    1320                1325
```

FIG. 2E-2

```
   23 G   L   D   S   P   T   G   I   D   F   S   D   I   T   A
    T
    ACA GGT CTT GAT TCC CCA ACT GGC ATT GAC TTT TCT GAT ATT ACT GCC   4033
                            1330                1335                1340

N   S   F   T   V   H   W   I   A   P   R   A   T   I   T   G
    AAC TCT TTT ACT GTG CAC TGG ATT GCT CCT CGA GCC ACC ATC ACT GGC   4081
                            1345                1350                1355

Y   R   I   R   H   H   P   E   H   F   S   G   R   P   R   E
    TAC AGG ATC CGC CAT CAT CCC GAG CAC TTC AGT GGG AGA CCT CGA GAA   4129
                            1360                1365                1370          1375

D   R   V   P   H   S   R   N   S   I   T   L   T   N   L   T
    GAT CGG GTG CCC CAC TCT CGG AAT TCC ATC ACC CTC ACC AAC CTC ACT   4177
                            1375                1380                1385          1390

P   G   T   E   Y   V   V   S   I   V   A   L   N   G   R   E
    CCA GGC ACA GAG TAT GTG GTC AGC ATC GTT GCT CTT AAT GGC AGA GAG   4225
                            1395                1400                1405
```

FIG. 2E-3

```
  E   S   P   L   L   I   G   Q   Q   S   T²⁴ V   S   D   V   P
GAA AGT CCC TTA TTG ATT GGC CAA CAA TCA ACA GTT TCT GAT GTT CCG   4273
        1410            1415            1420

R   D   L   E   V   V   A   A   T   P   T   S   L   L   I   S
AGG GAC CTG GAA GTT GTT GCT GCG ACC CCC AGC CTA CTG ATC AGC       4321
        1425            1430            1435

W   D   A   P   A   V   T   V   R   Y   Y   R   I   T   Y   G
TGG GAT GCT CCT GCT GTC ACA GTG AGA TAT TAC AGG ATC ACT TAC GGA   4369
        1440            1445            1450            1455

E   T   G   G   N   S   P   V   Q   E   F   T   V   P   G   S
GAA ACA GGA GGA AAT AGC CCT GTC CAG GAG TTC ACT GTG CCT GGG AGC   4417
        1460            1465            1470

K   S   T   A   T   I   S   G   L   K   P   G   V   D   Y   T
AAG TCT ACA GCT ACC ATC AGC GGC CTT AAA CCT GGA GTT GAT TAT ACC   4465
        1475            1480            1485

I   T   V   Y   A   V   T   G   R   G   D   S   P   A   S   S
ATC ACT GTG TAT GCT GTC ACT GGC CGT GGA GAC AGC CCC GCA AGC AGC   4513
        1490            1495            1500
```

FIG. 2E-4

```
  K   P   I   S   I   N   Y   R   T²⁵ E   I   D   K   P   S   Q
AAG CCA ATT TCC ATT AAT TAC CGA ACA GAA ATT GAC AAA CCA TCC CAG    4561
                1505                    1510                1515

M   Q   V   T   D   V   Q   D   N   S   I   S   V   K   W   L
ATG CAA GTG ACC GAT GTT CAG GAC AAC AGC ATT AGT GTC AAG TGG CTG    4609
        1520                    1525                    1530                1535

P   S   S   P   V   T   G   Y   R   V   T   T   T   P   K
CCT TCA AGT TCC CCT GTT ACT GGT TAC AGA GTA ACC ACT CCC AAA        4657
                1540                    1545                    1550

N   G   P   G   P   T   K   T   K   T   A   G   P   D   Q   T
AAT GGA CCA GGA CCA ACA AAA ACT AAA ACT GCA GGT CCA GAT CAA ACA    4705
        1555                    1560                    1565

E   M   T   I   E   G   L   Q   P   T   V   E   Y   V   V   S
GAA ATG ACT ATT GAA GGC TTG CAG CCC ACA GTG GAG TAT GTG GTT AGT    4753
        1570                    1575                    1580
```

FIG. 2F-1

```
V   Y   A   Q   N   P   S   G   E   S   Q   P   L   V   Q   T
GTC TAT GCT CAG AAT CCA AGC GGA GAG AGT CAG CCT CTG GTT CAG ACT   4801
            1585            1590            1595

26
A   V   T   N   I   D   R   P   K   G   L   A   F   T   D   V
GCA GTA ACC AAC ATT GAT CGC CCT AAA GGA CTG GCA TTC ACT GAT GTG   4849
            1600            1605            1610            1615

D   V   D   S   I   K   I   A   W   E   S   P   Q   G   Q   V
GAT GTC GAT TCC ATC AAA ATT GCT TGG GAA AGC CCA CAG GGG CAA GTT   4897
            1620            1625            1630

S   R   Y   R   V   T   Y   S   S   P   E   D   G   I   H   E
TCC AGG TAC AGG GTG ACC TAC TCG AGC CCT GAG GAT GGA ATC CAT GAG   4945
            1635            1640            1645

L   F   P   A   P   D   G   E   E   D   T   A   E   L   Q   G
CTA TTC CCT GCA CCT GAT GGT GAA GAA GAC ACT GCA GAG CTG CAA GGC   4993
            1650            1655            1660

L   R   P   G   S   E   Y   T   V   S   V   V   A   L   H   D
CTC AGA CCG GGT TCT GAG TAC ACA GTC AGT GTG GTT GCC TTG CAC GAT   5041
            1665            1670            1675
```

FIG. 2F-2

```
    D   M   E   S   Q   P   L   I   G   T   Q   S   T²⁷  A   I   P
    GAT ATG GAG AGC CAG CCC CTG ATT GGA ACC CAG TCC ACA GCT ATT CCT    5089
    1680                    1685                1690                1695

A   P   T   D   L   K   F   T   Q   V   T   P   T   S   L   S
    GCA CCA ACT GAC CTG AAG TTC ACT CAG GTC ACA CCC ACA AGC CTG AGC    5137
                1700                1705                1710

A   Q   W   T   P   P   N   V   Q   L   T   G   Y   R   V   R
    GCC CAG TGG ACA CCA CCC AAT GTT CAG CTC ACT GGA TAT CGA GTG CGG    5185
            1715                1720                1725

V   T   P   K   E   K   T   G   P   M   K   E   I   N   L   A
    GTG ACC CCC AAG GAG AAG ACC GGA CCA ATG AAA GAA ATC AAC CTT GCT    5233
        1730                1735                1740

P   D   S   S   S   V   V   V   S   G   L   M   V   A   T   K
    CCT GAC AGC TCA TCC GTG GTT GTA TCA GGA CTT ATG GTG GCC ACC AAA    5281
    1745                1750                1755
```

FIG. 2F-3

```
  Y   E   V   S   V   Y   A   L   K   D   T   L   T   S   R   P
  TAT GAA GTG AGT GTC TAT GCT CTT AAG GAC ACT TTG ACA AGC AGA CCA
  1760            1765            1770            1775
                                                                        5329

28
  A   Q   G   V   V   T   T   L   E   N   V   S   P   P   R   R
  GCT CAG GGT GTT GTC ACC ACT CTG GAG AAT GTC AGC CCA CCA AGA AGG
  1780            1785            1790
                                                                        5377

A   R   V   T   D   A   T   E   T   T   I   T   I   S   W   R
  GCT CGT GTG ACA GAT GCT ACT GAG ACC ACC ATC ACC ATT AGC TGG AGA
  1795            1800            1805
                                                                        5425

T   K   T   E   T   I   T   G   F   Q   V   D   A   V   P   A
  ACC AAG ACT GAG ACG ATC ACT GGC TTC CAA GTT GAT GCC GTT CCA GCC
          1810            1815            1820
                                                                        5473

N   G   Q   T   P   I   Q   R   T   I   K   P   D   V   R   S
  AAT GGC CAG ACT CCA ATC CAG AGA ACC ATC AAG CCA GAT GTC AGA AGC
          1825            1830            1835
                                                                        5521

Y   T   I   T   G   L   Q   P   G   T   D   Y   K   I   Y   L
  TAC ACC ATC ACA GGT TTA CAA CCA GGC ACT GAC TAC AAG ATC TAC CTG
  1840            1845            1850            1855
                                                                        5569
```

FIG. 2G-1

```
      Y   T   L   N   D   N   A   R   S   S   P   V   V   I   D   A
      TAC ACC TTG AAT GAC AAT GCT CGG AGC TCC CCT GTG GTC ATC GAC GCC    5617
                              1860            1865            1870

S  29A   I   D   A   P   S   N   L   R   F   L   A   T   T
      TCC ACT GCC ATT GAT GCA CCA TCC AAC CTG CGT TTC CTG GCC ACC ACA    5665
                      1875            1880            1885

P   N   S   L   L   V   S   W   Q   P   P   R   A   R   I   T
      CCC AAT TCC TTG CTG GTA TCA TGG CAG CCA CCG GCC AGG ATT ACC        5713
                      1890            1895            1900

G   Y   I   I   K   Y   E   K   P   G   S   P   P   R   E   V
      GGC TAC ATC ATC AAG TAT GAG AAG CCT GGG TCT CCT CCC AGA GAA GTG    5761
              1905            1910            1915

V   P   R   P   R   P   G   V   T   E   A   T   I   T   G   L
      GTC CCT CGG CCC CGC CCT GGT GTC ACA GAG GCT ACT ATT ACT GGC CTG    5809
      1920            1925            1930            1935
```

FIG. 2G-2

```
  E   P   G   T   E   Y   T   I   Y   V   I   A   L   K   N   N
GAA CCG GGA ACC GAA TAT ACA ATT TAT GTC ATT GCC CTG AAG AAT AAT    5857
                1940            1945            1950

Q   K   S   E   P   L   I   G   R   K   K   T³⁰ D   E   L   P
CAG AAG AGC GAG CCC CTG ATT GGA AGG AAA AAG ACA GAC GAG CTT CCC    5905
                1955            1960            1965

Q   L   V   T   L   P   H   P   N   L   H   G   P   E   I   L
CAA CTG GTA ACC CTT CCA CAC CCC AAT CTT CAT GGA CCA GAG ATC TTG    5953
                1970            1975            1980

D   V   P   S   T   V   Q   K   T   P   F   V   T   H   P   G
GAT GTT CCT TCC ACA GTT CAA AAG ACC CCT TTC GTC ACC CAC CCT GGG    6001
                1985            1990            1995

Y   D   T   G   N   G   I   Q   L   P   G   T   S   G   Q   Q
TAT GAC ACT GGA AAT GGT ATT CAG CTT CCT GGC ACT TCT GGT CAG CAA    6049
                2000            2005            2010            2015

P   S   V   G   Q   Q   M   I   F   E   E   H   G   F   R   R
CCC AGT GTT GGG CAA CAA ATG ATC TTT GAG GAA CAT GGT TTT AGG CGG    6097
                2020            2025            2030
```

FIG. 2G-3

```
  T   T   P   P   T   T   A   T   P   I   R   H   P   R   P
ACC ACA CCG CCC ACA ACG GCC ACC CCC ATA AGG CAT AGG CCA AGA CCA
            2035            2040            2045                  6145

Y   P   P   N   V³¹ G   Q   E   A   L   S   Q   T   T   I   S
TAC CCG CCG AAT GTA GGA CAA GAA GCT CTC TCT CAG ACA ACC ATC TCA
            2050            2055            2060                  6193

W   A   P   F   Q   D   T   S   E   Y   I   I   S   C   H   P
TGG GCC CCA TTC CAG GAC ACT TCT GAG TAC ATC ATT TCA TGT CAT CCT
            2065            2070            2075                  6241

V   G   T   D   E   E   P   L   Q   F   R   V   P   G   T   S
GTT GGC ACT GAT GAA GAA CCC TTA CAG TTC AGG GTT CCT GGA ACT TCT
            2080            2085            2090            2095  6289

T   S   A   T   L   T   G   L   R   G   A   T   Y   N   I
ACC AGT GCC ACT CTG ACA GGC CTC ACC AGA GGT GCC ACC TAC AAC ATC
            2100            2105            2110                  6337
```

FIG. 2G-4

```
      I   V   E   A   L   K   D   Q   Q   R   H   K³²  V   R   E   E
     ATA GTG GAG GCA CTG AAA GAC CAG CAG AGG CAT AAG GTT CGG GAA GAG         6385
                         2115                2120                2125

V   V   T   V   G   N   S   V   N   E   G   L   N   Q   P   T
     GTT GTT ACC GTG GGC AAC TCT GTC AAC GAA GGC TTG AAC CAA CCT ACG         6433
                2130                2135                2140

D   D   S³³ C   F   D   P   Y   T   V   S   H   Y   A   V   G
     GAT GAC TCG TGC TTT GAC CCC TAC ACA GTT TCC CAT TAT GCC GTT GGA         6481
                         2145                2150                2155

D   E   W   E   R   M   S   E   S   G   F   K   L   L   C   Q
     GAT GAG TGG GAA CGA ATG TCT GAA TCA GGC TTT AAA CTG TTG TGC CAG         6529
                2160                2165                2170        2175

C   L   G   F   G   S   G   H   F   R   C   D   S   S   R³⁴ W
     TGC TTA GGC TTT GGA AGT GGT CAT TTC AGA TGT GAT TCA TCT AGA TGG         6577
                         2180                2185                2190

C   H   D   N   G   V   N   Y   K   I   G   E   K   W   D   R
     TGC CAT GAC AAT GGT GTG AAC TAC AAG ATT GGA GAG AAG TGG GAC CGT         6625
                2195                2200                2205
```

FIG. 2H-1

```
  Q   G   E   N   G   Q   M   M   S   C   T   C   L   G   N   G
CAG GGA GAA AAT GGC CAG ATG ATG AGC TGC ACA TGT CTT GGG AAC GGA      6673
                    2210                2215                2220

K   G   E   F   K   C   D   P   H   E   A   T³⁵ C   Y   D   D
AAA GGA GAA TTC AAG TGT GAC CCT CAT GAG GCA ACG TGT TAC GAT GAT      6721
                2225                2230                2235

G   K   T   Y   H   V   G   E   Q   W   Q   K   E   Y   L   G
GGG AAG ACA TAC CAC GTA GGA GAA CAG TGG CAG AAG GAA TAT CTC GGT      6769
                2240                2245                2250        2255

A   I   C   S   C   T   C   F   G   Q   R   G   W   R   C
GCC ATT TGC TCC TGC ACA TGC TTT GGA GGC CAG CGG GGC TGG CGC TGT      6817
                2260                2265                2270

D   N   C   R   R   P   G³⁶ G   E   P   S   P   E   G   T   T
GAC AAC TGC CGC AGA CCT GGG GGT GAA CCC AGT CCC GAA GGC ACT ACT      6865
                2275                2280                2285
```

FIG. 2H-2

```
    G   Q   S   Y   N   Q   Y   S   Q   R   Y   H   Q   R   T   N
    GGC CAG TCC TAC AAC CAG TAT TCT CAG AGA TAC CAT CAG AGA ACA AAC    6913
            2290            2295            2300

T   N   V   N   C   P   I   E   C   F   M   P   L   D   V   Q
    ACT AAT GTT AAT TGC CCA ATT GAG TGC TTC ATG CCT TTA GAT GTA CAG    6961
            2305            2310            2315

A   D   R   E   D   S   R   E   *
    GCT GAC AGA GAA GAT TCC CGA GAG TAA ATC ATC TTT CCA ATC CAG AGG    7009
            2320            2325            2330            2335

AAC AAG CAT GTC TCT CTG CCA AGA TCC ATC TAA ACT GGA GTG ATG TTA    7057
            2340            2345            2350

GCA GAC CCA GCT TAG AGT TCT TCT TTC TTT CTT AAG CCC TTT GCT CTG    7105
            2355            2360            2365

GAG GAA GTT CTC CAG CTT CAG CTC AAC TCA CAG CTT CTC CAA GCA TCA    7153
            2370            2375            2380
```

FIG. 2H-3

```
CCC TGG GAG TTT CCT GAG GGT TTT CTC ATA AAT GAG GGC TGC ACA TTG    7201
2385                2390                2395
CCT GTT CTG CTT CGA AGT ATT CAA TAC CGC TCA GTA TTT TAA ATG AAG    7249
2400                2405                2410                2415
TGA TTC TAA GAT TTG GTT TGG GAT CAA TAG GAA AGC ATA TGC AGC CAA    7297
2420                2425                2430
CCA AGA TGC AAA TGT TTT GAA ATG ATA TGA CCA AAA TTT TAA GTA GGA    7345
2435                2440                2445
AAG TCA CCC AAA CAC TTC TGC TTT CAC TTA AGT GTC TGG CCC GCA ATA    7393
2450                2455                2460
CTG TAG GAA CAA GCA TGA TCT TGT TAC TGT GAT ATT TTA AAT ATC CAC    7441
2465                2470                2475
AGT ACT CAC TTT TTC CAA ATG ATC CTA GTA ATT GCC TAG AAA TAT CTT    7489
2480                2485                2490                2495
```

FIG. 2H-4

```
TCT CTT ACC TGT TAT TTA TCA ATT TTT CCC AGT ATT TTT ATA CGG AAA    7537
                2500                2505                2510
AAA TTG TAT TGA AAA CAC TTA GTA TGC AGT TGA TAA GAG GAA TTT GGT    7585
                2515                2520                2525
ATA ATT ATG GTG GGT GAT TAT TTT TTA TAC TGT ATG TGC CAA AGC TTT    7633
                2530                2535                2540
ACT ACT GTG GAA AGA CAA CTG TTT TAA TAA AAG ATT TAC ATT CCA CAA    7681
                2545                2550                2555
AAAAAAAAA AAAAAAAAA AAAA                                           7705
```

FIG. 3A

PAIR 1
1 5'- AATTCATATGCAGGCACAGCAAATGGTTCAGCCCCAGTCCCCGGTGGCTGTCAGTCAAAGCAAGCCCGTT -3'
2 3'- GTATACGTCCGTGTCGTTTACCAAGTCGGGGTCAGGGGCCACCGACAGTCAGTTTCGTTCGGGCCAACAACAATA -5'

PAIR 2
3 5'- GTTATGACAATGAAAACACTATCAGATAAATCAACAGTGGGAGCGGACCTACCTAGGTGAATGTGTTG -3'
4 3'- CTGTTACCTTTTGTGATAGTCTATTTAGTTGTCACCCTCGCCTGGATGGATCCATT -5'

PAIR 3
5 5'-      GTTTGTACTTGTTATGGAGGAAGCCGAGGTTTTAACTGCGAAAGTAAACCTGAAGCT -3'
6 3'- ACACAACCAAACATGAACAATACCTCCTTCGGCTCCAAAATTGACGCTTTCATTTGGACTTCGACTTCTCT -5'

PAIR 4
7 5'- GAAGAGACTTGCTTTGACAAGTACACTGGGAACACTTACCGAGTGGGTGACACTTATGAGCGTCCTAAA -3'
8 3'-       GAACGAAACTGTTCATGTGACCCTTGTGAATGGCTCACCCACTGTGAATACTCGCAG -5'

FIG. 3B

PAIR 5

9 5'- GACTCCATGATCTGGGACTGTACCTGCATCGGGGCTGGGCGAGGAGAATAAGCTGTACC -3'
10 GATTCTGAGGTACTAGACCCTGACGTAGACGTAGCCCCGACCCCGCTCCCTCTATTC -5'

PAIR 6

11 5'- ATCGCCAACGCTGCCATGAAGGGGTCAGTCCTACCAGATTGGTGACACCTGGAGGAGACCACATGAGACT -3'
12 3'- GACATGGTAGCCGTTTGCGACGGTACTTCCCCAGTCAGGATGGTCTAACCACTGTGGACCTCCTCTGGTGTACTCTGA -5'

PAIR 7

13 5'- GGTGGTTACATGTTAGAGTGTGTGTGTCTTGGTAATGGAAAAGGAGAATGACCTGCAAGCCCATAGCTGAG -3'
14 3'- TGTACAATCTCACACACAGAACCATTACCTTTCCTCTTACCTGGACGTTCGGGTATCGACTCCTAG -5'

FIG. 6
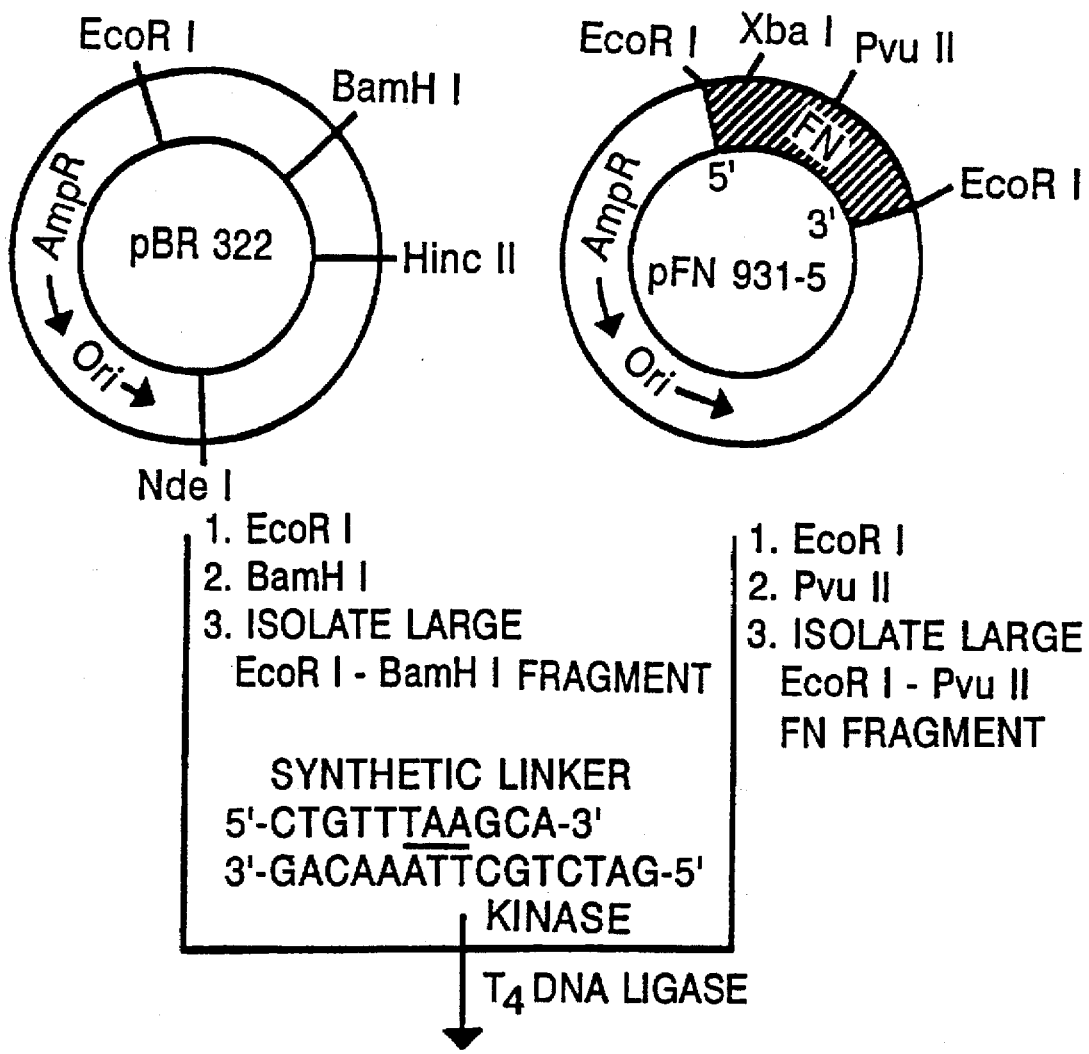
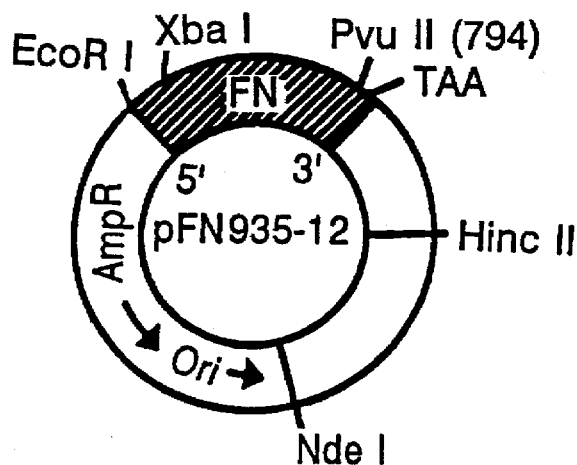

FIG. 11
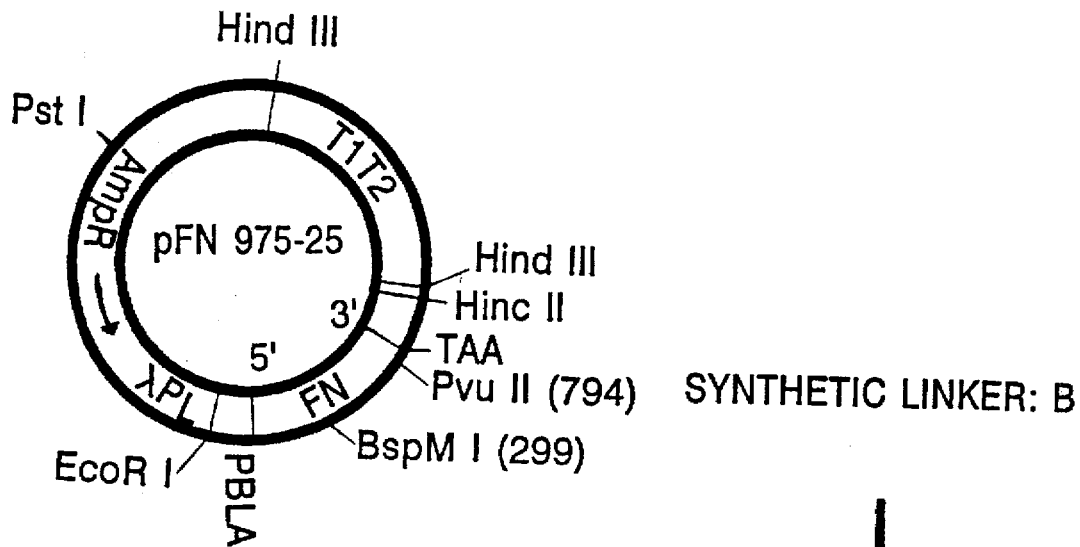
1. DIGEST WITH BspM I + Hind III
2. ISOLATE LARGE BspM I - Hind III FRAGMENT
T4 DNA LIGASE
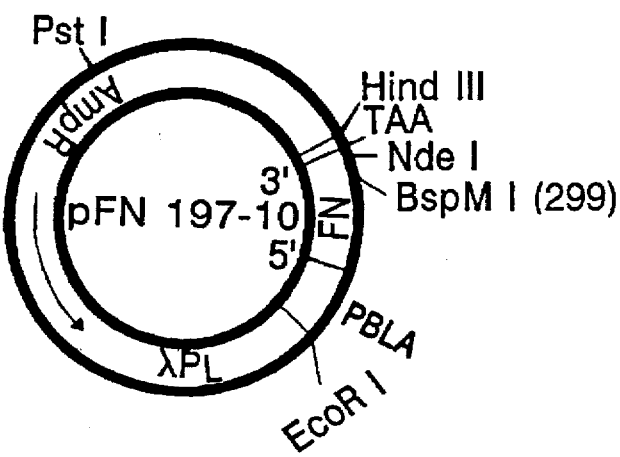

FIG. 15A

5' GGGCTGGGCGAGGGAGAATAAGCTGTACCATGCDAAACCGCTAACAGCTGA 3'
3' ACCCGCTCCCTCTTATTCGACATGGTAGCGTTTGGCGATTGTCGACTTCGA 5'

FIG. 15B

5' GGGCTGGGCGAGGGAGAATAAGCTGTACCATGCGCAAACCGCCATATGTAAA 3'
3' ACCCGCTCCCTCTTATTCGACATGGTAGCGTTTGCGGTATACATTTCGA 5'

FIG. 15C

5' ATGGCCGTGGAGACAGCTAACAGCTGA 3'
3' TACCGGCACCTCTGTCGATTGTCGACTTCGA 5'

FIG. 15D

5' CTGTATACCAACC 3'
3' GACATATGGTTGGAT 5'

18.41

18.20

15.31

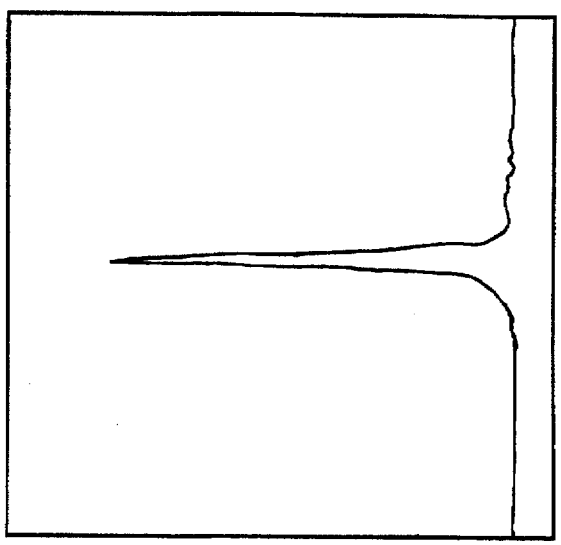
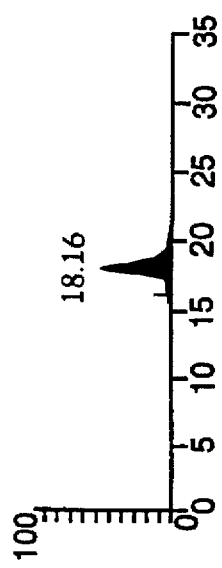
FIG. 21D-1  FIG. 21E-1  FIG. 21F-1
FIG. 21D-2  FIG. 21E-2  FIG. 21F-2
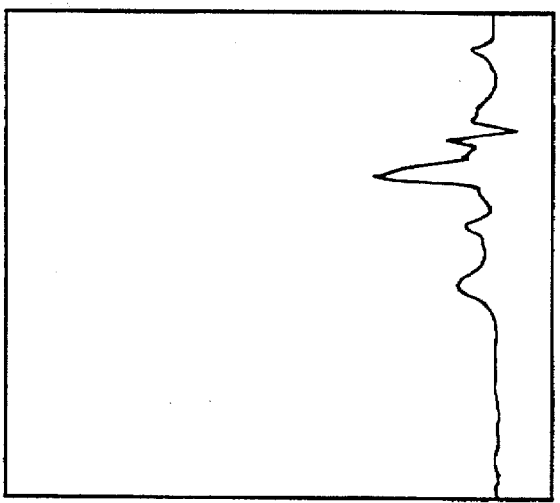
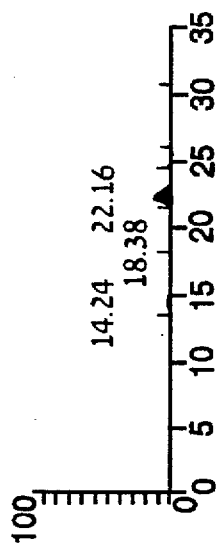
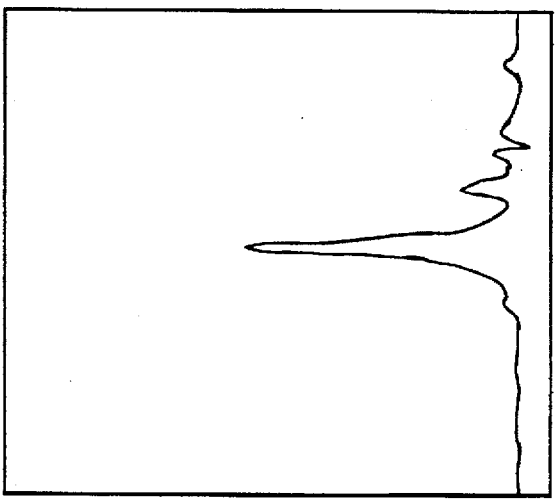
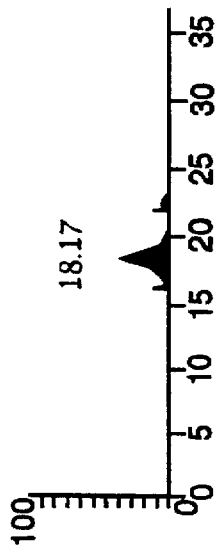

FIG. 24

5' GCCCATAGCTGAAAAGTAATTTGATCATGCTGC 3'

FIBRIN BINDING DOMAIN POLYPEPTIDES AND USES AND METHODS OF PRODUCING SAME

This application is a continuation of U.S. Serial No. 07/703,842, filed May 21, 1991, now abandoned; which is a continuation-in-part of U.S. Ser. No. 07/526,397, filed May 21, 1990, now U.S. Pat. No. 5,270,030, issued Dec. 14, 1993; which is a continuation-in-part of U.S. Ser. No. 07/345,952, filed Apr. 28, 1989, now abandoned; which is a continuation-in-part of U.S. Ser. No. 07/291,951, filed Dec. 29, 1988, now abandoned.

BACKGROUND OF THE INVENTION

Throughout this application, various publications are referenced by Arabic numerals within parentheses. Full citations for these references may be found at the end of the specification immediately preceding the claims. The disclosures of these publications in their entireties are hereby incorporated by reference in this application in order to more fully describe the state of the art to which this invention pertains.

Endothelial injury is believed to be an initial step in thrombus formation and may be caused by, e.g., hemodynamic strain, hypercholesterolemia, hypertension and immune complex disease. Endothelial injury leads to thickening of the intima, cell proliferation, cholesterol accumulation, and formation of connective tissue fibers. IgG and complement factor C3 accumulation in injured endothelial cells and nonendothelialized intima has been observed. Mononuclear cells derived from blood are also part of the cell population in atherosclerotic lesions. The mechanism of plaque formation is not fully known. However, a probable mechanism is that the earliest lesions, fatty streaks, consisting of mixtures of T cells and monocyte-derived macrophages, form in the subendothelium followed by a secretion of various cytokines, which leads to a migration of smooth cells into the intima and their accumulation therein.

Most existing procedures for the diagnosis and treatment of atherosclerosis and thrombosis are invasive, costly, and of limited effectiveness in a significant percentage of patient cases.

The concept of plaque enhancement by application of a stain has been reported [Spears, J. et al., J. Clin. Invest. 71:395–399 (1983)]. These stains mark the plaque surfaces with a fluorescent compound. Plaque destruction by photoactivation of hematoporphyrin derivatives using an intraluminal laser-transmitting optical fiber has been suggested [Abela, G. et al., Am. J. Cardiol. 50:1199–1205 (1982)]. Moreover, tetracycline stains have also been suggested. [Murphy-Chutorian, D. et al., Am. J. Cardiol. 55:1293–1297 (1985)].

The above-identified stains were selected for their ability to bind to components of the atherosclerotic plaque. In principle, the stain absorbs laser light concentrating the light at the stained surface. Some staining of healthy tissue occurs causing stain associated damage to the surrounding tissue. Because laser light wavelength is limited to the absorption wavelength of the stain, chromophores offering optimum-absorption of laser light must be used to provide best controlled ablation.

Imaging and detection of coronary thrombi, pulmonary emboli, deep venous thrombosis and atherosclerotic lesions are of great clinical importance especially in view of the new thrombolytic agents which have recently been developed.

Several experimental approaches for non-invasive detection of thrombi by use of radiopharmaceutical agents have been reported but none has gained wide clinical recognition because of intrinsic drawbacks associated with each agent.

The basic characteristics of a radiopharmaceutical for early detection of intravascular atherosclerotic lesions and thrombi are the following: (i) high affinity for thrombus components; (ii) relatively fast pharmacokinetic blood clearance rate [in order toobtain a high ratio of thrombus (bound) to blood (unbound) radiolabeled tracer]; (iii) safety: nontoxic and non-immunogenic; and (iv) simplicity of preparation and use.

The various agents for imaging thrombi described in the literature and their drawbacks are as follows: (a) autologous platelets labeled with $^{111}$In: the procedure is cumbersome, time consuming and the blood clearance time is relatively long, viz. 2 days (2); (b) $^{131}$I-fibrinogen: the assay is based on the (low) affinity of injected radiolabeled fibrinogen for the thrombus but it is not suitable for rapid imaging tests because of its long residence time in blood and furthermore it does not become incorporated into older thrombi nor is it incorporated in the presence of heparin (3, 36); (c) fragment E1 of human fibrin: although it seems superior to fibrinogen it is difficult to prepare in sufficientquantities for widespread clinical use (4); (d) mouse anti-fibrin monoclonal antibodies: although they are specific and have high affinities for thrombi, they have a relatively long blood clearance time and are potentially immunogenic to human subjects (5, 33, 34); (e) mouse monoclonal antibodies specific for activated platelets (6, 7): disadvantage as (d); and (f) labeled fibronectin (1): although fibronectin (see below) has an affinity for a number of substances occurring in thrombi it has a relatively long blood clearance time and the buildup of radioactivity in the thrombus is slow. Thus there is a need in the art for a thrombus-specific radiopharmaceutical for rapid imaging of thrombi.

U.S. Pat. No. 4,343,734 (Lian et al.) describes specific gamma-carboxyglutamic acid (GLA) antibodies which can be labeled with fluorescein for immunofluorescence staining of tissue to determine the presence therein of GLA. Specific GLA antibodies bind to GLA which is present in advanced atherosclerotic plaque, having calcium deposits. Lian et al. report that GLA is not found in uncalcified plaques and that GLA is found in cardiac valves and aortas, and in circulating proteins such as prothrombin, clotting factors VII, IX and X, Protein C and Protein S. However, the GLA binding antibodies of Lian et al. do not selectively bind to atherosclerotic plaques.

Fibronectin is a glycoprotein composed of two identical subunits each of approximately 220,000 molecular weight. Two major forms of fibronectin are produced and secreted by human cells in culture and in vivo (8). The cell-associated fibronectin is relatively insoluble and participates in cell adhesion, wound healing, cell differentiation and phagocytosis. The plasma fibronectin, produced primarily in the liver, is a soluble serum protein with biological properties similar to those of cell fibronectin.

Fibronectin is considered a multifunctional modular protein since limited proteolytic cleavage produces polypeptides with distinct activities. The major functional domains of the fibronectin molecule have been obtained and defined by partial proteolytic digestion, and include heparin, DNA, fibrin, collagen or gelatin, and cell binding domains (8–13).

Baralle, F. E., European Patent Publication No. 207,751, published Jan. 7, 1989, discloses the complete cDNA sequence of fibronectin. Baralle also discloses the expression of fusion proteins containing a portion of the collagen binding domain of fibronectin fused to the *Escherichia coli* protein β-galactosidase. Similar fusion proteins are disclosed by Owens and Baralle (14). Obara et al. (1987) disclose the expression of a portion of the cell binding domain of human fibronectin fused to *Escherichia coli* β-*galactosidase* (15). Additionally, Obara et al. (1988) disclose the expression of portions of the cell binding domain fused to β-galactosidase which have been mutagenized, i.e., site specific deletions of portions of the cell binding domain were obtained as fused proteins (16). The carboxy terminal fibrin-binding domain of human fibronectin has been expressed in mouse L cells as a fusion protein with the signal sequence of human protein C inhibitor (17).

None of the above references discloses the expression of the N-terminal fibrin binding domain of fibronectin; furthermore all the recombinant proteins they disclose are fusion proteins.

This invention provides polypeptides having an amino acid sequence substantially present in the N-terminal fibrin binding domain of fibronectin. These polypeptides have approximate molecular weights of 31 kD, 20 kD, 18.5 kD and 12 kD, as defined by comparison markers on SDS gels under reducing conditions, and have the following characteristics which make them promising pharmaceutical agents: (i) have an amino acid sequence present in a human protein and thus are contemplated to not be immunogenic; (ii) have specificity to fibrin based on their ability to become covalently cross-linked in a trans-glutaminase catalysed reaction to nascent as well as to preformed thrombi (clots); (iii) bind to extracellular matrix, which property may be exploited to detect atherosclerotic plaques; (iv) have a relatively short blood clearance time; (v) incorporate into clots in the presence of heparin; and (vi) are produced by recombinant techniques and can therefore potentially be manufactured on a large scale.

The subject invention provides an inexpensive, accurate method for imaging fibrin-containing substances, i.e., a thrombus and atherosclerotic plaque, both in vitro and in vivo. In addition, the subject invention provides plasmids for expressing polypeptides having an amino acid sequence substantially present in the fibrin binding domain of naturally-occurring human fibronectin and capable of binding to fibrin which are labeled and used for imaging the fibrin-containing substances, and methods of producing such polypeptides.

SUMMARY OF THE INVENTION

This invention provides imaging agents which comprise polypeptides labeled with an imageable marker, such polypeptide having an amino acid sequence substantially present in the fibrin binding domain of naturally-occurring human fibronectin and being capable of binding to fibrin.

Further provided is a method for imaging a fibrin-containing substance, i.e. a thrombus or atherosclerotic plaque, which comprises contacting the fibrin-containing substance to be imaged with the imaging agent disclosed above under conditions such that the agent binds to the fibrin-containing substance and imaging the bound agent and thereby imaging the fibrin-containing substance.

Also provided is a plasmid for expression of a polypeptide which having an amino acid sequence substantially present in the fibrin binding domain of naturally-occurring human fibronectin and being capable of binding to fibrin comprising DNA encoding the polypeptide and DNA encoding suitable regulatory elements positioned relative to the DNA encoding the polypeptide so as to effect expression of the polypeptide in a suitable host cell.

The invention also provides a purified polypeptide substantially free of other substances of human origin which has an amino acid sequence substantially present in the fibrin binding domain of naturally-occurring human fibronectin and being capable of binding to fibrin.

Further provided are methods of recovering and refolding and reoxidizing such polypeptides and methods of treatment using such polypeptides.

BRIEF DESCRIPTION OF THE FIGURES

In the figures, the numbers in brackets adjacent certain of the restriction enzyme sites shown correspond to the identically numbered positions along the nucleotide sequence of human fibronectin cDNA as shown in FIG. 2A-1 to 2H-4 (SEQ ID NO. 16) (see also FIG. 3 of Baralle, F. E., European Patent Publication No. 207,751, published Jan. 7, 1987).

The following figures describe the construction of plasmids expressing polypeptides having an amino acid sequence substantially present in the amino-terminal fibrin binding domain (FBD) of fibronectin. The FBD commences at amino acid number 1 of mature fibronectin, which is glutamine and corresponds to the fourth amino acid (Q) shown in FIG. 2A-1, (SEQ ID NO. 16) i.e., the N-terminus of the FBD sequence is Q-A-Q-Q (glutamine-alanine-glutamine-glutamine) (SEQ ID NO. 16); the corresponding first nucleotide in the cDNA sequence of FIG. 2A is therefore number 14, indicated by an arrow. All the recombinant FBD polypeptides described in these figures and throughout the specification are numbered from this first glutamine as amino acid number 1 and all the corresponding cDNA sequences are numbered as shown in FIGS. 2A-1 to 2H-4 (SEQ ID NO. 16).

Some of the figures describe the construction of plasmids expressing an FBD polypeptide joined at its C-terminus to part of the cell binding domain (CBD) of fibronectin. The cDNA sequence corresponding to the CBD which applicants have cloned and expressed is missing the 270 bp extra domain (ED) segment which extends from nucleotides 4811 to 5080, inclusive, on the Baralle map (see FIGS 2A-1 to 2H-4) (SEQ ID NO 16). Thus, the cDNA sequence which is said to extend from nucleotide 3317 to 5566 on the Baralle map, contains only 1980 nucleotides, because it is missing the 270 nucleotides of the ED segment, namely from nucleotides 4811 to 5080 inclusive; this region is also known in the art as the ED-A region. Because nucleotide 5081 is changed from G to A, the amino acid 1690 is changed from alanine to threonine. Similarly, the polypeptide expressed bythat DNA fragment would encode from amino acid 1102 to amino acid 1851 on the Baralle map but 5 would be missing the 90 amino acids encoded by the ED region, namely amino acids 1600–1689 inclusive, and thus it would contain only 660 amino acids. This is true for all CBD polypeptides described in this application which span the ED region. (The region known in the art as the ED-B region is missing both in Baralle's sequence and in applicants' DNA.)

The definition of the polypeptides expressed as 31 kD, 20 kD, 18.5 kD, 12 kD and 33 kD is an operational definition, based on their approximate molecular weight determined on SDS polyacrylamide gels under reducing conditions compared to that of markers of known molecular weight.

Figure 1:
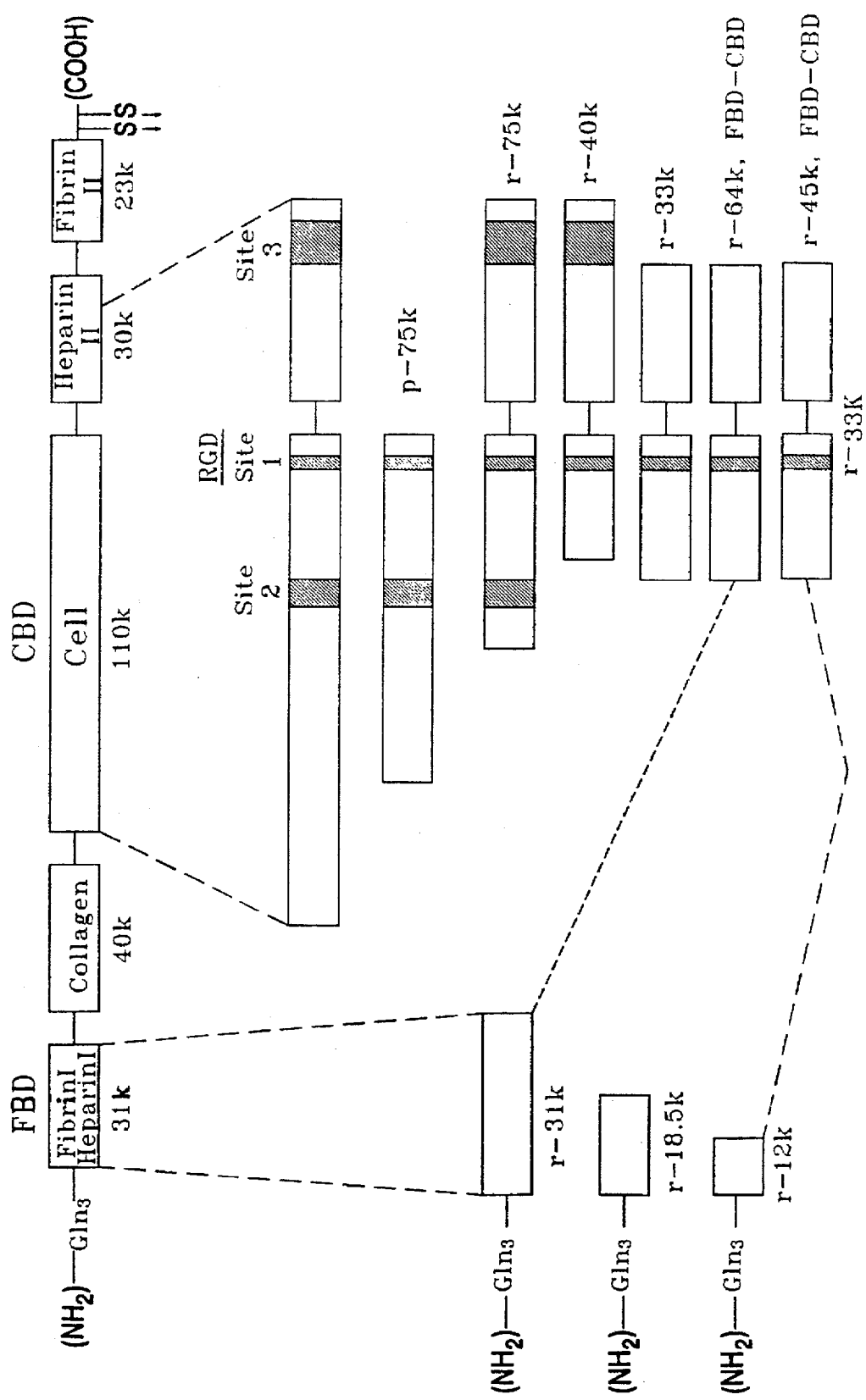

FIG. 1. This figure is a schematic description of the various fibronectin domains and the recombinant polypeptides constructed.

FIG. 2A1–2H-4 (SEQ ID NO. 16). These figures show the nucleotide sequence of human fibronectin cDNA.

Figure 4:
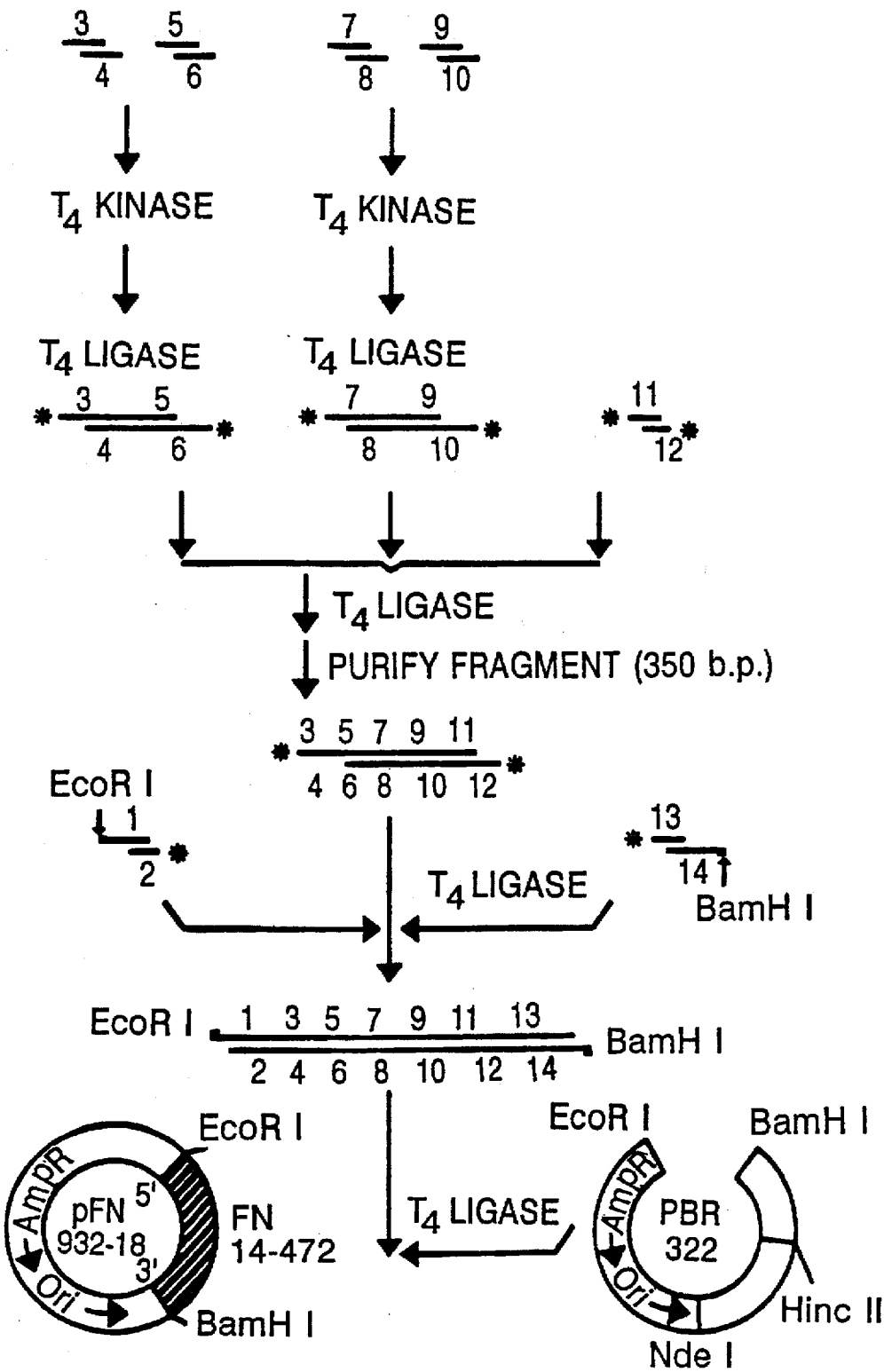

FIGS. 3A–3B (SEQ ID NOS. 17–30). Seven pairs of chemically synthesized oligomers were prepared. The synthetic oligomers code for the first 153 N-terminal amino acids of human fibronectin (FN). These figures show the sequence of these 7 pairs of synthetic oligomers. FIG. 4. The DNA fragment coding for amino acids I to 153 of the N-terminal domain of human FN was assembled from the 7 pairs of chemically synthesized oligomers shown in FIGS 3A and 3B follows:

Oligomers 3/4, 5/6, 7/8 and 9/10, each pair in a separate tube, were annealed and then phosphorylated at the 5' end using T4 polynucleotide kinase enzyme.

In the second step, pairs 3/4 and 5/6 were ligated to each other using T4 DNA ligase. Similarly, reaction pairs 7/8 and 9/10 were ligated to each other. After each step of ligation an aliquot of the ligation mixture was analyzed on gel to determine the size of the newly formed fragments and the efficiency of ligation.

In the third step, the two above mentioned ligation mixtures were mixed together and pair 6, oligomers 11/12 which had been annealed and phosphorylated previously in a separate tube were added to the mixture. A 326 base pair DNA fragment obtained from the above ligation mixture was isolated from an agarose gel and purified.

The purified synthetic 326 fragment was added to two additional pairs of synthetic linkers: Pair 1, oligomers 1/2 and Pair 7 oligomers 13/14. In Pair 1 only oligomer 2 was phosphorylated at the 5' end and in Pair 7 only oligomer 13 was phosphorylated at the 5' end.

After ligation with T4 DNA ligase the mixture without any further isolation was added to pBR322 vector DNA digested with EcoRI and BamHI endonucleases.

The plasmid obtained, designated pFN 932-18 contained the entire synthetic EcoRI (5' end) - BamHI (3' end) restriction fragment coding for the N-terminal 153 amino acids of human FN, in a pBR322 vector.

Figure 5:
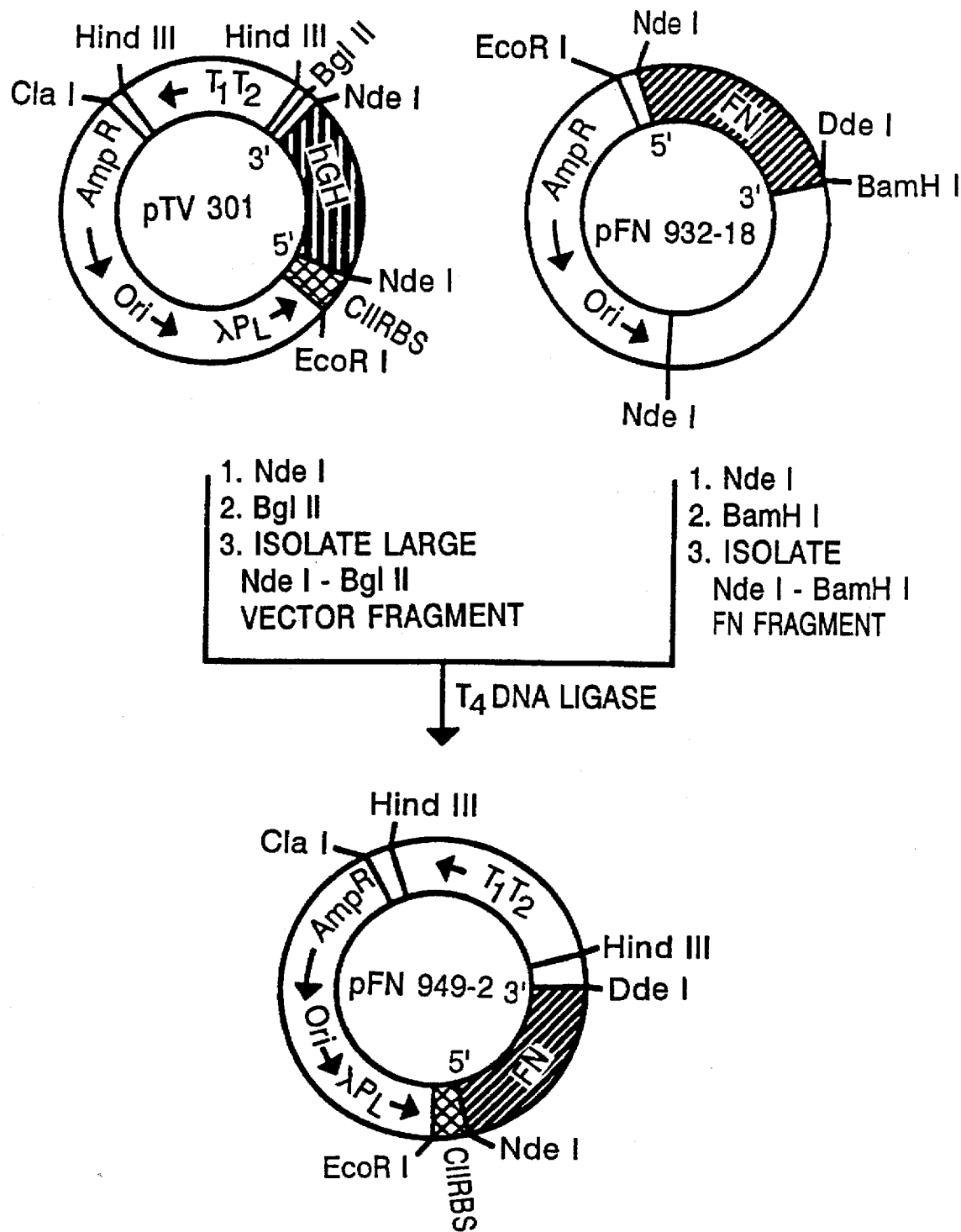

FIG. 5. Expression of the N-terminal 153 amino acid sequence of IN.

Plasmid pFN 932-18 was digested with NdeI and BamHI endonucleases. The NdeI-BamHI DNA fragment coding for FN (first 153 amino acids +additional N-terminal methionine) was isolated and ligated into the large fragment obtained by digestion of plasmid pTV301 with NdeI and BglII endonucleases. (Plasmid pTV301 expresses human growth hormone, hGH, under the control of $\lambda P_L$ promoter and the cII The plasmid obtained was designated pFN949-2.

FIG. 6. Insertion of termination codon TAA at the 3' end of the N-terminal domain of FN (at amino acid 262)

A synthetic oligonucleotide containing a TAA termination codon and a BglII site having the following sequence:

CTGTTTAAGCA (SEQ ID NO. 2)

GACAAATTCGTCTAG (SEQ ID NO. 3)

was ligated to the 3' end (PvuII site) of an EcoRI-PvuII FN fragment isolated from cDNA plasmid p931-5 (see FIG. 6) (SEQ ID NOS 2&3) digested with EcoRI and PvuII. The ligation was carried out in the presence of DNA vector plasmid pBR322 digested with EcoRI and BamHI (large fragment). The plasmid obtained was designated pFN935-12.

Figure 7:
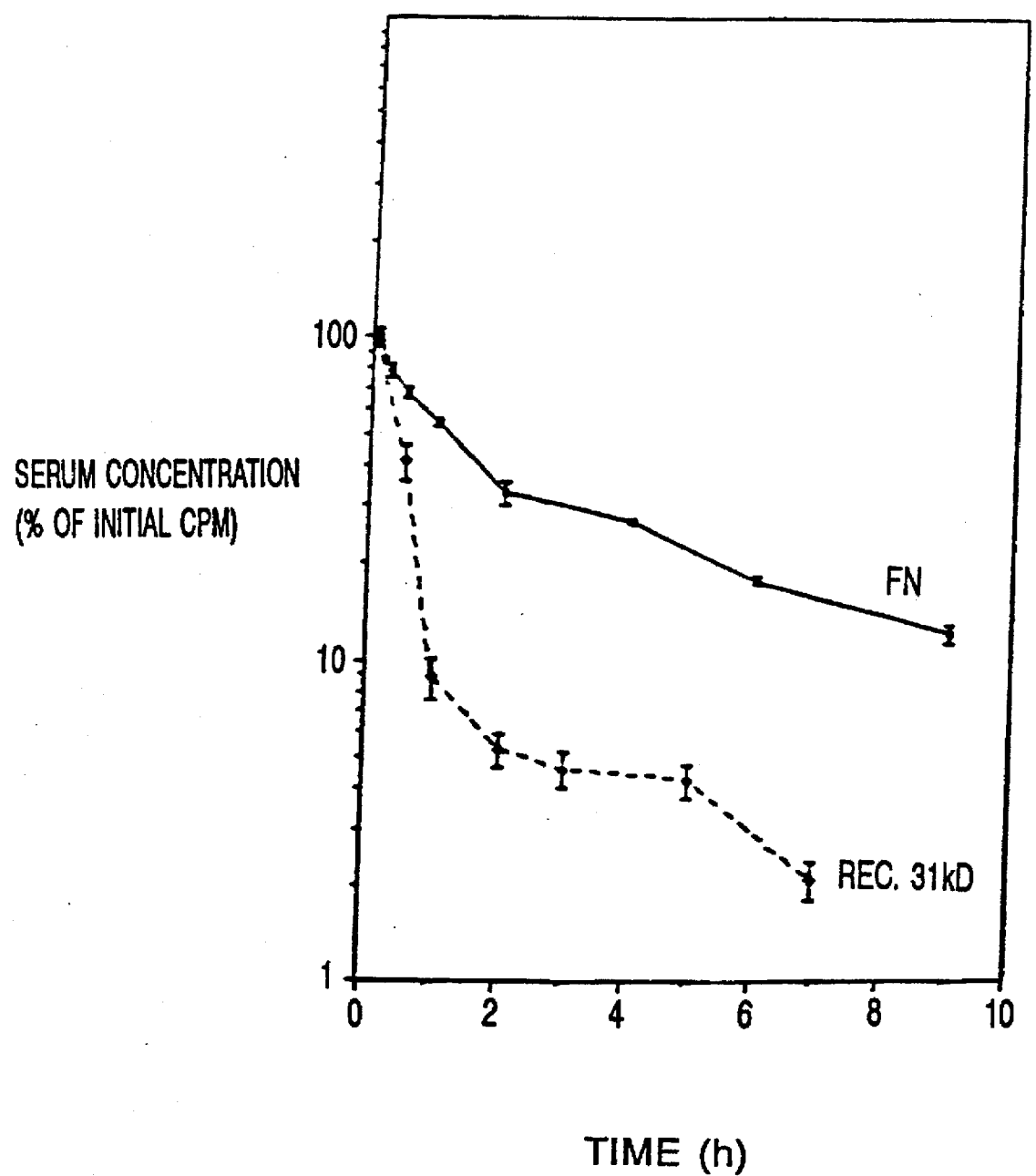

FIG. 7. Comparison of the pharmacokinetics of fibronectin (FN) and r31 kD FBD in rats $^{125}$I-FN (0.1 mg/kg; 5×10$^6$ cpm) or $^{125}$I-r31 FBD (0.1 mg/kg; 5×10$^6$ cpm) were injected intravenously and at the time indicated blood samples were withdrawn. Insoluble radioactivity in the blood samples was determined by trichloroacetic acid precipitation; at zero time, the 100% value represents 40,000 cpm/ml for FN and 46,000 cpm/ml for FBD.

Figure 8:
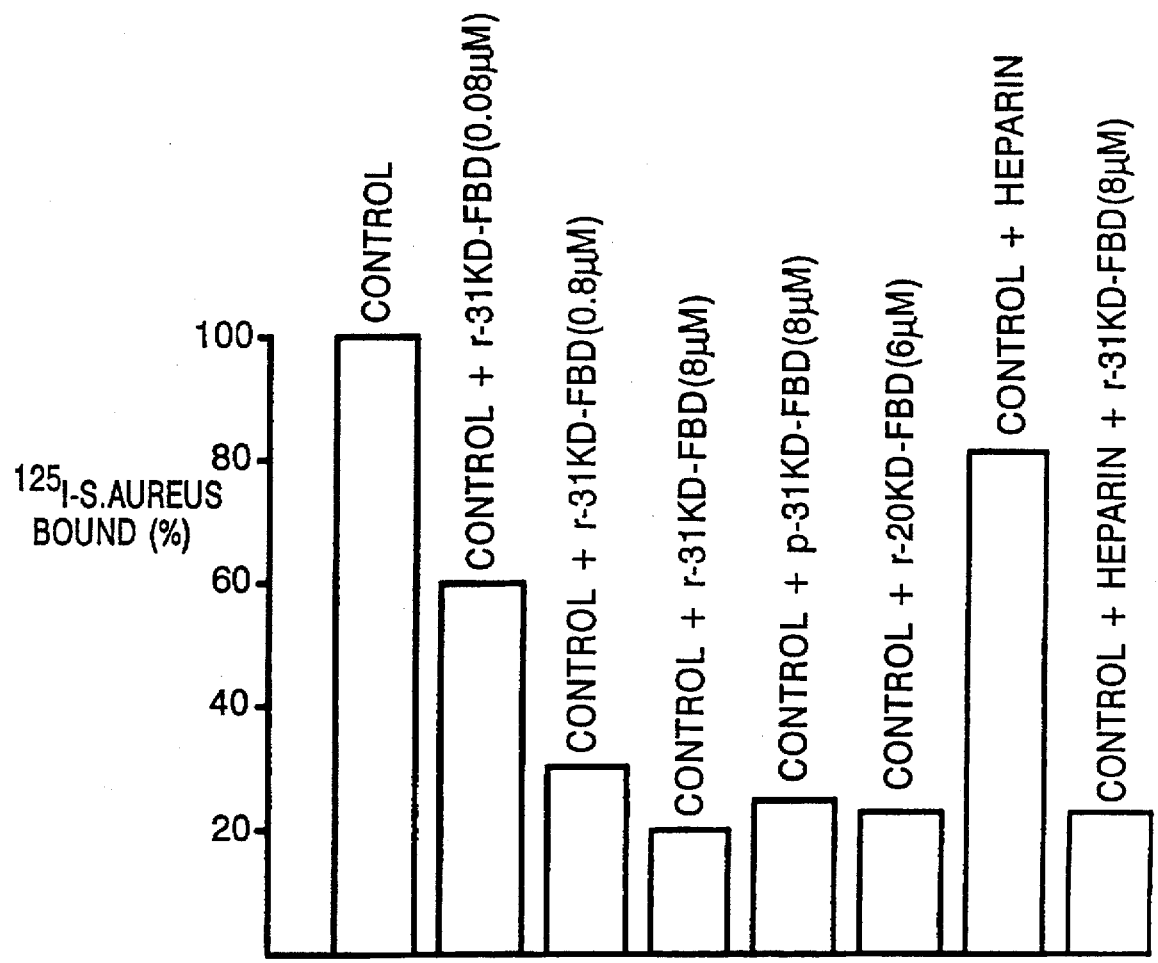

FIG. 8. Binding of S. aureus to Catheters

Binding of 3.0×10$^6$ PFU/ml of 125I-S. aureus (1 CPM/3 PFU) to "Uno" bronchial plastic catheters (3 cm for each reaction, in duplicate) coated with FN was carried out as described in methods. When competition reactions were performed, the bacteria and the added protein were preincubated at room temperature for 30 minutes and then added to the catheters for further incubation as described in the methods section.

The polypeptides used in the competition reactions were: P-31 (p31 kD), r-20 (recombinant 20 kD FBD polypeptide fragment) and r-31 (reoxidized and refolded r31kD). Some of the reactions (see figure) were measured in the presence of 5 µM Heparin (from porcine intestinal mucosa, molecular weight-10,000; Sigma).

The binding of the "control" reaction in the absence of competitors (8.8% of input bacteria) was normalized to 100%.

Figure 9:
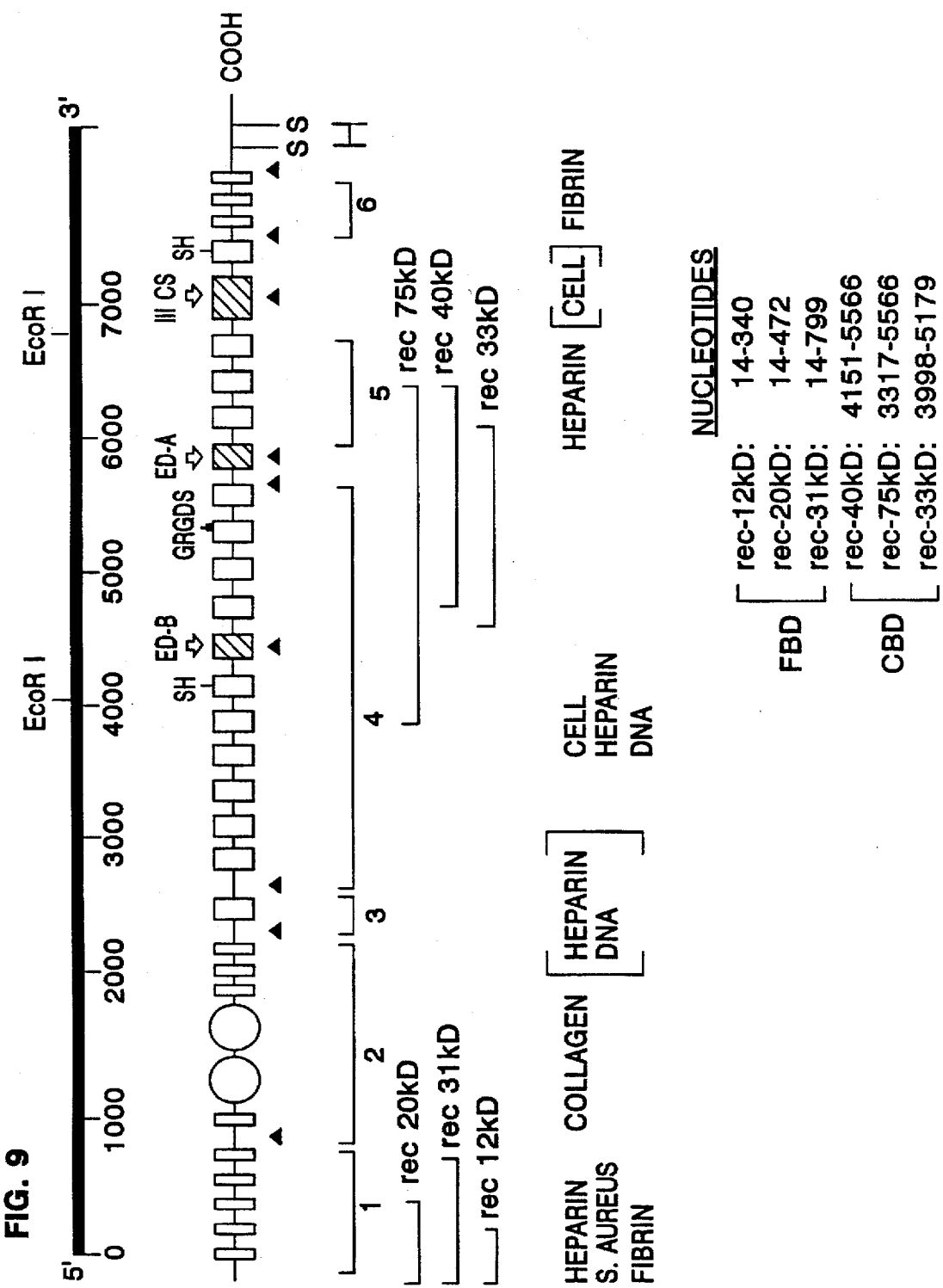

FIG. 9. Recombinant polypeptides of fibronectin domains compared to full-length fibronectin This figure shows the alignment of cDNA clones encoding various recombinant polypeptides relative to one another and to the full-length sequence of fibronectin cDNA and to a schematic representation of the various domains present within the human fibronectin molecule.

Figure 10:
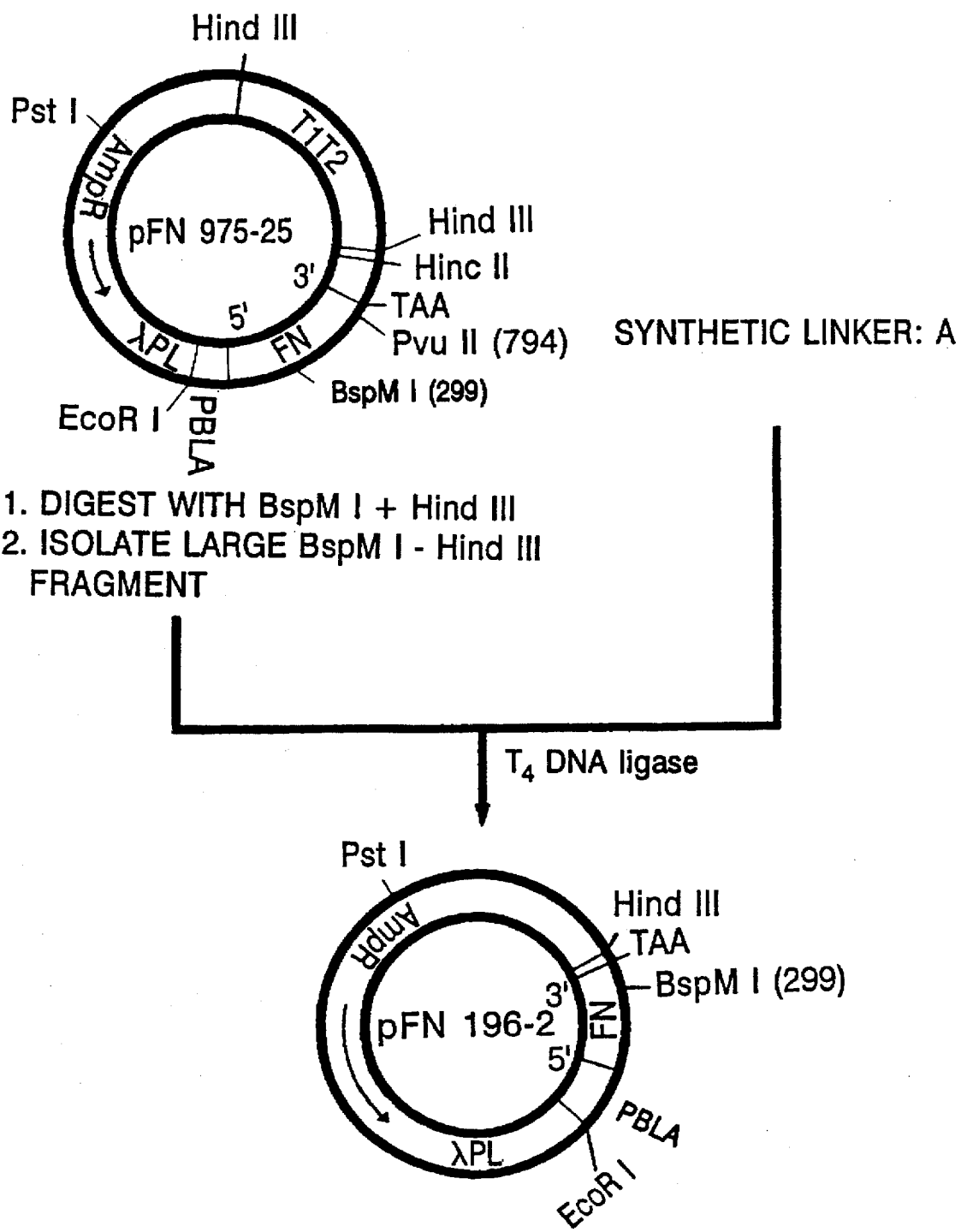

FIG. 10. Construction of plasmid pFN 196-2 which expresses the 712 kD FBD polypeptide The large BspMI-HindIII fragment obtained by digestion of plasmid pFN 975-25 (FIG. 10) with BspMI and HindIII was ligated by T4 DNA ligase to the synthetic pair of linkers A (see FIGS. 15A–15I) (SEQ ID NOS 31–38). Plasmid pFN 196-2 was produced, transformed into Escherichia coli strain A1645 and retransformed into Escherichia coli strain A4255. Plasmid pFN 196-2 contains the 5'-terminal sequence of fibronectin cDNA from nucleotide 14 to nucleotide 340, i.e., it encodes the first 109 amino acids of the FBD of fibronectin terminating with an arginine residue. An additional N-terminal methionine is present in the final polypeptide. Plasmid pFN 196-2 gives good expression of an r12 kD FBD polypeptide under the control of the λ promoter and β-lactamase ribosomal binding site, and has been deposited in the ATCC under Accession No. 68328.

FIG. 11. Construction of Rlasmid pFN 197-10, which expresses a modified 12 kD FBD polypeptide (12 kD')

Plasmid pFN 975-25 was treated as described in FIG. 10 except that a different pair of linkers, B (see FIGS. 15A–15D) (SEE ID NOS 31–38) was used. The ligation produced plasmid pFN 197-10 which encodes the N-terminal sequence of the FBD of FN; however, a modification after nucleotide 340 to produce an NdeI site (CATATG) before the stop codon results in the encoding of a polypeptide containing 111 amino acids where the first 109 amino acids correspond to those of the r12 kD polypeptide followed by two additional amino acid residues, viz. histidine and methionine. An additional N-terminal methionine residue is present in the final polypeptide. Plasmid pFN 197-10 was transformed into Escherichia coli strain A1645 and hence into Escherichia coli strain A4255, and gave good expression of a modified r12 kD (12 kD') FBD polypeptide under the control of the λ promoter and the β-lactamase ribosomal binding site.

Figure 12:
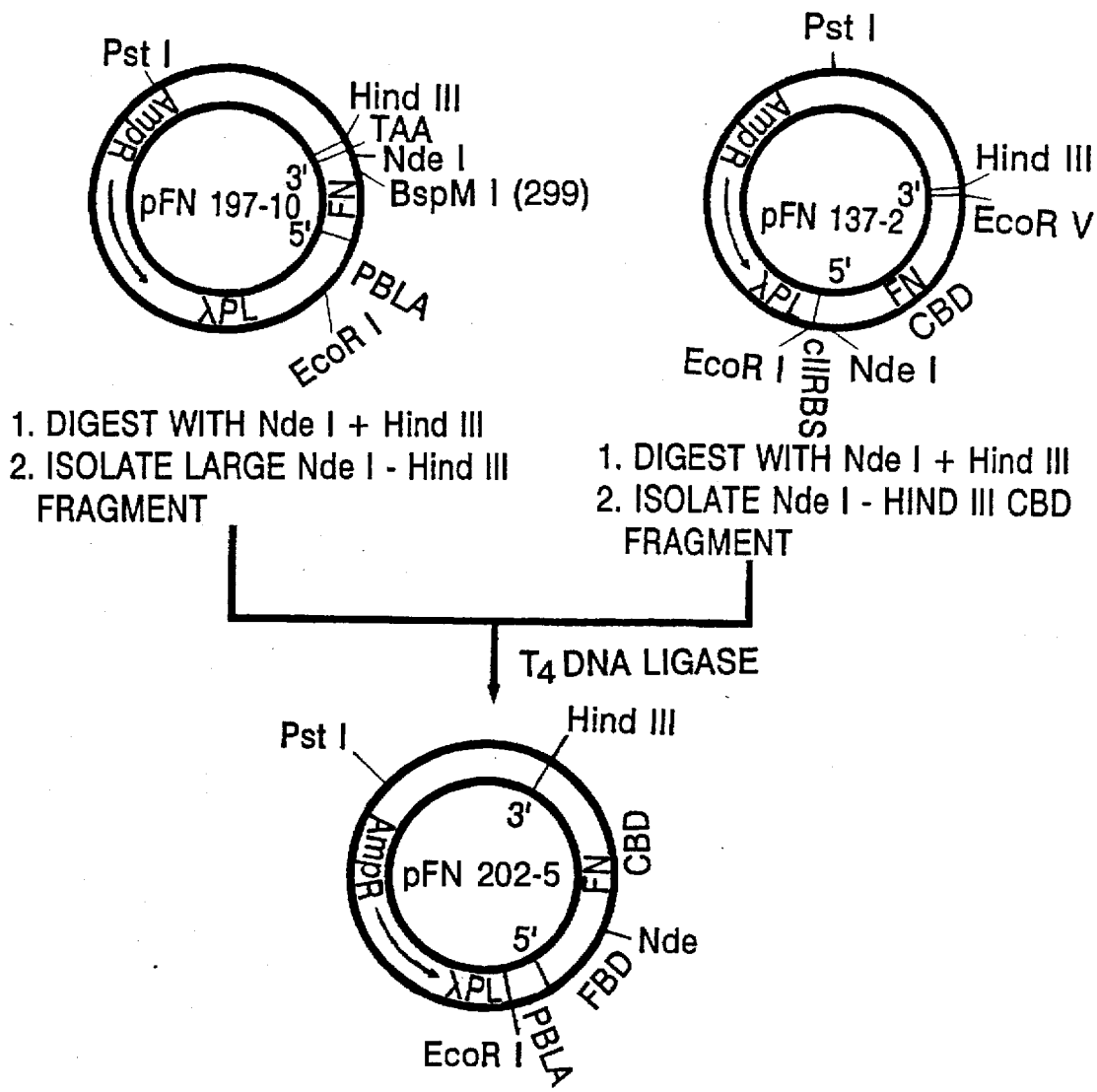

FIG. 12. Construction of plasmid pFN 202-5 which expresses r12 kD' FBD fused to the r33 KD cell binding domain (CBD) of Fibronectin The large fragment produced after NdeI and HindIII digestion of plasmid pFN 197-10 (FIG. 11) was ligated by T4 DNA ligase to the NdeI-HindIII CBD (cell binding domain) fragment of plasmid pFN 137-2. Plasmid pFN 137-2, deposited in the ATCC under Accession No. 67910 has been described in the parent patent application, U.S. Ser. No. 345,952; the r33 kD CBD sequence contains amino acids numbered 1329-1722 of fibronectin (see FIG. (2) (SEQ ID NO. 16) excluding the 90 amino acids numbered 1600-1689 encoded by the ED-A region (see preface to Brief Description of the Figures).

The resulting plasmid, pFN 202-5, was transformed into *Escherichia coli* strain A1645 and thence to *Escherichia coli* strain A4255. Plasmid pFN 202-5 contains the cDNA sequence of the 111 amino acids encoded by plasmid pFN 197-10 followed by the cDNA sequence for r33 kD CBD commencing with the codon for serine-(the first amino acid of the r33 kD CBD). This plasmid gave good expression of an approximately 45 kD polypeptide comprising the r12 kD fibrin binding domain and the 33 kD cell binding domain of fibronectin; this fused polypeptide was expressed under the control of the λ promoter and the β-lactamase ribosomal binding site.

Figure 13:
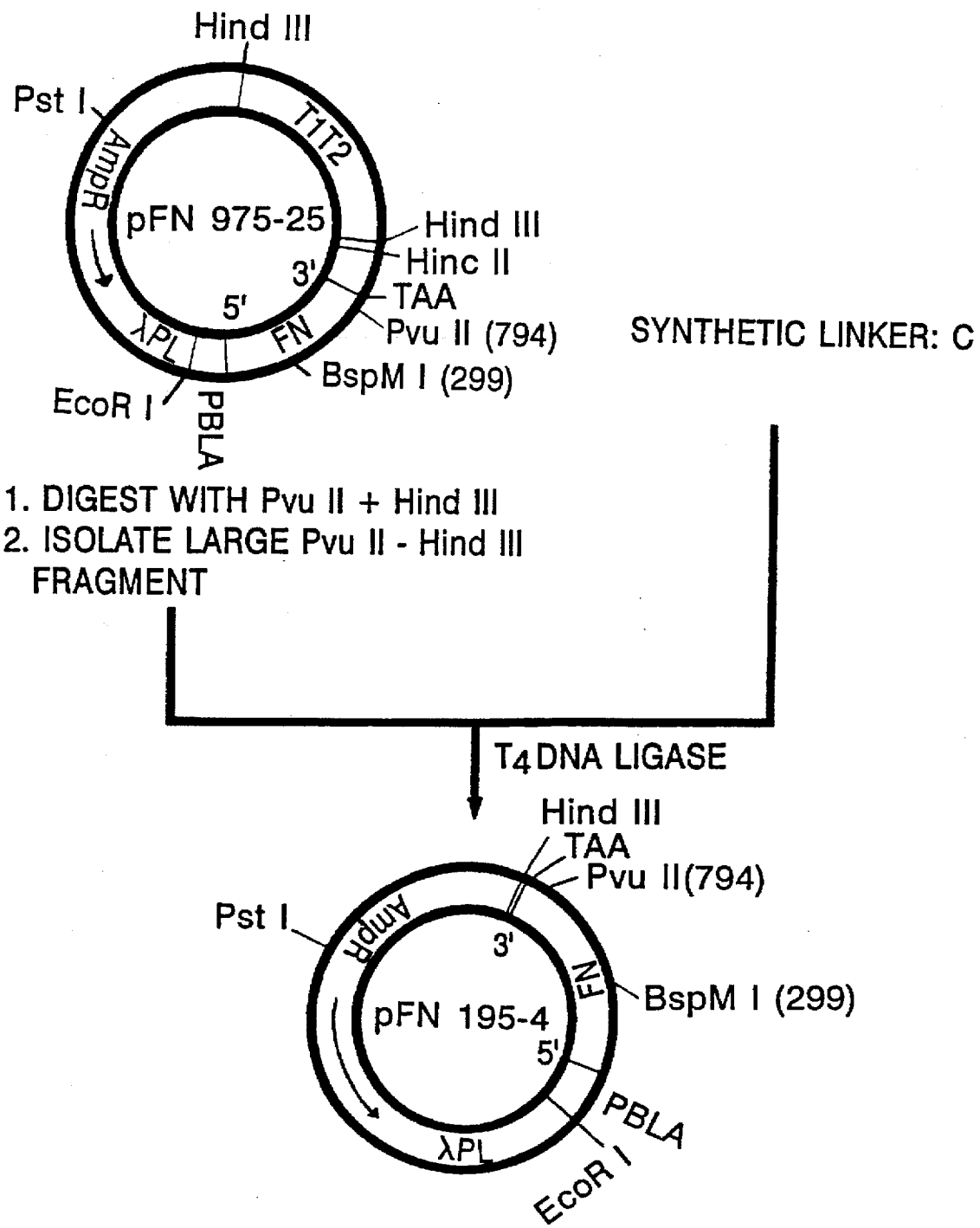

FIG. 13. Construction of plasmid DFN 195-4 which expresses the r31 kD FBD fused to the sequence DGRGDS The large fragment obtained by digestion of plasmid pFN 975-25 with PvuII and HindIII was isolated and ligated with T4 DNA ligase to a pair of synthetic linkers, C (see FIGS. 15A–15D) (SEQ ID NOS. 31–38) The resulting plasmid, designated pFN 195-4 was transformed into *Escherichia coli* strain A1645 and thence to *Escherichia coli* strain A4255. Plasmid pFN 195-4 contains the full-length FBD cDNA sequence from nucleotide 14 to nucleotide 793 (encoding 260 amino acids) followed by a sequence encoding asp-gly-arg-gly-asp-ser (SEQ ID NO. 4), i.e., the polypeptide encoded has a total of 260 amino acids followed by the sequence DGRGDS (SEQ ID NO. 4). An additional N-terminal methionine residue is present in the final polypeptide. Plasmid pFN 195-4 is a good expressor of the r31 kD fibrin binding domain fused to the sequence asp-gly-arg-gly-asp-ser (DGRGDS) (SEQ ID NO. 4) under the control of the λ promoter and the β-lactamase ribosomal binding site.

Figure 14:
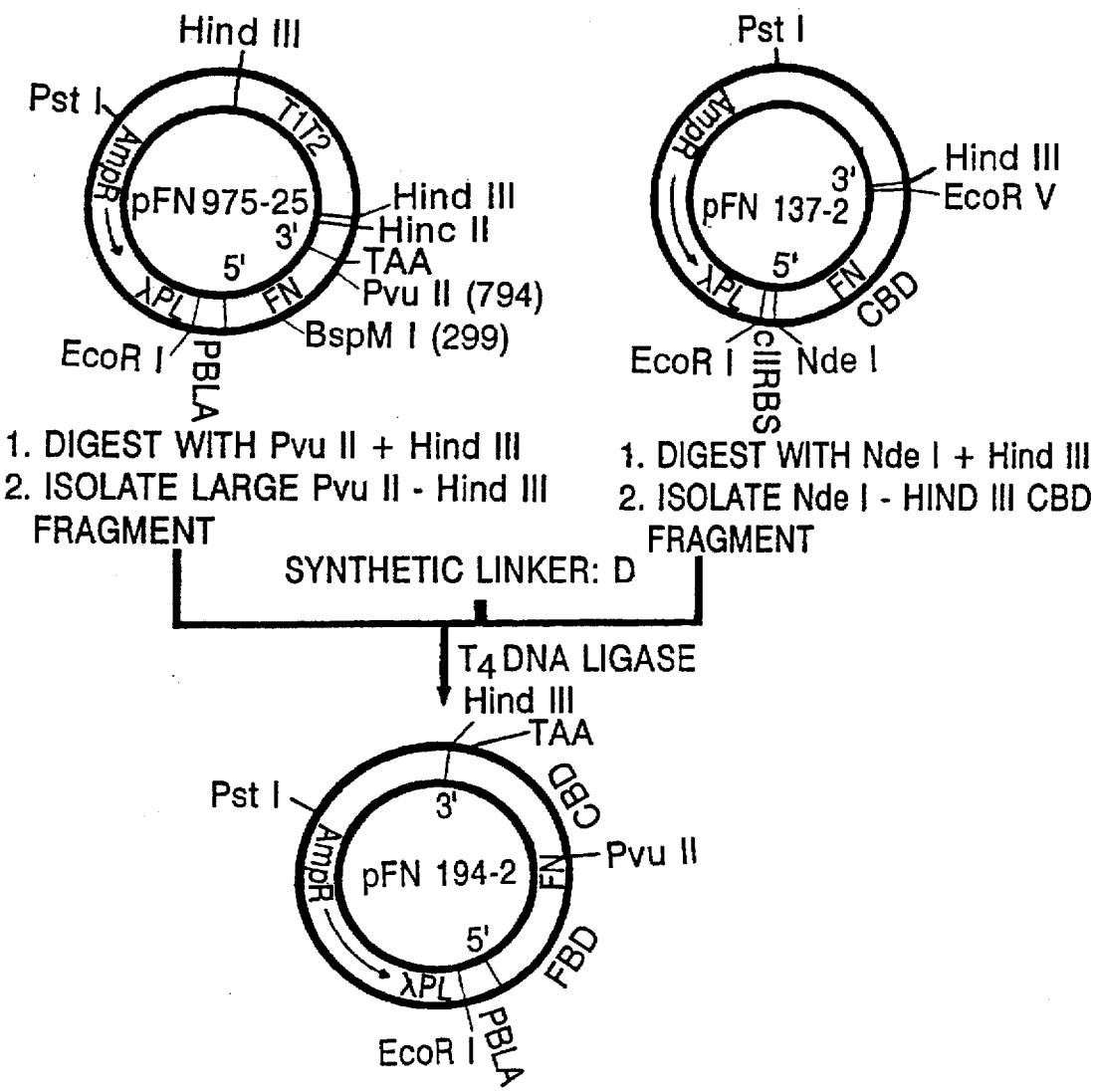

FIG. 14. Construction of plasmid pFN 194-2 which expresses a fused 31 kD FBD-33 kD CBD polypeptide The large PvuII-HindIII fragment produced by digestion of plasmid pFN 975-25 with PvuII and HindIII was isolated and ligated with T4 DNA ligase to a pair of linkers, D (FIG. 15A–15D) (SEQ ID NOS. 31–38) and then ligated to the cell binding domain (CBD) fragment obtained by digestion of plasmid pFN 137-2 (ATCC Accession No. 67910) with NdeI and HindIII; see FIG. 12 for definition of the CBD domain. The resulting plasmid, designated pFN 194-2, was transformed to *Escherichia coli* strain A1645 and thence to *Escherichia coli* strain A4255. Plasmid pFN 194-2 is a low expressor of a fused r31 kD FBD-r33 kD CBD polypeptide of approximate molecular weight 64 kD, under the control of the λ $P_L$ promoter and the β-lactamase ribosomal binding site. The polypeptide encoded by plasmid pFN 194-2 contains DNA encoding the first 265 amino acids of fibronectin fused to a methionine codon, followed by the cDNA sequence for the CBD of fibronectin, cgmmencing at the codon for amino acid serine at position i of the CBD.

One skilled in the art knows how to achieve high expression of the polypeptide expressed by plasmid pFN 194-2. An example of such a high expressor is plasmid pFN 205-5 described in FIG. 25.

FIG. 15A–15I. (SEQ ID NOS. 31–38) Oligonucleotide linkers used in construction of plasmids Four pairs of chemically synthesized oligomers (A, B, C and D) were prepared and were used to construct plasmids as described in FIGS. 10, 11, 13 and 14, respectively).

Figure 16:
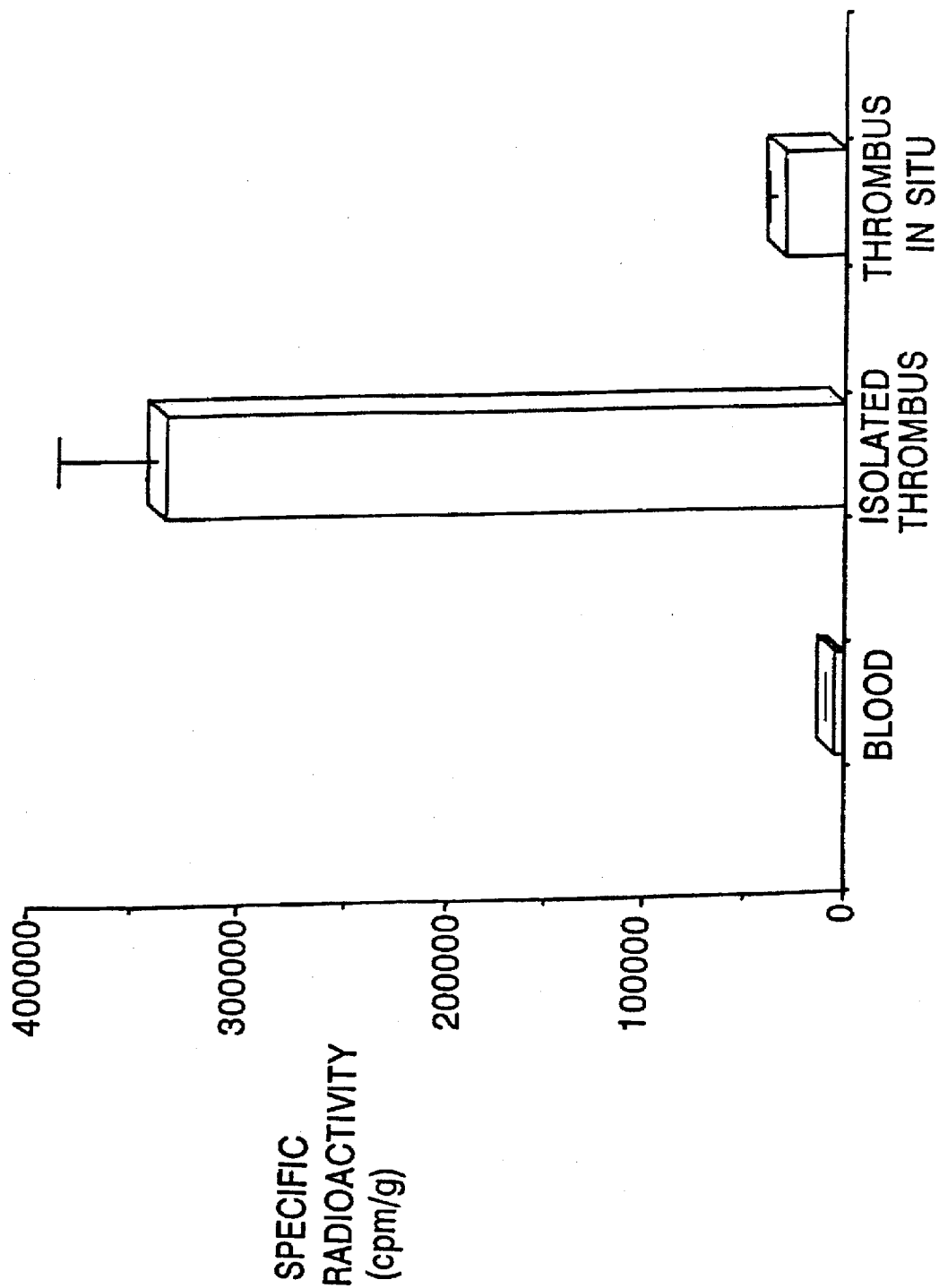

FIG. 16. Uptake of labeled r31 kD FBD by stainless steel coil-induced venous thrombi The bars and vertical brackets represent the mean ± SEM (N=10) of the specific radioactivity associated with isolated thrombi, vein segments carrying the thrombus ("thrombi in-situ"), or peripheral blood samples 24 h after administration of 125I-31 kD FBD. For details, see Example 7, Section A.

Figure 17:
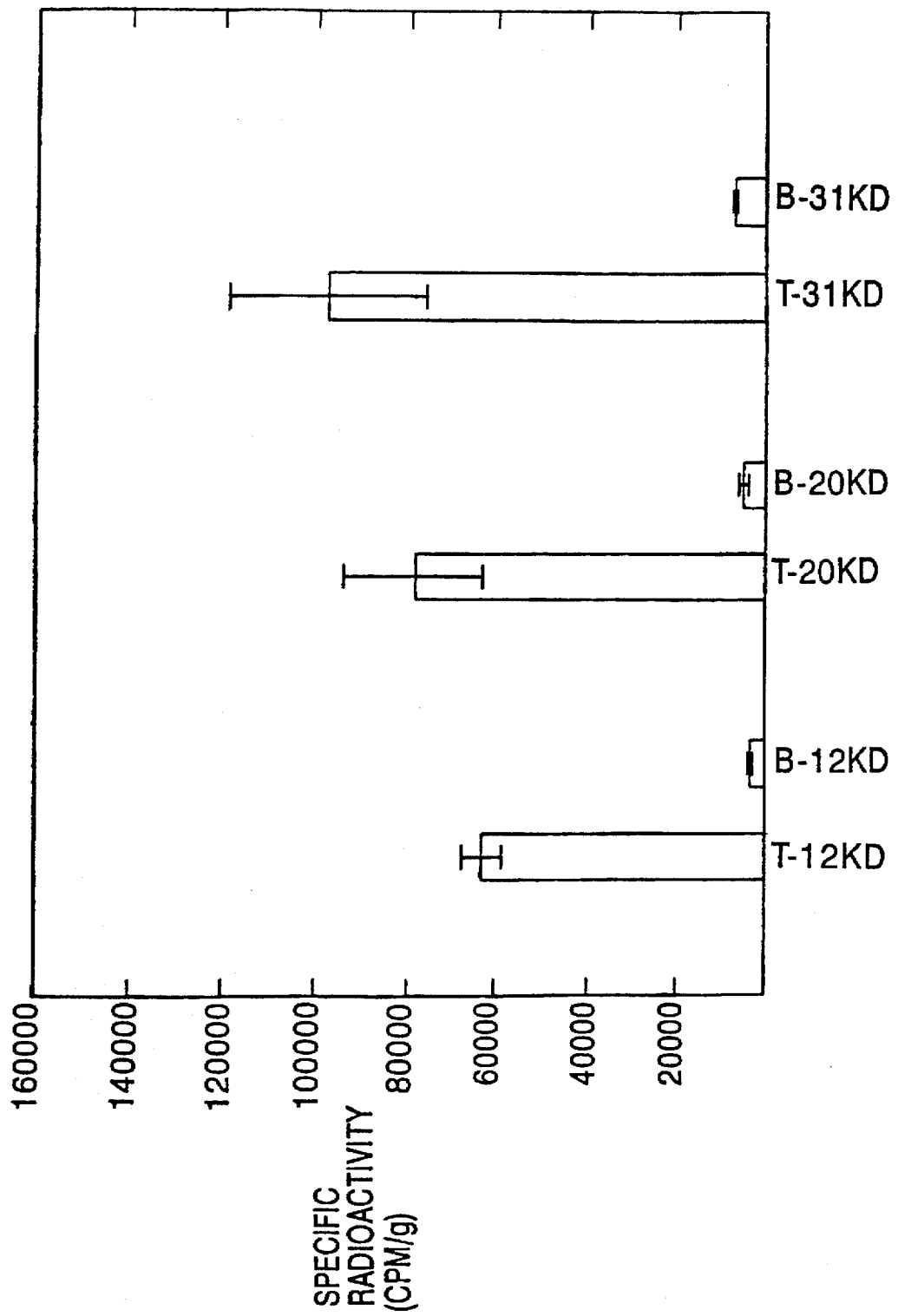

FIG. 17. Comparison of labeled r12 kD, r20 kD and r31 kD FBD polyeptides in the rat venous thrombus model The bars and vertical brackets represent the mean ±SEM (N=5) of the specific radioactivity associated with isolated thrombi (T) or blood (B) 24 hours after administration of the 125I-labeled recombinant polypeptides, as indicated. For details, see Example 7, Section B.

Figure 18:
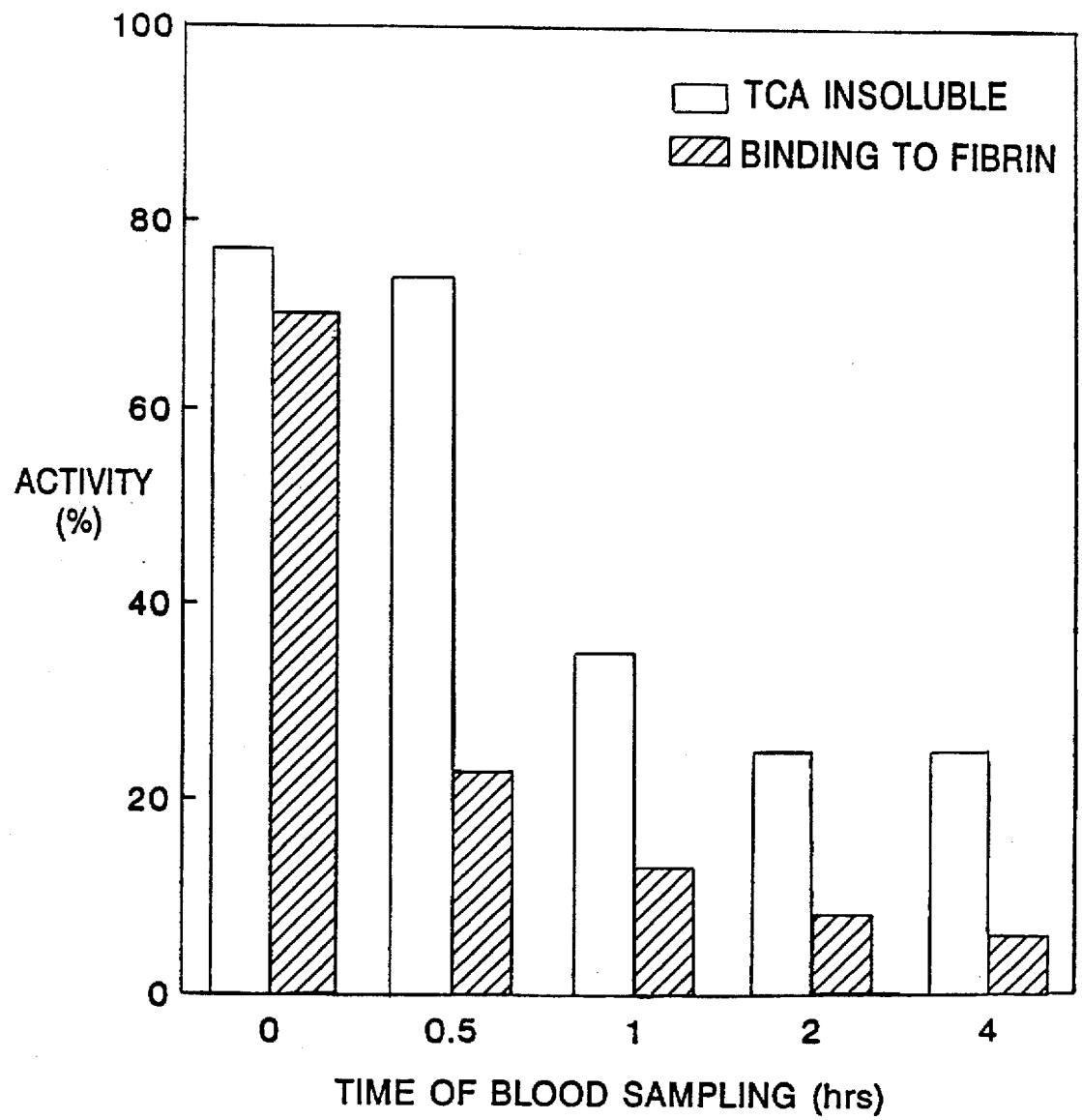

FIG. 18. Metabolic stability of $^{125}$I-labeled r31kD FBD in rats

Rats were injected intravenously with $^{125}$I-r31 kD FBD ($5\times10^6$ cpm/rat) in a similar experiment to that described in FIG. 7. At the time intervals indicated blood samples were removed, placed in sodium citrate-containing tubes (final sodium-citrate concentration =0.38%) and resulting blood aliquots were directed as follows: either (a) treated with 20% TCA and the TCA insoluble counts (after TCA precipitation) were measured; or (b) incubated with preformed clot (using 20 µl whole blood from control rat); binding of the 125I-31 kD FBD to the preformed clot was measured under the conditions of the two-step reaction II (Example 6). The radioactivity was measured by a gamma counter and the activity of each sample was calculated as a percentage of total cpm present in the reaction mixture. (Normally TCA precipitation includes placing sample aliquots on filters which are counted for total cpm, washing the filter 3 times with 20% TCA followed by twice with 20% ethanol to extract the TCA, and recounting filters for TCA insoluble counts whereby the percentage of TCA-insoluble counts can be calculated.)

Figure 19:
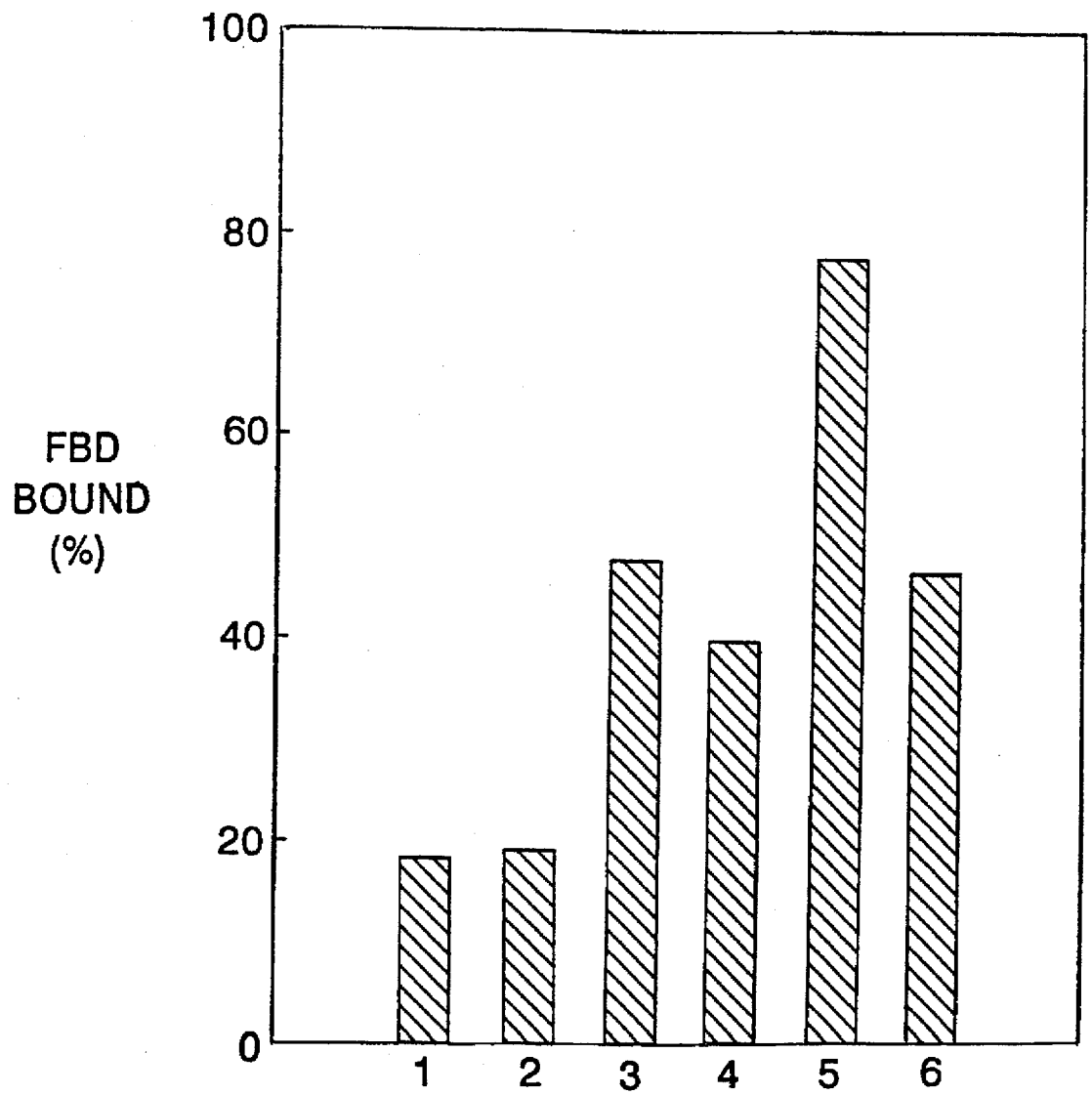

FIG. 19. Binding of fibrin binding domain polypeptides to the fibrin clot

This experiment was carried out essentially as described for the two-step Reaction II (Example 6). 0.15 µM $^{125}$-I of one of the fibrin binding domain polypeptides as indicated below was incubated at 37° C. with preformed fibrin clot derived from 20 µl citrated whole blood. The binding was measured in the presence of 5 mM $CaCl_2$ and 0.02 units/ml transglutaminase. The reaction was terminated, after a 45 minute incubation, by centrifugation; the pellet was washed three times with PBS and the radioactivity was measured in a gamma counter.

1. plasmatic 31 kD FBD (p31 kD)
2. r12 kD
3. r20 kD
4. r31 kD (Batch A)
5. r31 kD ( Batch B )
6. r31 kD (Batch C)

Figure 20:
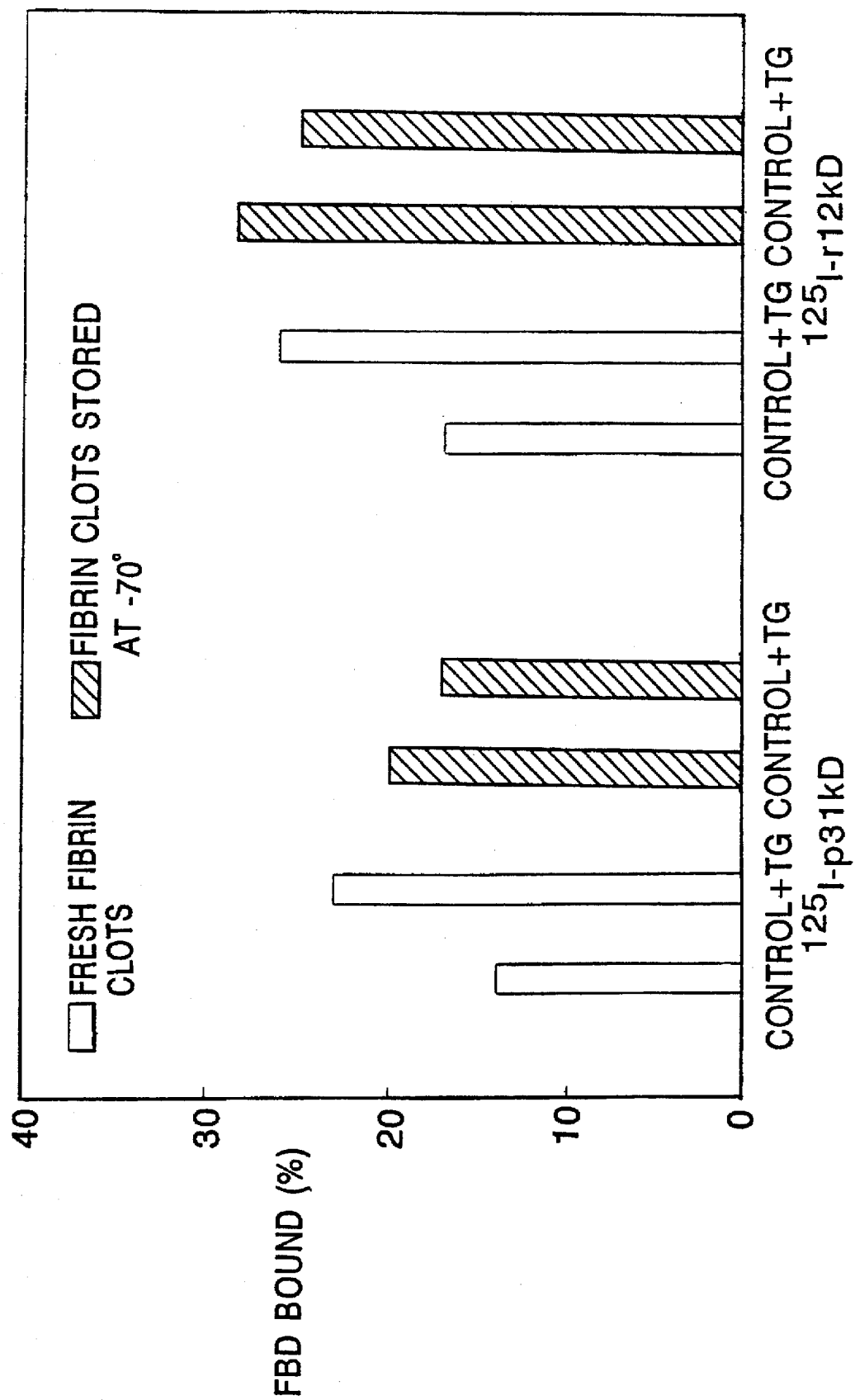

FIG. 20. Comparison of binding of $^{125}$I-r12 kD to fresh and frozen fibrin clots This experiment was carried out essentially as described for the two-step Reaction II (Example 6). Preformed fibrin clots derived from 20 µl citrated whole human blood were either frozen at −70° C. for 7 days (frozen clots) or used immediately after their formation (fresh clots).

The fibrin clots were incubated with 0.15 μM $^{125}$I-r12 kD in the presence or absence of 0.02 units/ml guinea-pig liver transglutaminase (Sigma). The binding to fibrin clots was measured as described in Example 6.

FIG. 21A-1 to 21F-2. Refoldding and purification of the r20 kD polypeptide as monitored by elution profiles from a Superose 12 column (attached to a FPLC)

Figures 1, 21A:
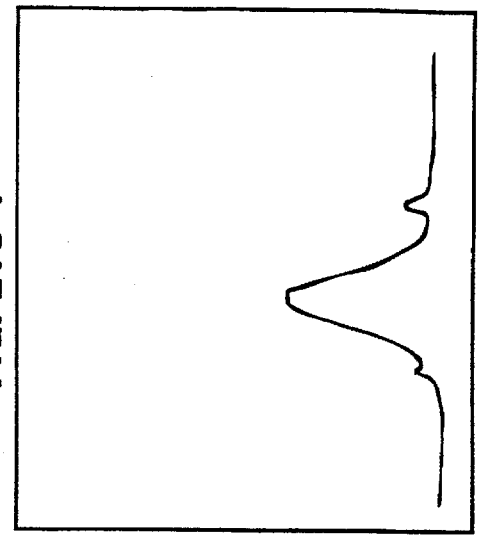
Figures 2, 21A:
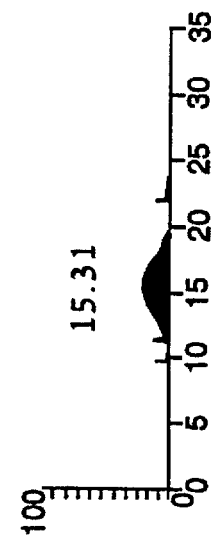
Figures 1, 21B:
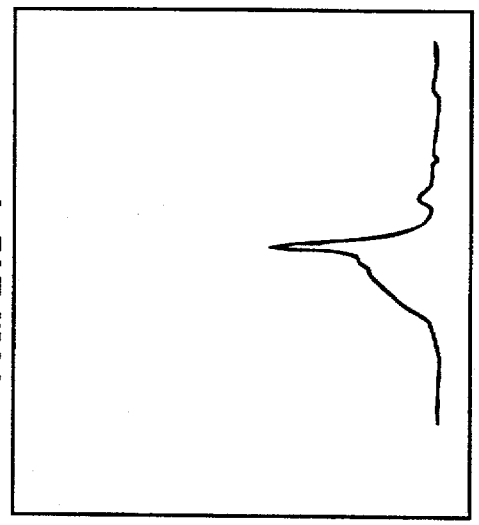
Figures 2, 21B:
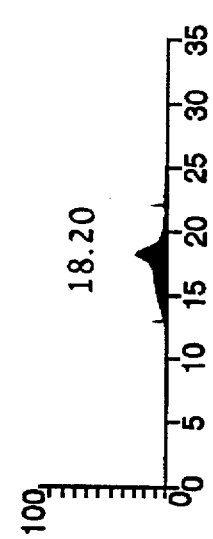
Figures 1, 21C:
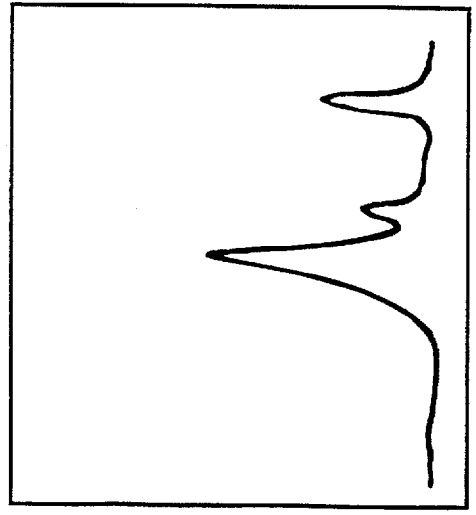
Figures 2, 21C:
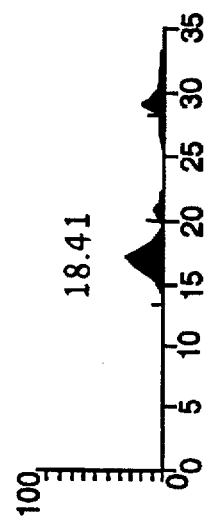

Aliquots of 200 μl of the r20 kD polypeptide at various stages of the refolding and purification process were injected on top of a Superose 12 column (attached to a FPLC). The column was equilibrated and eluted with a solution of 150 mM NaCl/20 mM Tris HCl, pH 7.8, at a flow rate of 0.8 ml/min. The lower trace is obtained from the FPLC Controller LCC-500. FIGS. 21A-1 and 21A-2. Pellet of r20 kD polypeptide solubilized in 6M Guanidine-HCl and reduced with 50 mM β-mercaptoethanol; FIGS. 21B-1 and 21B-2. Refolded and air-reoxidized r20 kD polypeptide; FIGS. 21C-1 and 21C-2. Q-Sepharose bound polypeptides, i.e., material which was separated from the purified r20 kD; FIGS. 21D-1 and 21D-2. Flow-through from the Q-Sepharose column; FIGS. 21B-1 and 21E-2. Flow-through from the Heparin-Sepharose column, i.e., material which was separated from the purified r20 kD; FIGS 21F-1 and 21F-2. Purified 20 kD polypeptide (retention time =18.16 min), eluted from the Heparin-Sepharose column with 0.5 M NaCl. Note that there is no peak at this retention time of 18.16 min in Profile A, where the material is in reduced form, nor in Profiles C & E, which contain incorrectly folded forms of the 20 kD polypeptide.

FIG. 22A–22E. Refolding and purification of the r12 kD polypeptide as monitored bvelution profiles from a Superose 12 column (attached to a Waters HPLC system)

Figure 22A:
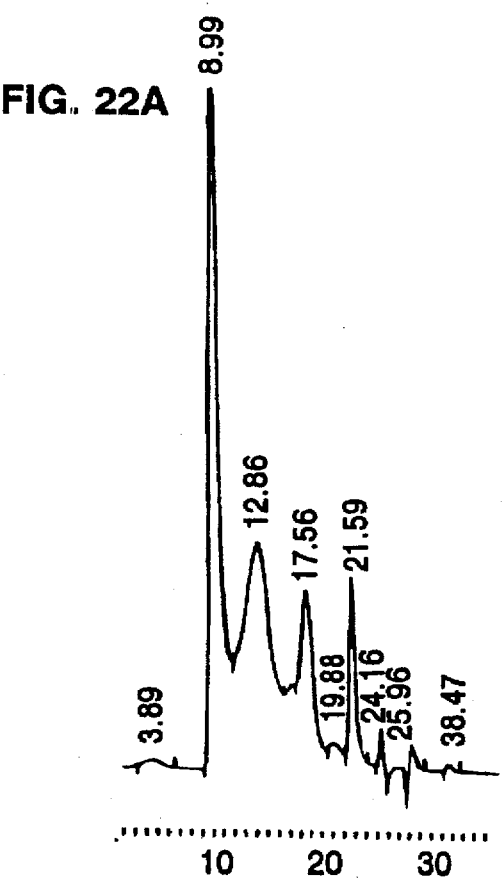
Figure 22B:
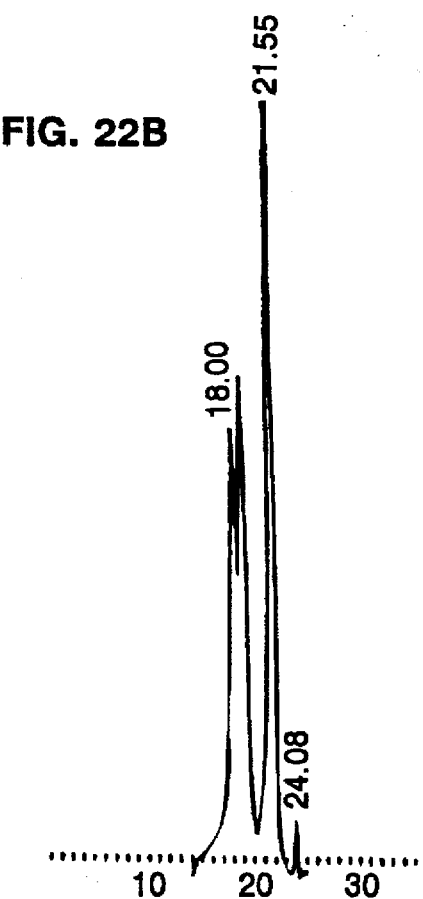
Figure 22C:
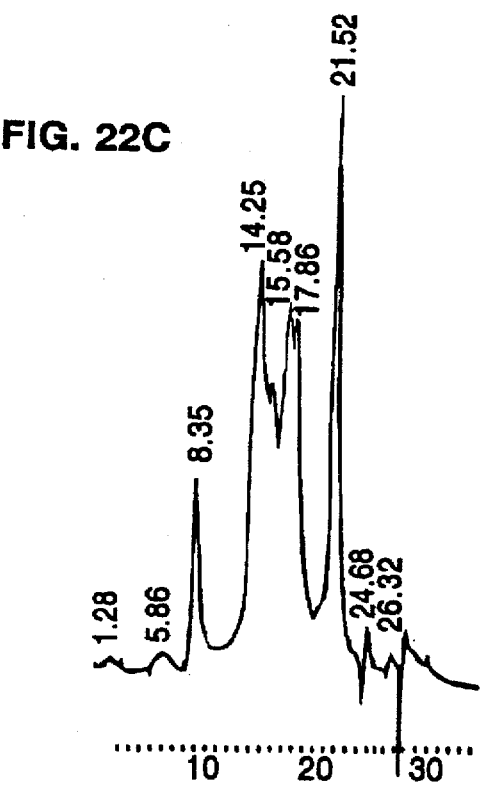
Figure 22D:
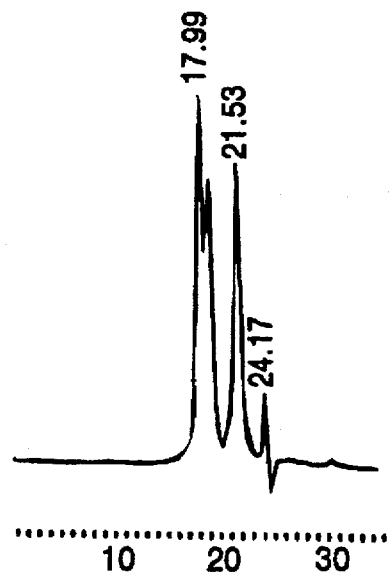
Figure 22E:
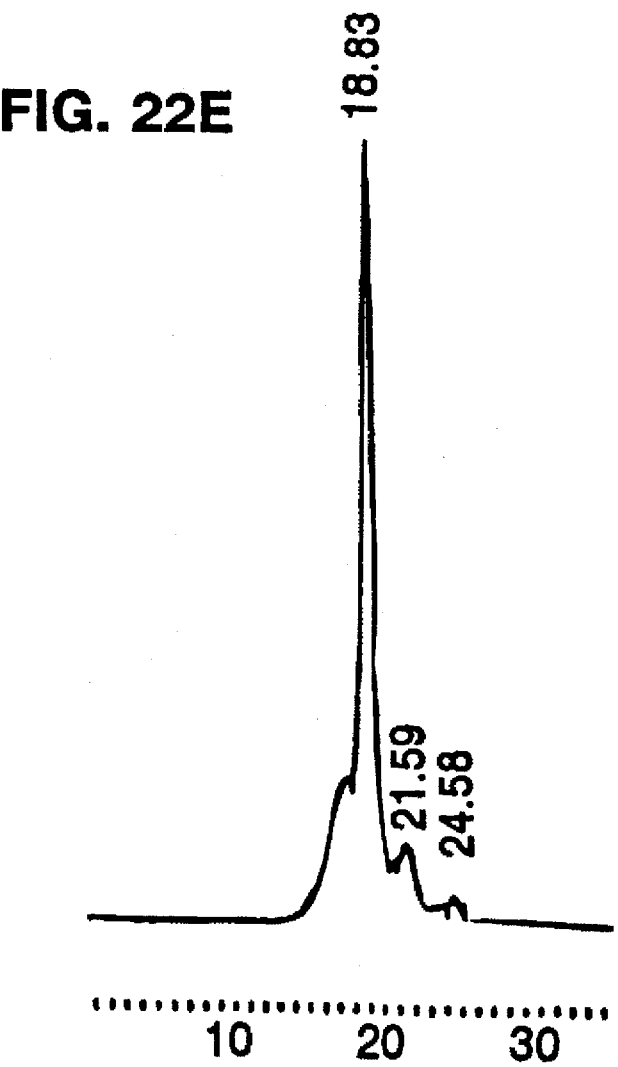

Aliquots of 25–100 μl of the r12 kD polypeptide at various stages of the refolding and purification process were injected on top of a Superose 12 column (attached to a Waters HPLC system). The columnwas equilibrated and eluted with a solution of 150mMNaCl/20mMTris HCl, pH 7.8, at a flow rate of 0.8 ml/min. FIG. 22A. Pellet of r12 kD polypeptide solubilized in 6 M Guanidine-HCl and reduced with 50 mM βmercaptoethanol; FIG. 22B. Refolded and air-reoxidized r12 kD polypeptide; FIG. 22C. Q-Sepharose bound polypeptides, i.e., material which was separated from the purified r12 kD; FIG. 21D. Flow-through from both the Q- and Heparin-Sepharose columns (in this case, the columns were connected in series and the flow-through from the Q-Sepharose was therefore automatically loaded on the Heparin-Sepharose column), i.e., material which was separated from the purified r12 kD; FIG. 22E. Purified r12 kD polypeptide (retention time—18.83 min), eluted from the Heparin-Sepharose column with 0.5M NaCl. Note that there is no peak at this retention time of 18.83 min in Profile A, where the material is in reduced form, nor in Profiles C & D, which contain incorrectly folded forms of the r12 kD polypeptide.

Figure 23:
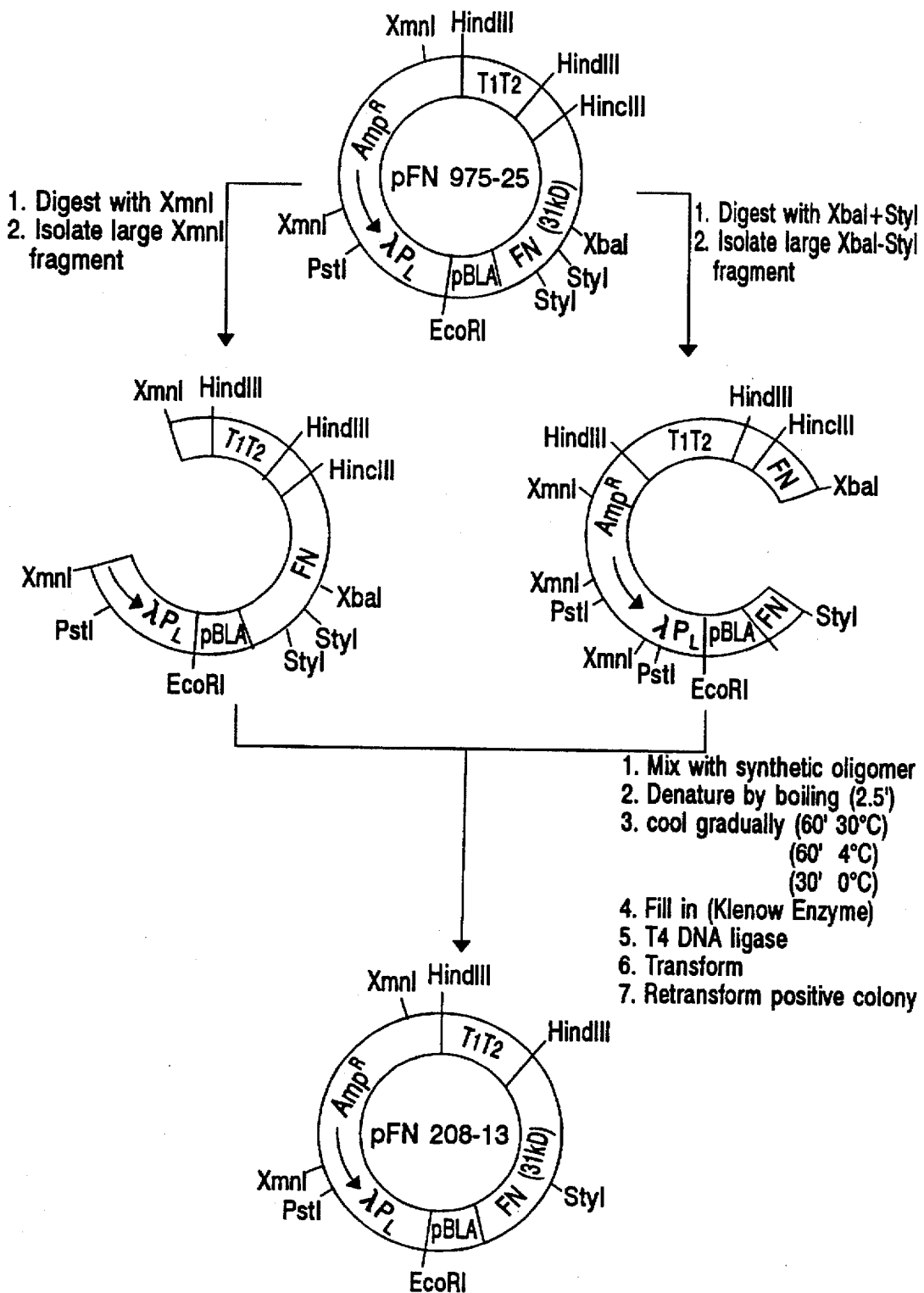

FIG. 23. Construction of plasmid pFN 208-13

Two aliquots of plasmid pFN 975-25 (ATCC No. 67832) were separately digested with XmnI and XbaI-StyI respectively. The large fragments were isolated from each digest and mixed together with the synthetic oligomer shown in FIG. 8. The mixture was then boiled for 2.5 minutes, cooled gradually for 60 minutes at 30° C., followed by 60 minutes at 4° C., and finally 30 minutes at 0° C. The now reannealed DNA was then filled in by Klenow fragment and ligated with T4 DNA ligase. The DNA was transformed into *E.coli* A1645 and transformants were screened for a clone positive for the oligomer. The plasmid from a positive clone was designated pFN 208-13, and deposited in the ATCC in a host *E.coli* A4255 as Accession No. 68456. This plasmid expresses an 18.5 kD FBD polypeptide of the amino terminal end of the molecule under control of the λ $P_L$ promotor and the β-lactamase ribosomal binding site.

FIG. 24 (SEQ ID NO. 39). Synthetic Linker Used in construction of Plasmid pFN 208-13

This figure shows the synthetic oligomer used in construction of plasmid pFN 208-13 (FIG. 23).

Figure 25:
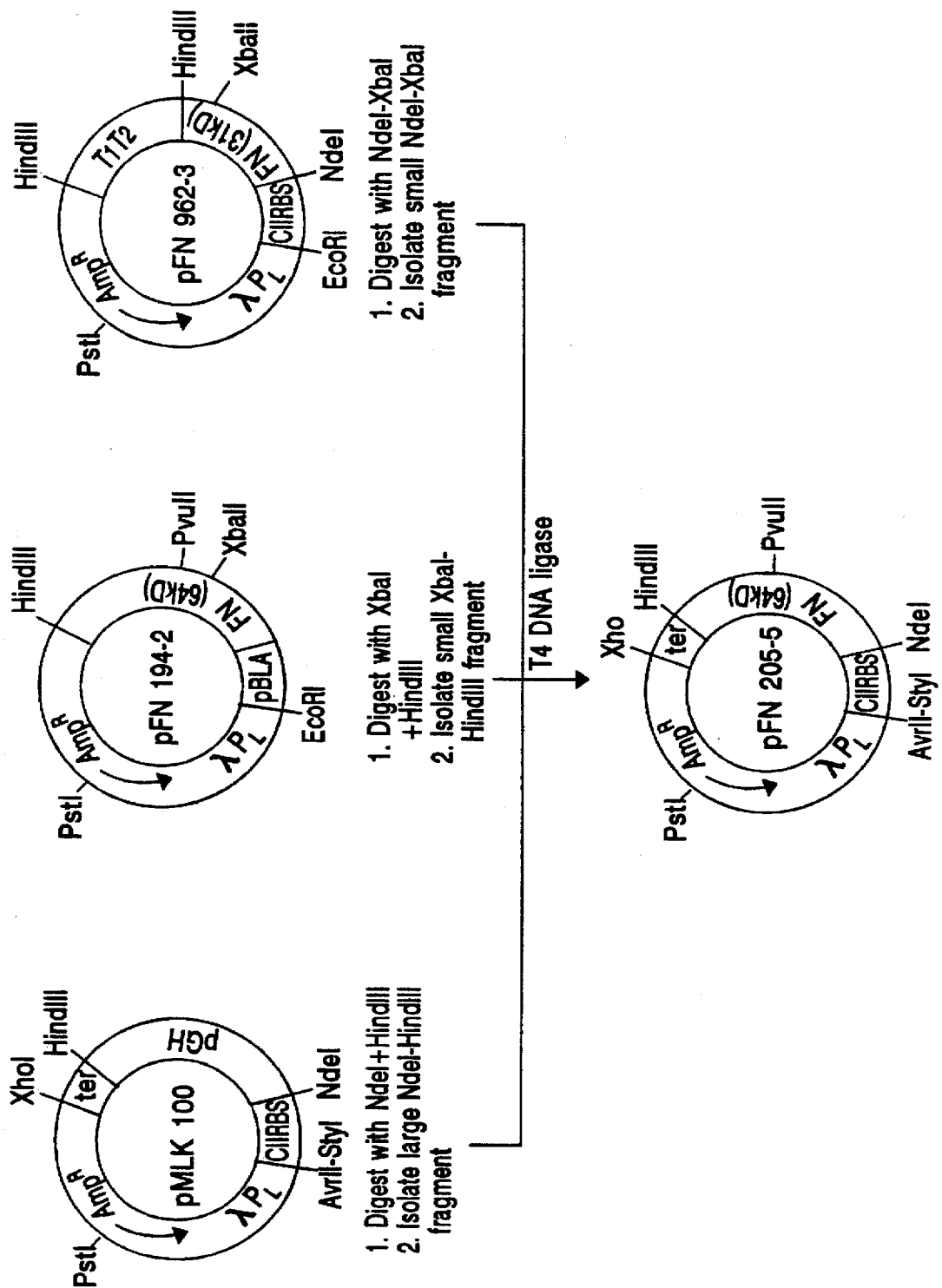

FIG. 25. Construction of plasmid pFN 205-5

The small fragment was isolated from the digestion of plasmid pFN 194-2 (FIG. 14) by XbaI-HindIII. The small fragment was isolated from NdeI-HindIII digestion of plasmid pFN 962-3 (disclosed in coassigned patent application PCT/US89/05875 and published as international publication no. WO/90/07577 on Jul. 12, 1990, FIGS. 45–49 and the description of the figures). These two fragments were then ligated with the large fragment isolated from the NdeI-HindIII digest of plasmid pMLK-100 (ATCC Accession No. 68605). The resulting plasmid designated 205-5 is a high expressor of a 64 kD polypeptide containing the 31 kD FBD fused to the 33 kD CBD under control of the $AP_E$ promotor, CII ribosomal binding site and containing the trp transcription terminator designated "ter" immediately downstream of the structural gene. This polypeptide has been purified and refolded essentially as described for a 31 kD FBD polypeptide disclosed in the above-referenced PCT publication.

Figure 26:
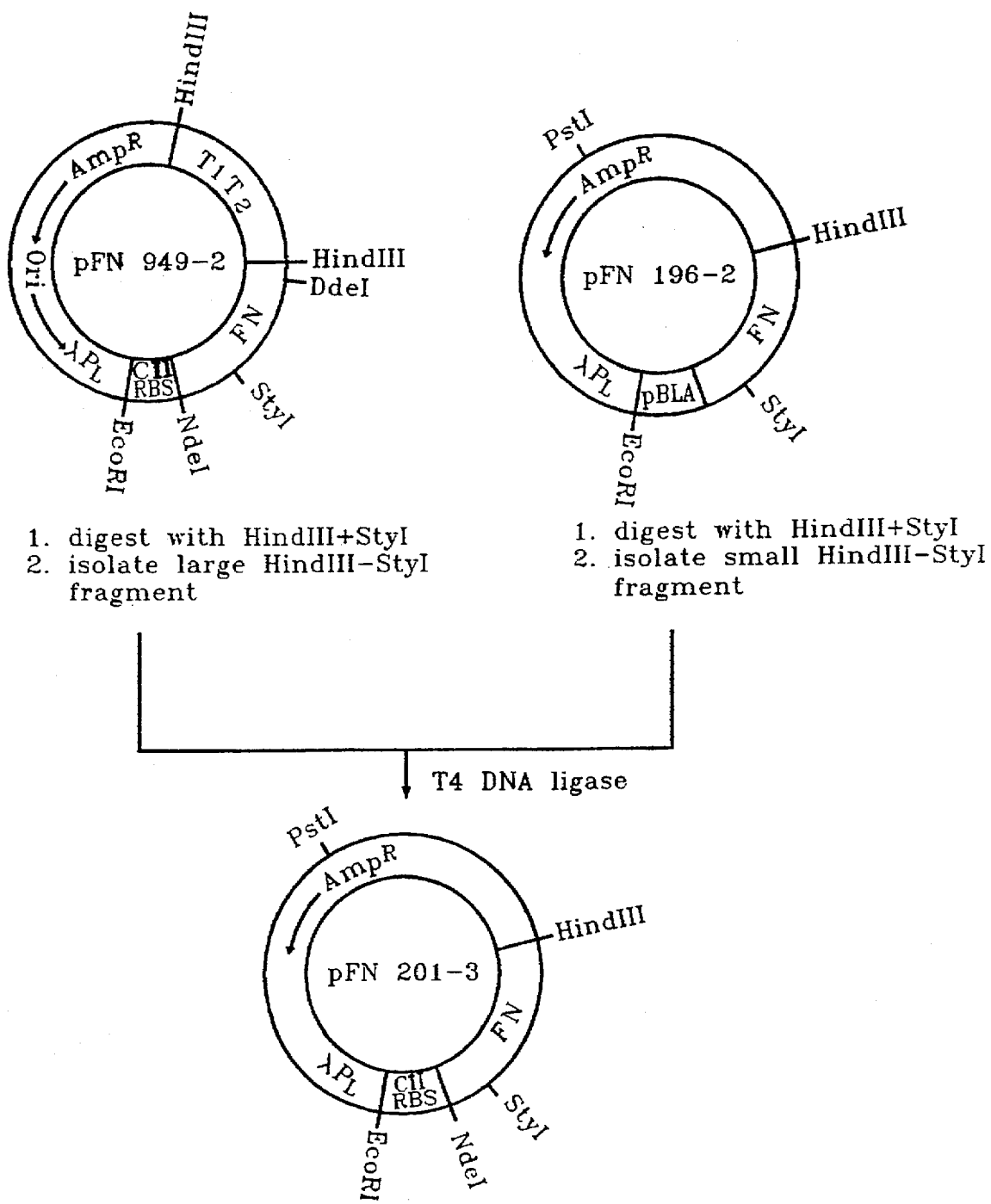

FIG. 26. Construction of Plasmid pFN 201-3

The large fragment was isolated from the HindIII-StyI digest of plasmid pFN 949-2 (ATCC Accession No. 67831), and ligated with the small fragment isolated from the HindIII-StyI digest of plasmid pFN 196-2 (ATCC Accession No. 68328). The resulting plasmid designated pFN 201-3 expresses the 12 kD FBD polypeptide under control of the $\lambda P_L$ promotor and CII ribosomal binding site.

Figure 27:
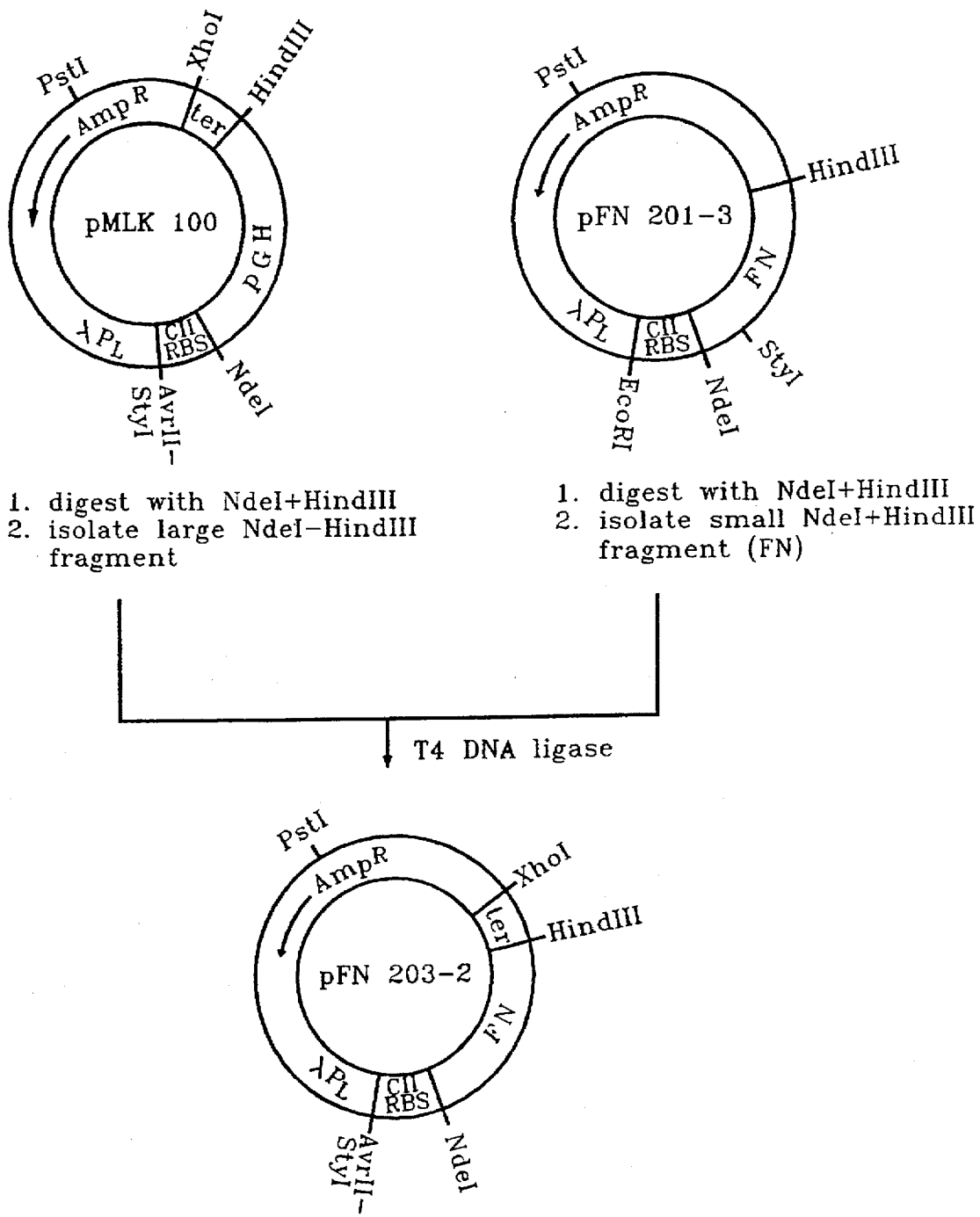

FIG. 27. Construction of plasmid pFN 203-2

The large fragment was isolated from the NdeI-HindIII digest of plasmid pMLK-100 (deposited in *E.coli* 4300 under ATCC Accession No. 68605) and ligated with the small fragment isolated from the NdeI-HindIII digest of plasmid pFN 201-3. The resulting plasmid designated pFN 203-2 which expresses the 12 kD FBD polypeptide under control of the λ $P_L$ promotor, $C_{II}$ ribosomal binding site and trp transcription termination sequence designated "ter" was deposited in ATCC in *E.coli* A4255 under ATCC Accession No. 68606. Plasmid pFN 203-2 is also known as pFN 203-2-3.

Figure 28:
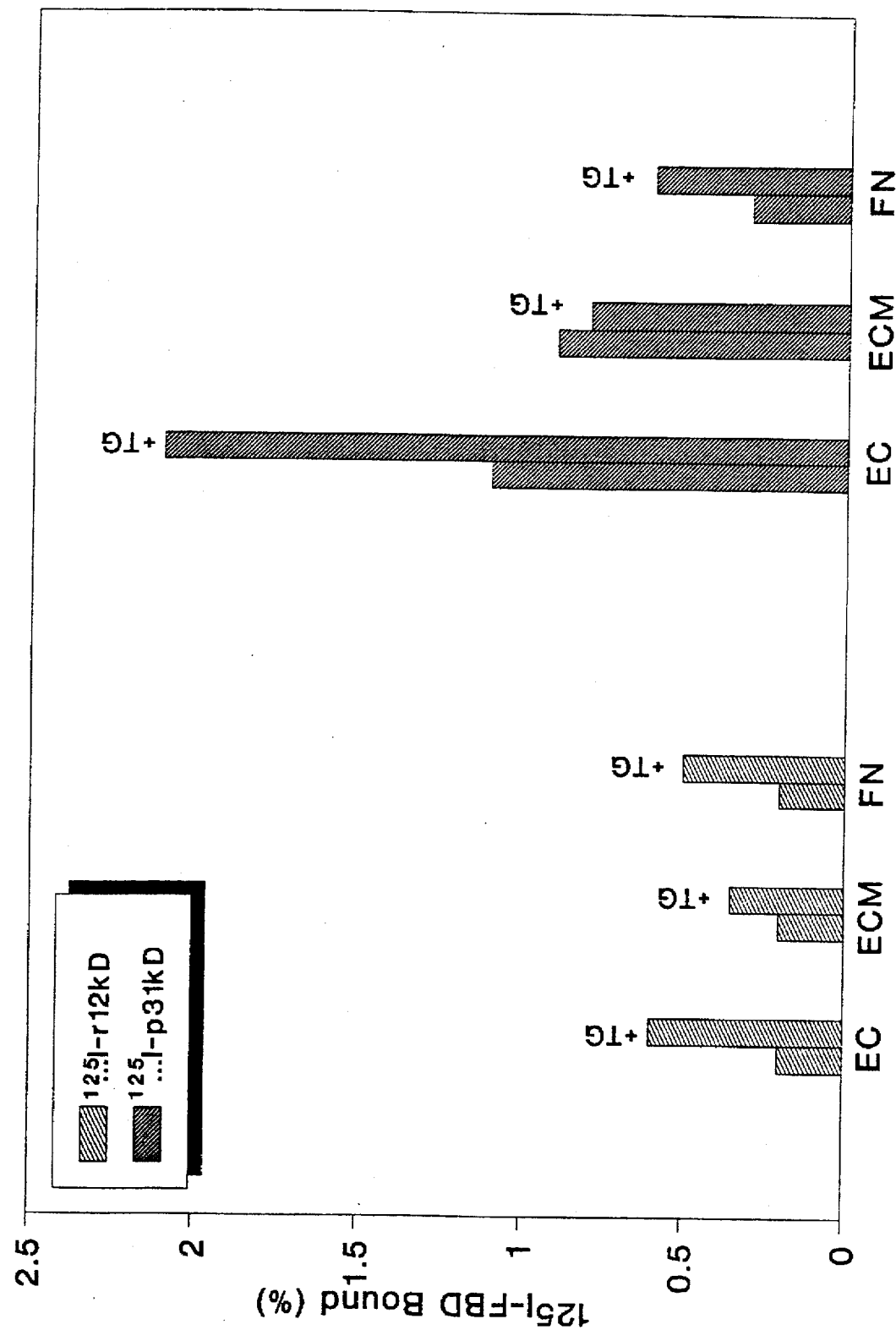

FIG. 28. Binding of FBD polypeptide Fragments to Vascular Components

This figure shows the low degree of binding of the 12 kD polypeptide to vascular components such as endothelial cells, extracellular matrix, and immobilized fibronectin by comparison with the 31 kD as described in Example 9. The binding of the 12 kD was increased but still remained relatively low in comparison to the 31 kD even with the addition of exogenous transglutaminase.

Figure 29:
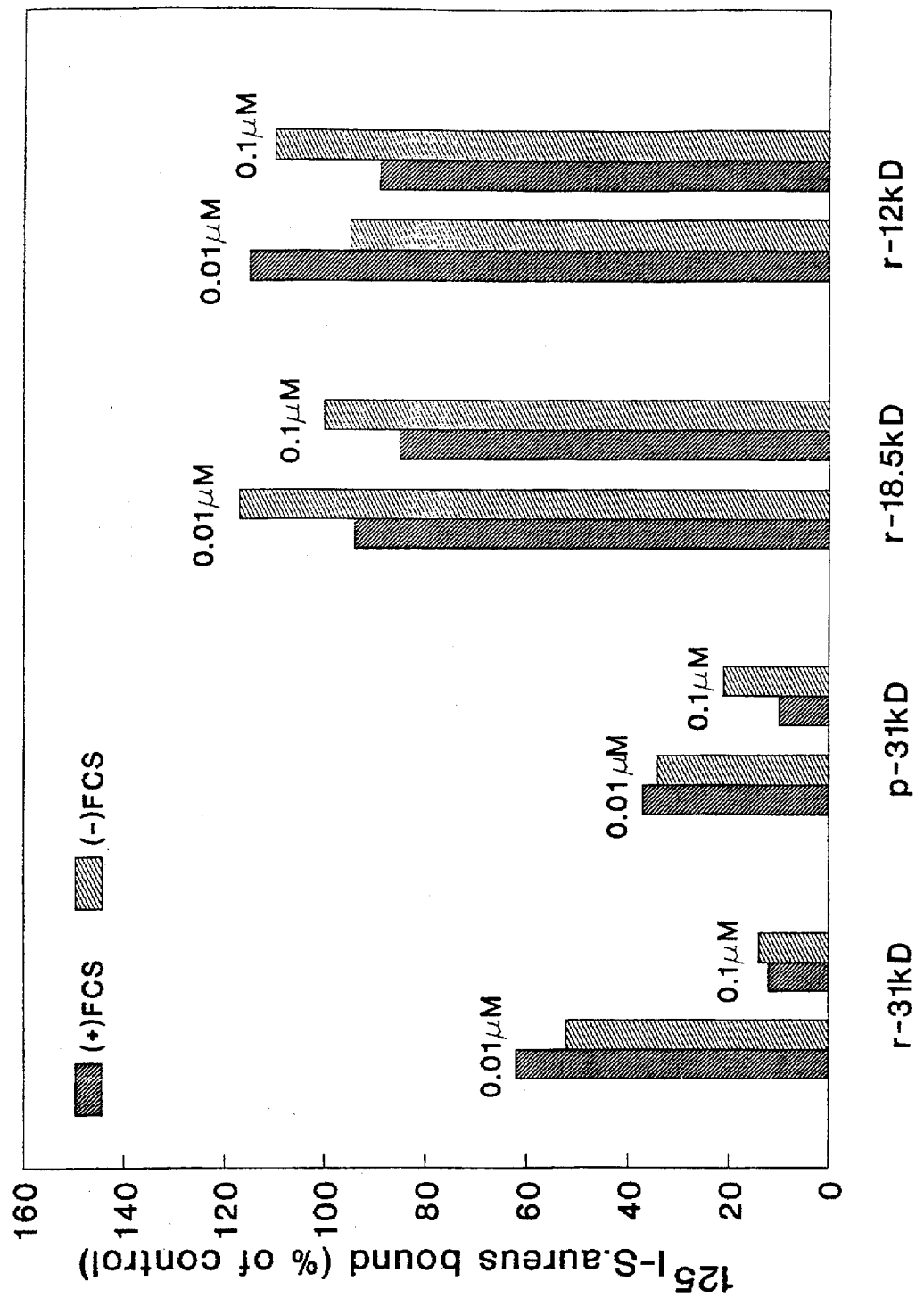

FIG. 29. Effect of Various FBD Polypeptide Fragments on the Binding of *S. aureus* to Endothelial Cells (EC)

Preparation of labelled *S. aureus* and the endothelial cell (EC) binding assay are described in Example 9. The inhibitory effect of plasmatic and recombinant 31 kD, recombinant 18.5 kD, and recombinant 12 kD on binding of *S. aureus* to EC were tested.

This figure shows the dose effect of different FBD polypeptides on binding of *S. aureus* to endothelial cells at 4° C. in the presence or absence of fetal calf serum (FCS). (Previous experiments showed a dramatic increase of 2-3 fold in binding of *S. aureus* to EC in the presence of FCS at 37° C., but only a slight increase at 4° C. The increase is probably due to the presence of plasma fibronectin in FCS.) In the present experiment performed at 4° C, there is no significant effect of added FCS on the binding. Both the plasmatic and recombinant 31 kD show a strong dose dependent inhibition of binding, while the recombinant 18.5 kD and 12 kD polypeptide fragments caused virtually no inhibition of binding indicating they have little or no *S. aureus* binding affinity.

Figure 30:
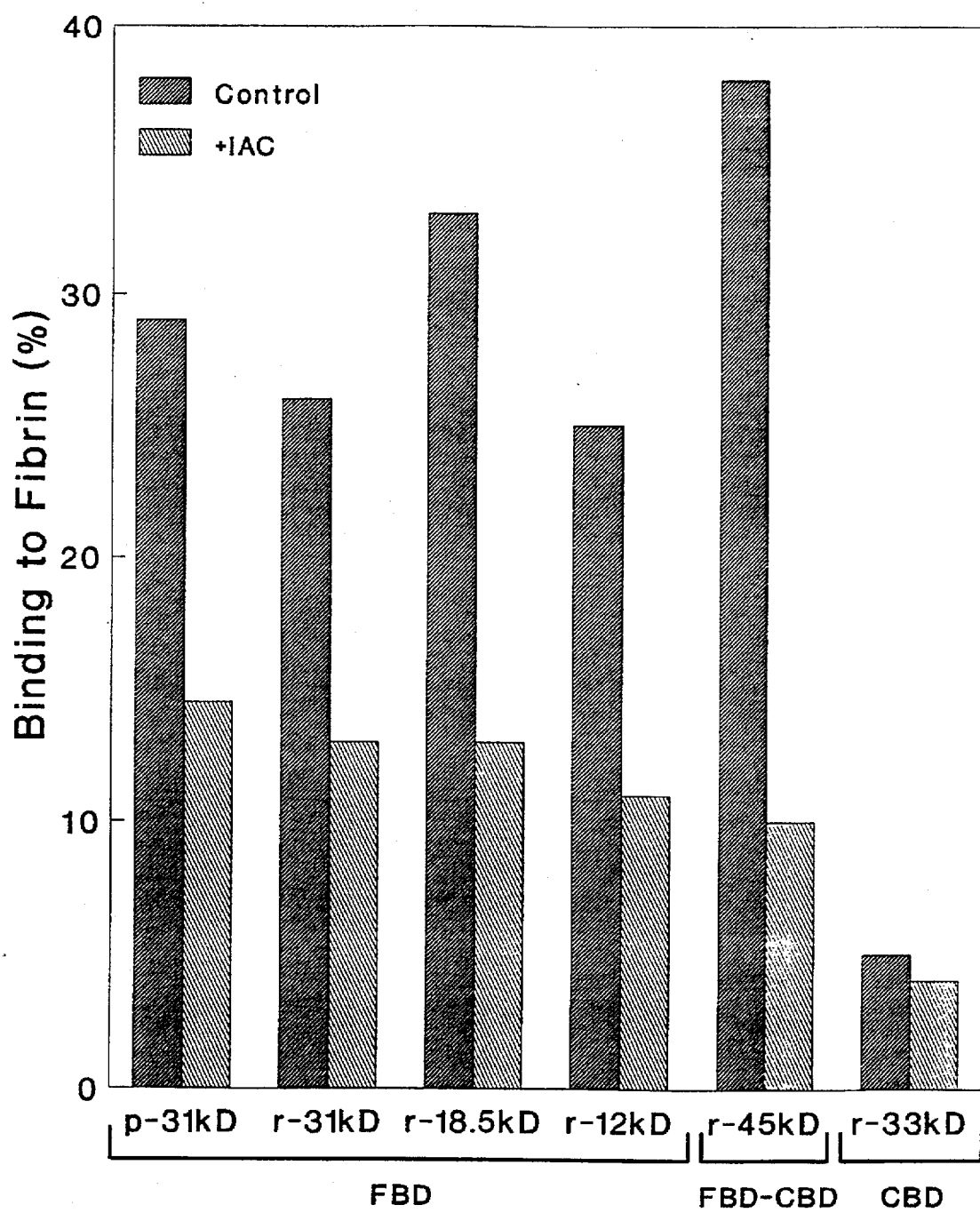

FIG. 30. Binding of Different FBD polypeptide Fragments to Preformed Fibrin Clot (Reaction II)

This figure shows the specificity of different FBD polypeptides to a preformed fibrin clot as described in Example 9. The FBD polypeptides tested were the 31 kD, 20 kD, 18.5 kD and 12 kD. Additionally, a 45 kD fusion polypeptide of the 12 kD FBD fragment fused to the 33 kD CBD (Example 40) was tested. A 33 kD CBD polypeptide (coassigned PCT Publication No. WO/90/07577, pages 62-64) was included as a control. All of the FBD polypeptides tested, including the 45 kD fusion polypeptide, bound to a preformed fibrin clot in similar proportions (25–38% bound). The 33 kD CBD alone bound to the clot in a small proportion only. The transglutaminase inhibitor iodoacetate (IAC) inhibited binding by 50–75% indicating that transglutaminase is an active component of the binding reaction. The binding of the 33 kD CBD polypeptide was not appreciably affected by iodoacetate indicating that it binds by a different mechanism.

Figure 31:
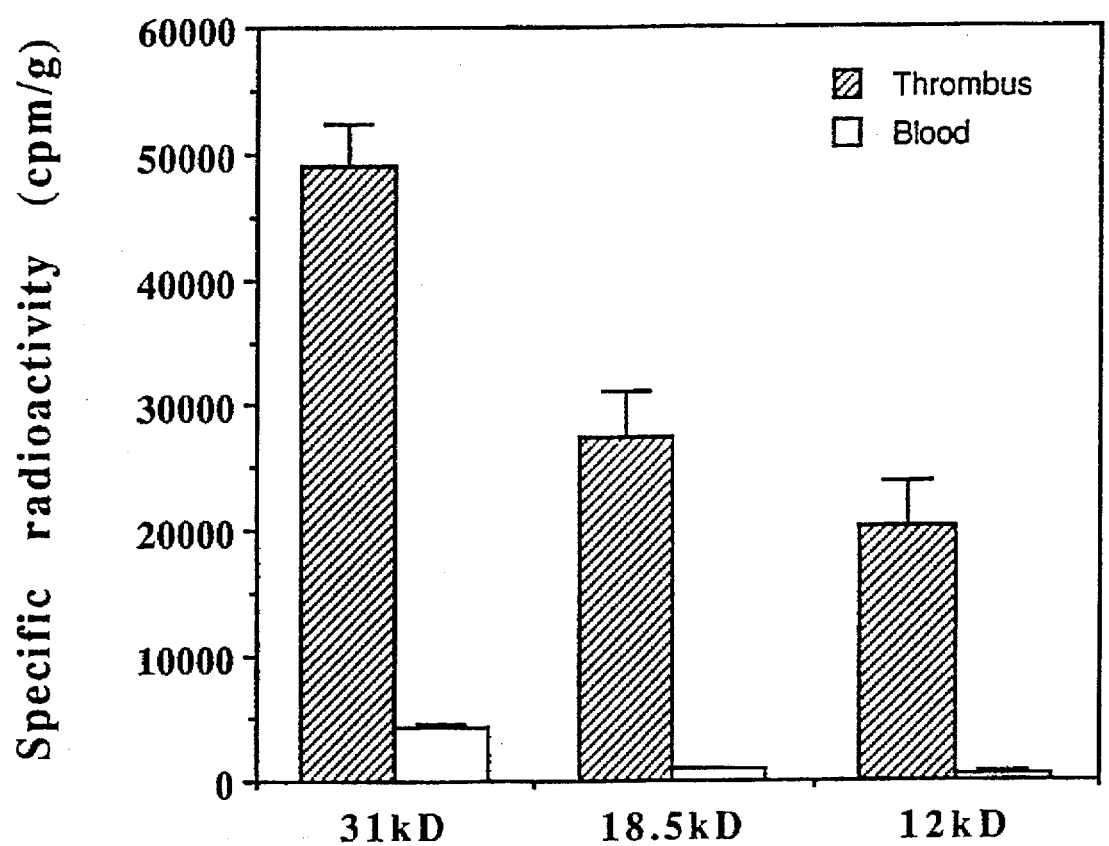

FIG. 31. In vivo thrombi labeling using the 12 kD and 18.5 kD FBD polypeptide fragments is described in Example 13. The figure shows the results as specific radioactivity of thrombus (hatched bars) and blood (open bars) of stainless-steel coil-bearing rats, 24 h after intravenous administration of $^{111}$In-labelled recombinant FBD proteins. The bars and vertical brackets represent the means and SEM of cpm/g wet weight respectively. The thrombus: blood ratios are shown in FIG. 32.

Figure 32:
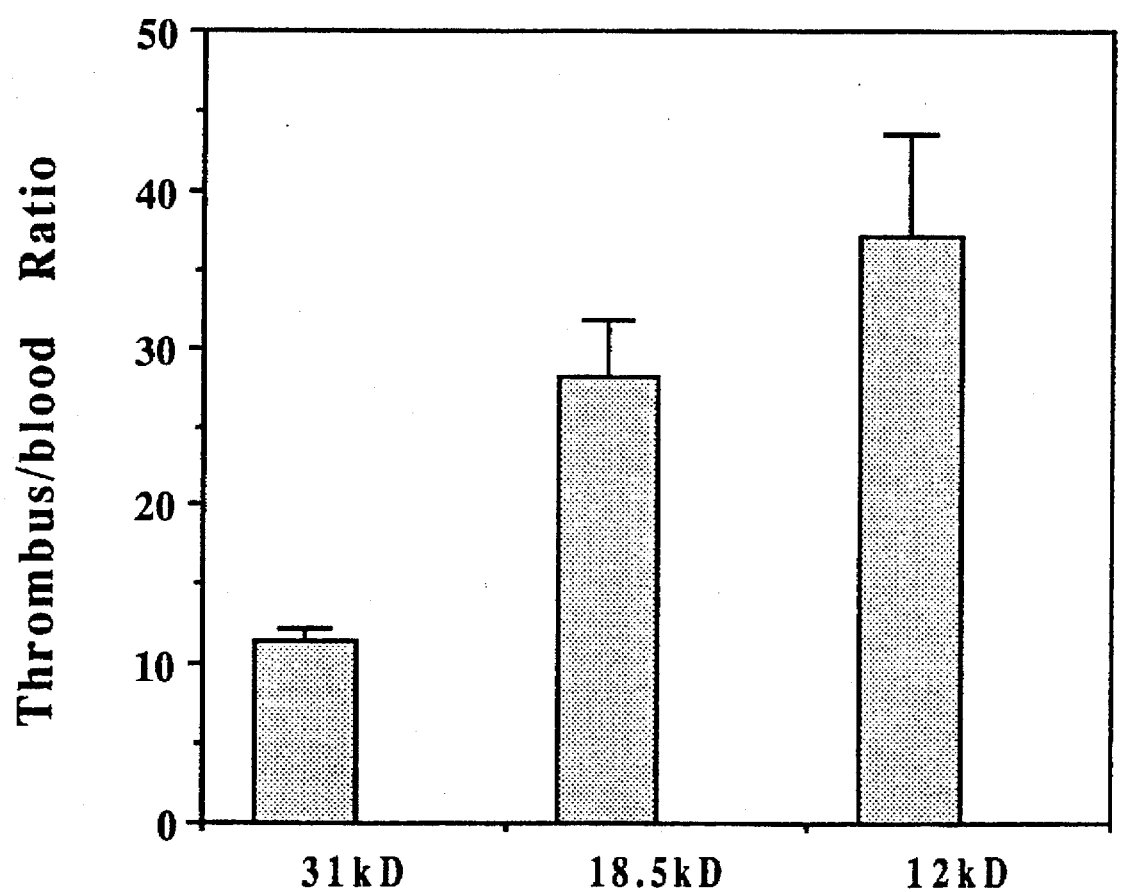

FIG. 32. Thrombus to blood ratios of specific radioactivity 2 h after administration of Illin-labelled 12 kD-, 18.5 kD- and 31 kD-FBD in the rat coil model described in FIG. 31.

Figure 33:
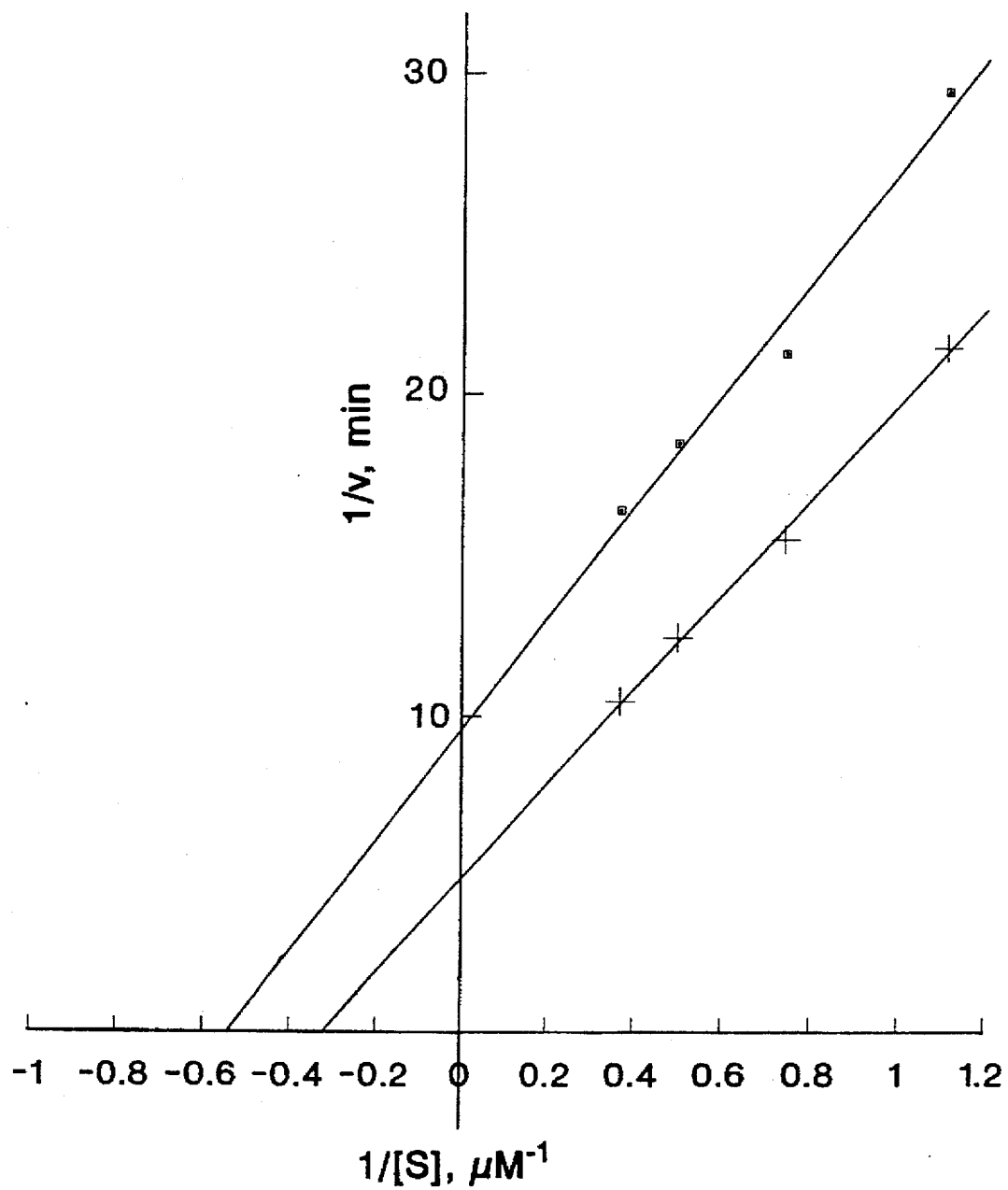

FIG. 33. Lineweaver-Burk plots for human Glu-Plasminogen activation kinetics, at pH 7 4 and 37° C using either SK or the FBD-SK complex as activators. In a 200 µl volume, in 96-well plates, the plasminogen substrate concentration varied between $0.9 \times 10^6$ and $2.7 \times 10^6$M. The S-2251 substrate (H-D-Val-Leu-Lys-pNA) (SEQ ID NO. 5) final concentration was $5 \times 10^4$M and the final activator concentration was $2 \times 10^9$M. The rate of reaction, v, represents the change in absorbance at 405 nm, $\Delta A$ (absorbance units), per time $\Delta t$ (min).

Figure 34:
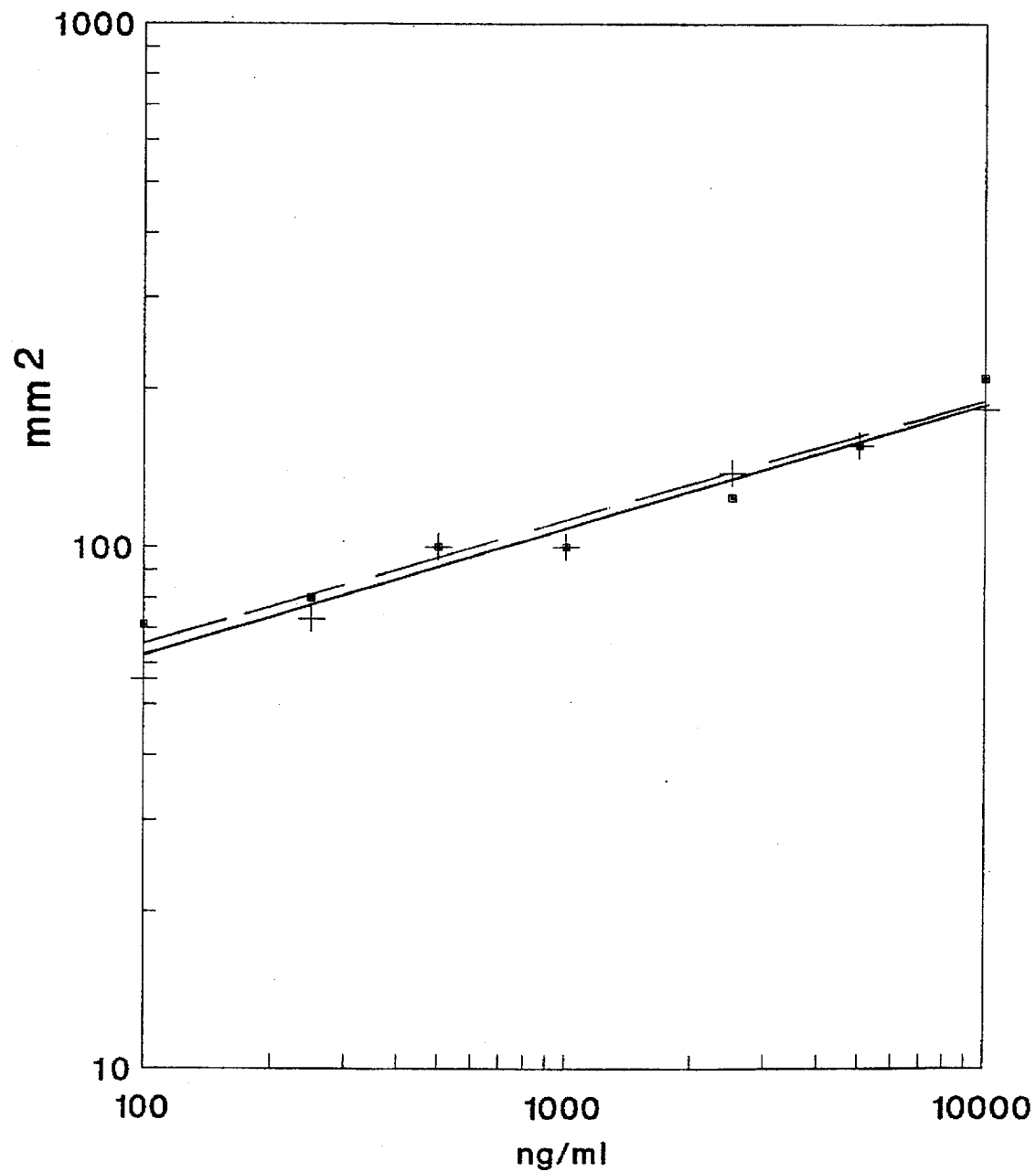

FIG. 34. Fibrin-agar plates were prepared by mixing 5 ml (2mg/ml) fibrinogen, 5 ml (0.4%) Noble-agar, 0.5 ml (1M) $CaCl_2$ and 0.5 ml (10u/ml) thrombin, all in imidazole-buffered saline pH 7.4. After polymerization small wells were made using Pasteur pipettes and vacuum, into which aliquots of SK or FBD-SK complex, at concentrations between $10^2$–$10^4$ng/ml, were added. After incubation at 37° C. overnight the lysis zone was measured.

Figure 35:
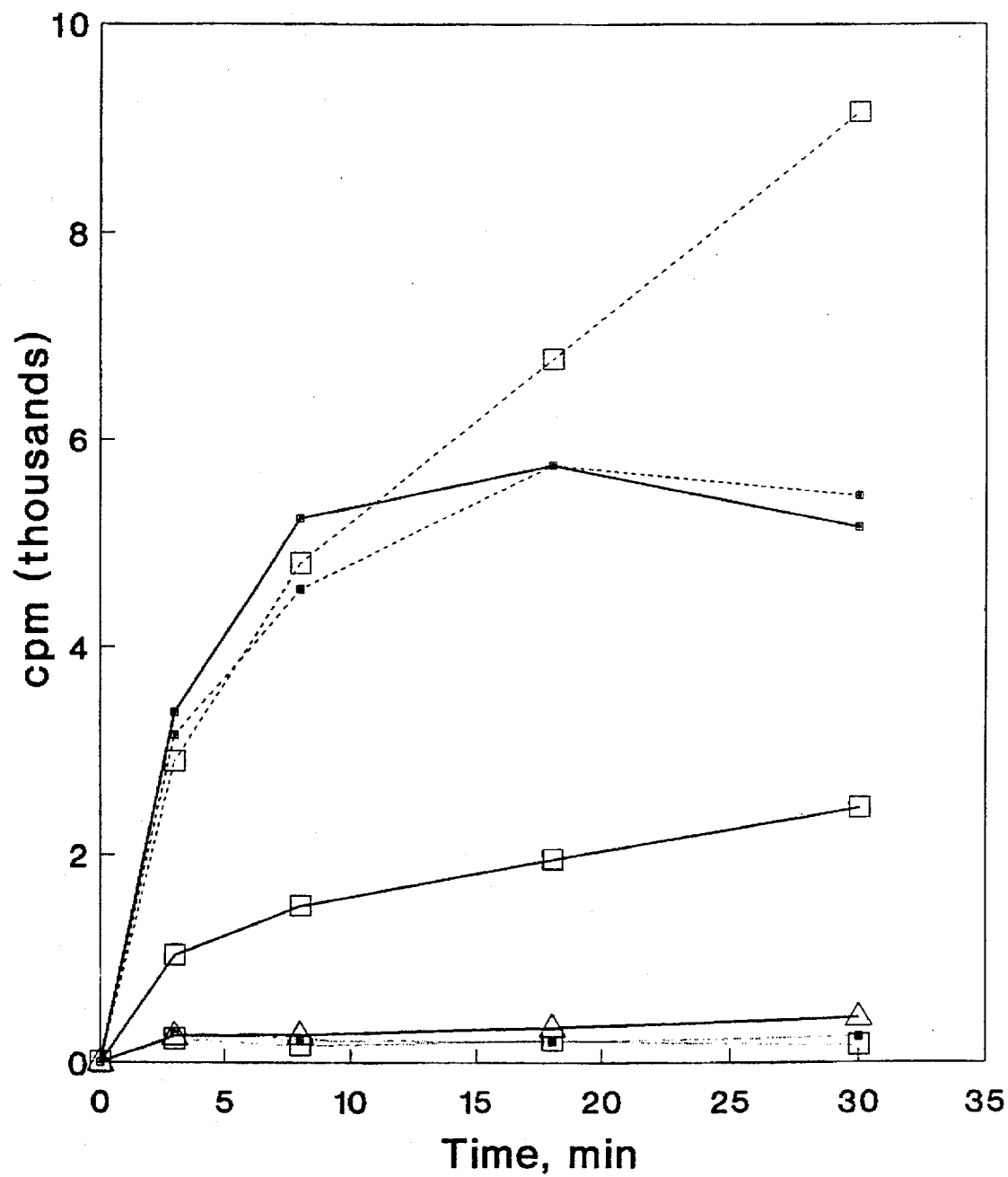

FIG. 35. Guinea Pig Transglutaminase Catalyzed Incorporation of [$^{14}$C] putrescine into FBD or the FBD-SK Complex.

Assays were performed up to 30 min at room temperature with 6 µM FBD SK, or FBD-SK complex, 0.05u/ml transglutaminase, 6 µM[$^{14}$C] putrescine, 6 µM cold putrescine, 50 mM Tris HCl pH 7.5 and 10 mM $CaCl_2$. Controls with 20 mM EDTA (dotted line) or 5mMDTT (dashed line) were also included. (Δ) SK, (●) FBD, (□) FBD-SK complex.

DETAILED DESCRIPTION OF THE INVENTION

The plasmids pFN 975-25, pFN 949-2, pFN 137-2, and pFN196-2 were deposited pursuant to, and in satisfaction of, the requirements of the Budapest Treaty on the International Recognition of the Deposit of Microorganisms for the Purposes of Patent Procedure with the American Type Culture Collection (ATCC), 12301 ParklawnDrive, Rockville, Md. 20852 under ATCC Accession Nos. 67832, 67831, 67910 and 68328, respectively. Similarly, many of the other ATCC deposits referred to in the subject application were also deposited pursuant to, and in satisfaction of, the requirements of the Budapest Treaty.

The primary sequence of human fibronectin has been shown to be organized in three types of homologous repeats, Types I, II, and III. The fibrin-binding domain (FBD), comprised of 259 amino acids with an apparent molecular weight of 31 kD, is made up of five Type I repeats ("fingers"), each about 45 amino acids long with two disulfide bonds, connected to two stretches of about 20-amino acids each at both the N-and C-terminal ends of the protein.

An overall schematic view of the structure of the domains of fibronectin and the recombinant molecules constructed is shown in FIG. 1.

The recombinant fibrin binding domain (FBD) polypeptides claimed herein comprise polypeptide fragments of the fibrin binding domain (r20 kD, r18.5 kD and r12 kD polypeptides). These polypeptides are smaller than the 31 kD polypeptide and comprise part of the sequence of the fibrin binding domain. Many other polypeptides of the fibrin binding domain may be expressed by additional plasmids constructed, using methods known in the art, from plasmids described in this application and these polypeptides may be refolded, reoxidized, and purified using methods described in this application.

The full length recombinant fibrin binding domain (the r31 kD polypeptide) described in this application comprises the first 262 amino acids of fibronectin with the sequence argala-ala-val (SEQ ID NO. 6) at the carboxy-terminus. An additional methionine residue is present at the amino terminus of all the final polypeptides and polypeptide fragments of the FBD. The plasmatic fibrin binding domain derived by tryptic digestion of plasma fibronectin comprises the first 259 amino acids of fibronectin, i.e. with arginine at the carboxy-terminus and the first encoded amino acid, glutamine, converted to a pyroglutamate residue.

The r31 kD polypeptide has five of the Type I homologyloops or fingers discussed above (i.e. 10 disulfide bonds), the r20 kD polypeptide and r18.5 kD polypeptide both have three loops (i.e. 6 disulfide bonds), and the r12 kD polypeptide has two loops (i.e. 4 disulfide bonds). The presence of these disulfide bonds explains the necessity and also the difficulty of the refolding/reoxidation procedure developed to obtain and purify correctly folded FBD polypeptides which have the correct disulfide bonds. The correctly folded FBD polypeptides are biologically active, i.e. they can bind to fibrin; additionally, the r31 kD polypeptide can bind to *Staphylococcus aureus.*

The recombinant FBD polypeptides are produced in inclusion bodies which are obtained in the pellet produced after disruption of the cell cake.

This invention discloses the production of recombinant polypeptide fragments of the fibronectin fibrin binding domain (FBD) for use in thrombus imaging and prevention of thrombus formation. These polypeptides may also bebound to a thrombolytic agent for targeting the agent to a thrombus.

The recombinant cells which produce the polypeptide fragments of the FBD can be any cells in which a DNA sequence encoding an FBD polypeptide fragment has been introduced by recombinant DNA techniques. The cell must be capable of expressing the DNA sequence and producing the polypeptide product. The cell may be a mammalian cell, a fungal cell such as a yeast cell, or a bacterial cell.

The bacterial cell can be any strain including auxotrophic, prototrophic and lytic strains, $F^+$ and $F^-$ strains, strains harboring the cI857 repressor sequence of the λ prophage and strains deleted for the deo repressors or the deo gene.

Examples of wild type *Escherichia coli* strains are prototroph ATCC No. 12435, and auxotroph MC1061 (ATCC Accession No. 67361).

Examples of *Escherichia coli* strains which harbor the λ cI857 repressor sequence are the auxotrophs A1645 harboring plasmid pTVR279-8 (ATCC No. 53216), A1637 harboring plasmid pTV 104(2) (ATCC No. 39384), and A2097 harboring plasmid pSODe2 (ATCC No. 39786), and the prototrophs A4255 harboring plasmid pFN 975-25 (ATCC No. 67832) and biotin-independent A4346 harboring plasmid pHG44 (ATCC No. 53218).

An example of a lytic *Escherichia coli* strain is A4048 which harbors plasmid pHG44 (ATCC No. 53217).

Examples of $F^-$ strains are *Escherichia coli* Sø930 ($F^-$) harboring plasmid pMF 5534 deposited under ATCC No. 67703 and *Escherichia coli* W3100 ($F^-$) harboring plasmid pMFS 929 deposited under ATCC No. 67705.

Examples of *Escherichia coli* strains deleted for the deo gene or deo repressors are Sø732 harboring plasmid pMF 2005 (ATCC No. 67362), Sø540 harboring plasmid pJBF 5401 (ATCC No. 67359), and Sø930 harboring plasmid pEFF 920 (ATCC No. 67706) (see European Patent Application Publication No. 0303972, published Feb. 22, 1989).

The plasmids of this invention may be introduced into suitable bacterial host cells, preferably *Escherichia coli*. An example of a suitable *Escherichia coli* cell is strain A4255 ($F^+$) [ATCC Accession No. 67832], but other *Escherchia coli* strains and other bacteria can also be used as host cells for the plasmids. Such bacteria include *Pseudomonas aeruginosa* and *Bacillus subtilis*.

All of the *Escherichia coli* host strains described above can be "cured" of the plasmids they harbor by methods well known in the art, e.g. the ethidium bromide methods described by R. P. Novick in Bacteriol. Rev. 33:210 (1969).

The bacterial cell may contain the FBD sequence encoding the FBD polypeptide in the body of a vector DNA molecule such as a plasmid. The vector or plasmid is constructed by recombinant DNA techniques so that the sequence encoding the FBD polypeptide is incorporated at a suitable position in the molecule.

Plasmids used for production of the FBD polypeptides can harbor a variety of promoters such as the λ promoter or the deo promoters.

Among the plasmids which may be used for production of FBD polypeptides are the following:

a) Plasmid pFN 975-25 which expresses the r31 kD FBD and which has been deposited in *Escherichia coli* strain A4255 in the ATCC under Accession No. 67832;

b) Plasmid pFN 949-2 which expresses the r20 kD FBD and which has been deposited in *Escherichia coli* strain A4255 in the ATCC under Accession No. 67831;

c) Plasmid pFN 196-2 which expresses the r12 kD FBD and which has been deposited in *Escherichia coli* strain A4255 in the ATCC under Accession No. 68328;

d) Plasmid pFN 197-10 which expresses a modified 12 kD FBD polypeptide, and which has been described in FIG. 11 of this application;

e) Plasmid pFN 195-4 which expresses the r31 kD polypeptide fused to the sequence DGRGDS (SEQ ID NO. 4), and which has been described in FIG. 13 of this application;

f) Plasmid pFN 201-3 which expresses a 12 kD FBD polypeptide fragment under control of $\lambda P_L$ and the $C_{II}$ rbs, and which has ben described in FIG. 26 of this application.

g) Plasmid pFN 203-2 which expresses a 12 kD FBD polypeptide fragment under control of $\lambda P_L$ and the CII rbs, and additionally contains a transcription terminator designated "ter," and which has been described in FIG. 27 of this application and which has been deposited in *Escherichia coli* A4255 in ATCC under Accession No. 68606.

h) Plasmid pFN 205-5 which expresses a 64 kD polypeptide comprising a 31 kD full-length FBD polypeptide fused to a 33 kD fragment of the fibronectin cell-binding domain (CBD) and which has been described in FIG. 25 of this application.

i) Plasmid pFN 208-13 which expresses an 18.5 kD FBD polypeptide fragment which has been described in FIG. 23 of this application and has been deposited in *Escherichia coli* A4255 in ATCC under Accession No. 68456.

j) Any plasmid, derived from the above plasmids, containing FBD sequences encoded by the above plasmids; and k) Any plasmid which contains FBD sequences encoded by the above plasmids.

The subject invention provides an imaging agent which comprises a polypeptide labeled with an imageable marker, such polypeptide having an amino acid sequence substantially present in the fibrin binding domain of naturally-occurring human fibronectin and being capable of binding to fibrin. Also provided is a composition comprising an effective imaging amount of such an imaging agent and a physiologically acceptable carrier.

The polypeptides which are labeled with an imageable marker may be polypeptide fragments of the fibrin binding domain of human fibronectin; they may be produced using recombinant DNA techniques; or encoded by genes synthesized in a DNA synthesizer. Applicants have provided three examples of such polypeptides, with the preferred embodiments being the 18.5 kD and 12 kD polypeptides. As would be understood by one skilled in the art, the terms "having an amino acid sequence substantially present in the fibrin binding domain of naturally-occurring human fibronectin" encompasses, i.e., naturally-occurring allelic variations and recombinant variations, such as site-directed mutagenesis. These are all encompassed by applicants' "polypeptide," the only limitation being the ability to bind to fibrin.

The imageable marker used is a matter of choice to one skilled in the art. It is preferred that the marker be a radioactive isotope, an element which is opaque to X-rays, or a paramagnetic ion.

Radioactive isotopes are commonly used in medicine and are well known to those skilled in the art. It is presently preferred that the marker be indium-111, technetium-99m, iodine-123, iodine-125, iodine-131, krypton-81m, xenon-133, or gallium-67, or mixtures thereof. Most preferably, the marker is technetium-99m or indium-111.

The detectable marker may also be a paramagnetic ion. Paramagnetic ions are also commonly used in medicine. Examples of such markers include chelated metal ions of chromium (III), manganese (II), iron (III), iron (II), cobalt (II), nickel (II), copper (II), praseodymium (III), neodymium (III), samarium (III), gadolinium (III), terbium (III), dysprosium (III), holmium (III), erbium (III), ytterbium (III), or mixtures thereof.

Preferably, the imaging agent comprises a 20 kD polypeptide corresponding to an amino acid sequence present in the fibrin binding domain of human fibronectin and having the amino acid sequence of amino acids 1-153 as shown in FIG. 2 (SEQ ID NO. 16) additional amino acids; or an 18.5 kD polypeptide corresponding to an amino acid sequence present in the fibrin binding domain of human fibronectin and having the amino acid sequence of amino acids 1-154 as shown in FIG. 2 (SEQ ID NO. 16); or a 12 kD polypeptide corresponding to an amino acid sequence present in the fibrin binding domain of human fibronectin and having the amino acid sequence of amino acids 1-109 as shown in FIG. 2 (SEQ ID NO. 16). By means of partial amino acid sequence analysis we have shown that the 12 kD and 20 kD as well as the previously disclosed 31 kD polypeptides all contain an additional N-terminal methionine. Since all the polypeptide fragments of the FBD have identical N-terminal sequences it maybeassumed that the 18.5 kD, 45 kD and 64 kD polypeptides also have the additional N-terminal methionine. However, the invention claimed herein also includes the polypeptides without the additional N-terminal methionine.

The subject invention also provides a method for imaging a fibrin-containing substance, i.e. a thrombus or atherosclerotic plaque, which comprises contacting the fibrin-containing substance to be imaged with the agent as disclosed above under conditions such that the agent binds to the fibrin-containing substance and imaging bound agent and thereby imaging the fibrin-containing substance.

Further provided is a method for imaging a fibrin-containing substance in a subject which comprises:

(a) administering to the subject a composition of the agent as disclosed above under conditions permitting the imaging agent therein to enter the blood stream and bind to fibrin present in the blood vessels;

(b) imaging bound agent within the blood vessels; and thereby (c) imaging the fibrin-containing substance.

Preferably, the polypeptide of the reagent used in the above methods for imaging a fibrin-containing substance is a 20 kD polypeptide corresponding to an amino acid sequence present in the fibrin binding domain of human fibronectin and having the amino acid sequence of amino acids 1-153 as shown in FIG. 2 (SEQ ID NO. 16); the 20 kD polypeptide comprising less than about 20 additional amino acids; an 18.5 kD polypeptide corresponding to an amino acid sequence present in the fibrin binding domain of human fibronectin and having the amino acid sequence of amino acids 1-154 as shown in FIG. 2 (SEQ ID NO. 16); or a 12 kD polypeptide corresponding to an amino acid sequence present in the fibrin binding domain of human fibronectin and having the amino acid sequence of amino acids 1-109 as shown in FIG. 2 (SEQ ID NO. 16).

Preferred markers used in the above methods for imaging a fibrin-containing substance are radioactive isotopes, elements which are opaque to X-rays, or paramagnetic ions. Most preferred markers are radioactive isotopes, such as indium-111, technetium-99m, iodine-123, iodine-125, iodine-131, krypton-81m, xenon-133, and gallium-67.

Imaging may be done through any of the methods known to one skilled in the art. These methods include but are not limited to X-ray, CAT scan, PET scan, NMRI, and fluoroscopy. Preferably, the imaging of the fibrin-containing substance by the above methods is carried out using a gamma camera.

Further provided is a plasmid for expression of a polypeptide having an amino acid sequence substantially present in the fibrin binding domain of naturally-occurring human fibronectin and being capable of binding to fibrin comprising DNA encoding the polypeptide and DNA encoding suitable regulatory elements positioned relative to the DNA encoding the polypeptide so as to effect expression of the polypeptide in a suitable host cell.

Applicants have provided three examples of polypeptide fragments of the fibrin binding domain of fibronectin.

These include the r20 kD, r18.5 kD and r12 kD polypeptides. These polypeptides exhibit the binding and adhesive properties of portions of naturally-occurring human fibronectin. The scope of the claims of the subject application are not intended to be limited to these three FBD polypeptide fragments, which are examples of preferred embodiments only.

In preferred embodiments, the polypeptide is about a 20 kD polypeptide corresponding to an amino acid sequence present in the fibrin binding domain of human fibronectin; about an 18.5 kD polypeptide corresponding to an amino acid sequence present in the fibrin binding domain of human fibronectin; or about a 12 kD polypeptide corresponding to an amino acid sequence present in the fibrin binding domain of human fibronectin.

In more preferred embodiments, the polypeptide is an 18.5 kD polypeptide corresponding to an amino acid sequence present in the fibrin binding domain and having the amino acid sequence of amino acids 1-154 as shown in FIG. 2 (SEQ ID NO. 16), a 20 kD polypeptide corresponding to an amino acid sequence present in the fibrin binding domain of human fibronectin and having the amino acid sequence of amino acids 1-153 as shown in FIG. 2 (SEQ ID NO. 16); the 20 kD polypeptide comprising less than about 20 additional amino acids; or a 12 kD polypeptide corresponding to an amino acid sequence present in the fibrin binding domain of human fibronectin and having the amino acid sequence of amino acids 1-109 as shown in FIG. 2 (SEQ ID NO. 16). As noted above, the polypeptides also may have the additional N-terminal methionine. However, the invention claimed herein also includes the polypeptides without the additional N-terminal methionine.

Naturally-occurring human fibronectin is as it occurs in the human body (in plasma).

As used throughout this application, a substantial portion is at least one fifth (⅕). A polypeptide which has the biological activity of the fibrin binding domain of naturally-occurring human fibronectin exhibits binding or adhesive properties similar to those of the fibrin binding domain of naturally-occurring human fibronectin when the level of such activity is assayed or determined.

In this invention, the amino acid sequence of the various functional domains are determined by cleavage of the cDNA which encodes the domains with restriction enzymes, and do not necessarily correspond to the amino acid sequence of the domains as obtained and defined byproteolytic digestion of fibronectin.

The plasmid of this invention further comprises suitable regulatory elements positioned relative to the DNA encoding the polypeptide so as to effect expression of the polypeptide in a suitable host cell, such as promoters and operators, e.g. $\lambda P_L O_L$, ribosomal binding sites, e.g. $C_{II}$, and repressors. Other suitable regulatory elements include, for example, the lac, trp, tac, lpp and deo promoters (European Patent Application Publication No. 0303972, published Feb. 22, 1989).

The suitable regulatory elements are positioned relative to the DNA encoding the polypeptide so as to effect expression of the polypeptide in a suitable bacterial host cell. In preferred embodiments of the invention, the regulatory elements are positioned close to and upstream of the DNA encoding the polypeptide.

Further provided is a plasmid designated pFN 949-2 and deposited in *Escherichia coli* strain A1645 under ATCC Accession No. 67831. Plasmid pFN 949-2 encodes a 20 kD polypeptide fragment of the fibrin binding domain of human fibronectin comprising amino acids 1-153 of FIG. 2 with an additional N-terminal methionine, and less than 20 additional amino acids.

Also provided is a plasmid designated pFN 196-2 and deposited in *Escherichia coli* strain A4255 under ATCC Accession No. 68328. Plasmid pFN 196-2 encodes a 12 kD polypeptide fragment of the fibrin binding domain of human fibronectin comprising amino acids 1-109.

Also provided is a plasmid designated pFN 208-13 deposited in *Escherichia coli* A4255 under ATCC Accession No. 68456. Plasmid pFN 208-13 encodes an 18.5 kD polypeptide fragment of the fibrin binding domain of human fibronectin comprising amino acids 1-154 of FIG. 2 (SEQ ID NO. 16) and may be assumed to have an additional N-terminal methionine as described above.

Also provided is a plasmid designated pFN 203-2 deposited in *Escherichia coli* A4255 under ATCC Accession No. 68606. Plasmid pFN 203-2 expresses a 12 kD polypeptide fragment of the fibrin-binding demain of human fibronectin comprising amino acids 1-109 of FIG. 2 (SEQ ID NO. 16) with an additional N-terminal methionine.

Also provided is a plasmid designated pFN 205-5 which expresses a 64 kD polypeptide comprising a 31 kD full-length FBD polypeptide fused to a 33 kD fragment of the fibronectin CBD (described in FIG. 25).

As discussed above, it may be assumed that all of the polypeptides produced by the plasmids of this invention contain an additional N-terminal methionine.

In presently preferred embodiments, the invention provides an *Escherichia coli* cell containing the plasmid designated pFN 975-25 and wherein the cell is deposited under ATCC Accession No. 67832; an *Escherichia coli* cell containing the plasmid designated pFN 949-2 and wherein the cell is deposited under ATCC Accession No. 67831; and an *Escherichia coli* cell containing the plasmid designated pFN 196-2 and wherein the cell is deposited under ATCC Accession No. 68328; an *Escherichia coli* cell containing the plasmid designated pFN 203-2 and wherein the cell is deposited under ATCC Accession No. 68606; and an *Escherichia coli* cell containing the plasmid designated pFN208-13 and wherein the cell is deposited under ATCC Accession No. 68456.

The invention provides a method of producing a polypeptide having an amino acid sequence substantially present in the fibrin binding domain of naturally-occurring human fibronectin and being capable of binding to fibrin which comprises treating a cell containing a plasmid comprising DNA encoding the polypeptide so that the DNA directs expression of the polypeptide and recovering from the cell the polypeptide so expressed.

Preferably, the polypeptide so produced is an 18.5 kD, 20 kD, or 12 kD polypeptide fragment of the fibrin binding domain.

Further provided is a purified polypeptide substantially free of other substances of human origin which has an amino acid sequence substantially present in the fibrin binding domain of naturally-occurring human fibronectin and being capable of binding to fibrin.

Preferably, the polypeptide is a 20 kD polypeptide corresponding to an amino acid sequence present in the fibrin binding domain of human fibronectin and having the amino acid sequence of amino acids 1-153 as shown in FIG. 2 (SEQ ID NO. 16); the 20 kD polypeptide comprising less than about 20 additional amino acids; or an 18.5 kD polypeptide corresponding to an amino acid sequence present in the fibrin binding domain of human fibronectin and having the amino acid sequence of amino acids 1-154 as shown in FIG. 2 (SEQ ID NO. 16); or a 12 kD polypeptide corresponding to an amino acid sequence present in the fibrin binding domain of human fibronectin and having the amino acid sequence of amino acids 1-109 as shown in FIG. 2 (SEQ ID NO. 16). As noted above, the polypeptides also may have the additional N-terminal methionine. However, the invention claimed herein also includes the polypeptides without the additional N-terminal methionine.

These shorter FBD polypeptide fragments, i.e. 20 kD, 18.5 kD, and 12 kD are advantageous over the 31 kD FBD polypeptide. They are easier to refold, lack the bacterial binding domain, and have a much reduced binding specificity for other vascular components such as endothelial cells, extracellular matrix and fibronectinbycomparison to the 31 kD polypeptide, while maintaining a fibrin-binding activity similar to that of the 31 kD polypeptide.

The invention further provides such a purified polypeptide substantially free of other substances of human origin fused to a second polypeptide, the second polypeptide comprising a substantial portion of the amino acid sequence of the cell binding domain of naturally-occurring human fibronectin.

Preferably, the fused polypeptide is a 45 kD fused polypeptide, wherein the purified polypeptide is a 12 kD polypeptide and the second polypeptide which comprises a substantial portion of the cell binding domain of naturally-occurring human fibronectin is a 33 kD polypeptide. The fused polypeptide may also comprise a 31 kD purified polypeptide and a second polypeptide which contains the amino acid sequence DGRGDS (SEQ ID NO. 4). Another preferred fused polypeptide is a 64 kD fused polypeptide, wherein the purified polypeptide is a 31 kD polypeptide and the second polypeptide which comprises a substantial portion of the cell binding domain of naturally-occurring human fibronectin is a 33 kD polypeptide.

The invention also provides a plasmid for expression of the 45 kD fused polypeptide, disclosed above, designated pFN 202-5; a plasmid for expression of the 31 kD/GRGDS (SEQ ID NO. 7). Used polypeptide, disclosed above, designated pFN 195-4; and a plasmid for expression of the 64 kD fused polypeptide, disclosed above, designated pFN 194-2.

As used throughout the subject application, "fused" or "bound" encompasses polypeptides bound covalently, noncovalently, or conjugated. The polypeptides may be conjugated through other chemical moieties including amino acid or polypeptide cross-linkers, which are standardly used in the art and are well-known to those skilled in the art to which the subject invention pertains.

Numerous methods are known in the art for detection of thrombi, such as radioactive labeling (nuclear medicine use of isotopes), radio-opaque labeling (such as CAT scan), and Magnetic Resonance Imaging (MRI). Any of these labeling methods can be used in the method of the subject invention for detecting the thrombus. In each of these detection methods the polypeptide is used as a diagnostic agent for detecting the thrombus.

Also provided is a method of refolding and reoxidizing a polypeptide having an amino acid sequence substantially present in the fibrin binding domain of naturally-occurring human fibronectin but lacking the disulfide bonds of naturally-occurring human fibronectin and being capable of binding to fibrin which comprises contacting the polypeptide with a thiol-containing compound in the presence or absence of a disulfide so as to refold and reoxidize the polypeptide.

Preferably, the thiol-containing compound is selected from the group consisting of glutathione, thioredoxin, β-mercaptoethanol, and cysteine.

Preferably, the thiol-containing compound is β-mercaptoethanol and the disulfide is produced in situ by introduction of air.

Preferably, the polypeptide is selected from the group consisting of an 18.5 kD polypeptide, a 20 kD polypeptide, a 12 kD polypeptide and a 45 kD polypeptide. The 45 kD chimera polypeptide consisting of the 12 kD FBD fused to the 33 kD CBD has been refolded and reoxidized using exactly the same method as the smaller FBD polypeptides.

The method of refolding and reoxidizing may additionally comprise contacting the polypeptide with a denaturant. Preferred denaturants are guanidine hydrochloride and urea.

Preferably, the polypeptide is at a low concentration, such as below 1,000 μg/ml.

The subject invention also provides a method for recovering a purified biologically active polypeptide having an amino acid sequence substantially present in the fibrin binding domain of naturally-occurring human fibronectin and being capable of binding to fibrin which comprises:

(a) producing in a bacterial cell by means of expression of a plasmid containing DNA encoding the polypeptide a first polypeptide having the amino acid sequence of the polypeptide but lacking the disulfide bond;

(b) disrupting the cell so as to produce a lysate containing the first polypeptide;

(c) centrifuging the lysate so as to concentrate the first polypeptide;

(d) separating the concentrated first polypeptide;

(e) solubilizing the separated, concentrated first polypeptide;

(f) refolding and reoxidizing the solubilized first polypeptide so as to form the biologically active polypeptide;

(g) separating the refolded and reoxidized biologically active polypeptide;

(h) recovering the purified, refolded and reoxidized biologically active polypeptide; and (i) purifying the biologically active polypeptide so recovered.

Preferably, the refolding and reoxidizing comprises contacting the polypeptide with a thiol-containing compound in the presence or absence of a disulfide so as to refold and reoxidize the polypeptide. Preferably, the thiol-containing compound is selected from the group consisting of glutathione, thioredoxin, S-mercaptoethanol, and cysteine.

In one preferred embodiment, the thiol-containing compound is β-mercaptoethanol and the disulfide is produced in situ by introduction of air.

Preferably, the polypeptide is selected from the group consisting of an 18.5 kD polypeptide, a 20 kD polypeptide, a 12 kD polypeptide and a 45 kD polypeptide. As noted above, the 45 kD chimera polypeptide consisting of the 12 kD FBD fused to the 33 kD CBD has been refolded and reoxidized using exactly the same method as the smaller FBD polypeptides.

The method may additionally comprise contacting the polypeptide with a denaturant, such as guanidine hydrochloride or urea.

Preferably, the polypeptide is at a low concentration, such as below 1,000 μg/ml.

Preferably, the separating of the concentrated polypeptide in step (c) comprises chromatography, preferably Heparin-Sepharose chromatography.

The subject invention also provides a method of inhibiting thrombus formation in a subject susceptible to thrombus formation which comprises administering to the subject an amount of a polypeptide (selected from the polypeptides and fused polypeptides disclosed above) effective to inhibit thrombus formation. The polypeptide may be reduced or alternatively the S-H groups may be blocked (e.g. by carboxymethylation or carboxamidomethylation to prevent reoxidation).

The subject invention also provides a polypeptide as disclosed above bound to a thrombolytic agent for the targeting of thrombolytic agents. The thrombolytic agents may be selected from tissue plasminogen activator (TPA), urokinase, streptokinase, prourokinase, Anisoylated Plasminogen-Streptokinase Activator Complex (Eminase™), TPA analogs, or a protease.

In one embodiment of the invention, the polypeptide has an amino acid sequence substantially present in the fibrin binding domain of naturally-occurring human fibronectin, is capable of binding to fibrin, has a molecular weight above about 6 kD but less than about 20 kD, has the amino acid sequence gln-ala-gln-gln (SEQ ID NO. 1) or met-gln-ala-gln-gln (SEQ ID NO. 8) the N-terminus of the polypeptide and wherein the thrombolytic agent is streptokinase.

In a preferred embodiment, the polypeptide is a 12 kD polypeptide and the thrombolytic agent is streptokinase.

Further provided is a method for achieving thrombolysis of a thrombus which comprises administering to a subject an amount of the polypeptide bound to a thrombolytic agent effective to achieve thrombolysis.

The invention also provides a method of treating a subject with a wound which comprises administering to the subject an amount of a purified polypeptide, which is substantially free of other substances of human origin which has an amino acid sequence substantially present in the fibrin binding domain of naturally-occurring human fibronectin and is capable of binding to fibrin, in conjunction with a polypeptide which comprises a substantial portion of the cell binding domain of naturally-occurring human fibronectin effective to treat the wound. In one embodiment of the method, the cell binding domain polypeptide is a 40 kD polypeptide or a 33 kD polypeptide.

Further provided is a method of treating a subject with a wound which comprises administering to the subject an amount of the fused polypeptide of a purified polypeptide, which is substantially free of other substances of human origin which has an amino acid sequence substantially present in the fibrin binding domain of naturally-occurring human fibronectin and which is capable of binding to fibrin, fused to a second polypeptide which comprises a substantial portion of the amino acid sequence of the cell binding domain of naturally-occurring human fibronectin effective to treat the subject. In one embodiment of the method, the fused polypeptide may be a 45 kD polypeptide, wherein the polypeptide is a 12 kD polypeptide and the second polypeptide is a 33 kD polypeptide. In another embodiment, the fused polypeptide may be a 64 kD fused polypeptide, wherein the polypeptide is a 31 kD polypeptide and the second polypeptide is a 33 kD polypeptide.

The wound treated by the methods of the invention may be a cutaneous wound, such as an incisional wound, a skin deficit wound, a skin graft wound, or a burn wound. The wound may also be an eye wound, wherein the eye wound is a corneal epithelial would or a corneal stromal wound. Furthermore, the the wound may be a tendon injury.

EXAMPLES

All the references to map positions correspond to the identically numbered positions along the nucleotide sequence of human fibronectin cDNA shown in FIG. 2 (SEQ ID NO. 16) (see also FIG. 3 of Baralle, F. E., European Patent Publication No. 207,751, published Jan. 7, 1987).

This patent application is directed to polypeptide fragments of the N-terminus fibrin binding domain (FBD).

Experimental results with the 31 kD polypeptide are presented for purposes of comparison with the shorter fragments. Some of the proteins described are fusion proteins comprising an FBD fragment joined at its C-terminus to the N-terminus of a fragment of the cell binding domain (CBD).

The cDNA sequence corresponding to the CBD which applicants have cloned and expressed is missing the 270 bp extra domain (ED) segment which extends from nucleotides 4811 to 5080, inclusive, on the Baralle map (see FIG. 2 ) (SEQ ID NO. 16). Thus, the cDNA sequence which is said to extend from nucleotide 3317 to 5566 on the Baralle map, contains only 1980 nucleotides, because it is missing the 270 nucleotides of the ED segment, namely from nucleotides 4811 to 5080 inclusive; this region is also known in the art as the ED-A region. Because nucleotide 5081 is changed from G to A, amino acid 1690 is changed from alanine to threonine. Similarly, the polypeptide expressedby that DNA fragment would encode from amino acid 1102 to amino acid 1851 on the Baralle map but would be missing the 90 amino acids encoded by the ED region, namely amino acids 1600-1689 inclusive, and thus it would contain only 660 amino acids. This is true for all CBD fragments described in this application which span the ED region. (The region known in the art as the ED-B region is missing both in Baralle's sequence and in applicants' cDNA.)

The EcoRI cleavage site shown at position 3317 was constructed by applicants during the cloning procedure by use of EcoRI linkers. This GAATTC sequence at positions 3313 to 3318 differs in 1 nucleotide from the corresponding Baralle sequence GATTC. This introduces a single nucleotide change C to A at nucleotide 3315. This changes the corresponding amino acid number 1100 from Thr to Asn.

Example 1

Preparation of a Fibronectin cDNA Library

A cDNA library was prepared in λgt11 from poly A+ mRNA isolated from human liver according to the published procedures (13,14). The cDNA fragments were cloned using EcoRI linkers and the cDNA library was screened for fibronectin (FN) positive plasmids using the following synthetic DNA probes.

| Probe | Nucleotides |
|---|---|
| Probes for cell binding domain (CBD): | |
| (3')CACTCTATAATGTCCTAGTGAATGCCTCTTTGTCCTCC (SEQ ID NO. 9) | (4355–4392) |
| (3')AGAATCTCCTTCTGTCTTTTGTCCAGAACTAAG (SEQ ID NO. 10) | (3967–3999) |
| (3t)CCGGTTGTTAGTTGTCAAAGACTACAAGGCTCCCTGGACC (SEQ ID NO. 11) | (4200–4239) |
| Probes for N-terminal fibrin binding domain (FBD): | |
| (3')GGGGGTCGGAGGGATACCGGTGACACAGTGTCTTAA (SEQ ID NO. 12) | (817–850) |
| (3')CGACGGGTGCTCCTTTAGACGTGTTGGTTACTTCCCCAGTAC (SEQ ID NO. 13) | (1310–1340) |

A series of FN cDNA clones covering the entire region of fibrin, collagen, heparin and cell binding domains was identified and isolated (FIG. 9). The cDNA fragments were subcloned into the EcoRI site of pBR322.

The mRNA of FN is alternatively spliced and therefore different length cDNA's have been reported in the literature. Applicants' cDNA corresponding to the cell binding domain has a 270 base pair deletion from base 4811 to base 5080 on the FN physical map (the complete non spliced cDNA).

Example 2

Expression and Purification of Fibrin Binding Domain (FBD) Polypeptides

A. Expression of a partial FBD 20 kD polypeptide

The FN cDNA clones obtained as described in Example 1 and depicted in FIG. 9, did not include DNA encoding amino acids 1-190 of the FN molecule. These amino acids are part of the FBD. The DNA corresponding to nucleotides 14 to 472 and coding for amino acids 1-153 (FIG. 2A) (SEQ ID NO. 16) was instructed by ligation of 7pairs of chemically synthesized nucleotides (FIGS. 3 (SEQ ID NOS. 17–30) and 4). The synthetic DNA fragment was designed to contain an ATG initiation codon at the 5' end as well as convenient restriction sites for introduction into various expression vectors. To enable further manipulation of the DNA sequence coding for the FBD, nucleotide number 19, thymidine (T) was changed to adenine (A), thereby eliminating a DdeI restriction site without altering the amino acid sequence. (The site of the nucleotide ,change is denoted by an asterisk in linker #1 shown in FIG. 3A (SEQ ID NOS. 17–24).) The various steps for the cloning of the above synthetic DNA fragment into pBR322 plasmid vector digested with EcoRI and BamHI are described in FIG. 4.

The plasmid obtained was designated pFN 932-18. The DNA fragment coding for the first 153 N-terminal amino acids of fibronectin from plasmid pFN 932-18, was inserted into pTV 301, a λ $P_L$ expression vector, between the NdeI and BglII sites replacing the DNA sequence coding for human growth hormone (hGH) in plasmid pTV 301 (FIG. 5).

The resulting plasmid, pFN 949-2, was deposited with the American Type Culture Collection under Accession No. 67831. Plasmid pFN 949-2 was used to transform *Escherichia coli* prototroph A4255. These transformed *Escherichia coli* cells were found to express the partial FBD polypeptide in amounts comprising about 5% of the total cellular proteins. The polypeptide has a mobility of about 20 kD on reduced SDS polyacrylamide gels as determined from the mobility of the size markers. The polypeptide comprises the first 153 amino acids of fibronectin followed by 4 amino acids coded for by a synthetic linker and then several amino acids resulting from readthrough into the pBR322 vector due to the lack of a TAA termination codon, i.e., a total of 153 amino acids plus less than 20 additional amino acids, with an additional N-terminal methionine. Throughout this specification the polypeptide is referred to as the r20 kD polypeptide or the r20 kD FBD.

B. Expression of a "complete" FBD polypeptide

In order to obtain expression of the entire FBD polypeptide containing amino acids 1 to 262 the following plasmids were constructed:

1. Insertion of termination codon TAA at the 3' end

A synthetic oligonucleotide containing a TAA termination codon and a BglII site having the following sequence:
5' CTGTTTAATAAGCA (SEQ ID NO. 14)
3' GACAAATTCGTCTAG (SEQ ID NO. 15)
was ligated to the 3' end of an EcoRI-PvuII fragment isolated from FN cDNA clone p931-5 and to a pBR322 vector digested with EcoRI and BamHI as described in FIG. 6 (SEQ ID NOS. 2 and 3). plasmid obtained was designated pFN935-12.

2. Subcloning of carboxyterminal region of FBD in a λ $P_L$ pression vector

An EcoRI-HincII DNA fragment coding for the carboxy-terminal region of the FBD was isolated from plasmid pFN935-12 and ligated to plasmid pTV 194-80 digested with EcoRI and SmaI as described in coassigned PCT Publication No. WO 90/07577 (FIG. 46). The plasmid obtained was designated pFN 946-12.

3. Syntheses and cloning of DNA corresponding to nucleotides 468-599 of FN

Three pairs of chemically synthesized nucleotides were ligated to an EcoRI-DdeI FN fragment isolated from plasmid pFN932-18 (FIG. 4) in the presence of pUC19 vector DNA (purchased from GIBCO BRL Co.) digested with EcoRI and XbaI as described in detail in the above-referenced PCT Publication (FIG. 47). The plasmid obtained was designated pFN 948-4.

4. Construction of a plasmid encoding the complete FBD region

In order to construct a plasmid which codes for the entire FBD, amino acid 1 to amino acid 262, an EcoRI-XbaI DNA fragment coding for FN was isolated from plasmid pFN948-4 and inserted into plasmid pFN 946-12 digested with EcoRI and XbaI as described in the above-referenced PCT Publication (FIG. 48). The plasmid obtained was designated pFN-957. This plasmid contains the complete coding sequence for FBD but does not express the FBD polypeptide as it lacks a ribosomal binding site (RBS).

5. Expression of the FBD under λ $P_L$ promoter and cII RBS

An NdeI-HindIII fragment containing the FBD coding region and the $T_1T_2$ transcription terminators was isolated from plasmid pFN-957 and inserted into plasmid pTV 301 digested with NdeI and HindIII as described in the above-referenced PCT Publication (FIG. 49). The resulting plasmid, designated as pFN 962-3, directs the expression of a FBD polypeptide under the control of λ $P_L$ promoter and cII ribosomal binding site. *Escherichia coli* strains A1645 and A4255 transformed with this plasmid expressed only small amounts of the FBD polypeptide. The expression of the FBD polypeptide was detectable only by Western blot analysis using polyclonal antibodies directed against human plasma derived FN.

6. Expression of an FBD polypeptide under the λ $P_L$ promoter and the β-lactamase promoter and ribosomal binding site As the level of expression of the FBD polypeptide obtained with plasmid pFN 962-3 was low, we added a DNA fragment coding for the β-lactamase promoter and β-lactamase RBS (PBLA). The DNA fragment coding for PBLA was isolated from plasmid pBLA11 (ATCC Accession No. 39788) and inserted into plasmid pFN 962-3 digested with NdeI, filled in with Klenow enzyme and digested with EcoRI (see the above-referenced PCT Publication). The plasmid obtained, designated pFN 975-25, was deposited with the American Type Culture Collection under ATCC Accession No. 67832. This plasmid was used to transform *Escherichia coli* prototroph A4255 (F+).

These *Escherichia coli* cells were found to express the "complete" FBD polypeptide at levels comprising about 5–8% of the total cellular proteins. The polypeptide migrated on SDS-PAGE gels under reducing conditions with an apparent molecular weight of 31 kD, hence it is referred to as the 31 kD polypeptide or the r31 kD FBD.

C. Fermentation and growth conditions

The clone expressing the r31 kD FBD polypeptide was fermented in rich medium (yeast extract and casein hydrolysate) containing ampicillin. Growth was carried out at 30° C. Expression was obtained upon induction at 42° C for 2 hours, and subsequently bacterial cell cake containing the r31 kD FBD polypeptide was obtained. Similarly, the clone expressing the r20 kD FBD was fermented and bacterial cell cake containing the r20 kD FBD polypeptide was obtained.

D. Refolding and purification of recombinant fibrin binding domain (r31 kD) polypeptide The process is made up of three stages:

1. Crude processing of the bacterial cake.
2. Refolding/reoxidation.
3. Purification.

1. Crude processing

The cake is disrupted first in 5 volumes of 50 mM Tris-HCl/50 mM Na-EDTA, pH 8 (Buffer 1); the pellet is then treated with 1.2 volumes of Buffer i containing 100 mg/liter lysozyme (2 hours agitation at 37° C.). Triton X 100 is added to the resulting suspension (to 1%), and after 30 min. at room temperature the suspension is centrifuged and the pellet is resuspended and washed twice with water. All these steps are performed by disruption of the pellet and centrifugation and the 31 kD stays in the pellet, as evidenced from SDS-PAGE gels.

The washed pellet is suspended in 14 volumes of 10 mM Tris-HCl/5mM EDTA/2 mM PMSF/2 mM 6-aminocaproate, pH 7.5 (Buffer A) and then treated successively with Buffer A containing: 1% decyl sulfate, 1% decyl sulfate/5% glycerol and 5% glycerol. The final treatment is with Buffer A without additives.

2. Refolding/reoxidation

Principle: To dissolve the pellet in 6M guanidine-HCl-GuCl-in the presence of a thiol reducing agent, such as glutathione—GSH—and to refold/reoxidize at a lower GuCl concentration by the addition of oxidized glutathione-GSSG.

The washed pellet from step 1 above is dissolved in 150–700 volumes of 6M GuCl/3 mM GSH in Buffer A. The concentration of GuCl is lowered gradually, i.e., first 2M, then 1M and 0.5M, while keeping the concentration of all other components constant, except for the volume, which at this stage is brought to 500–1000 fold higher than that of the pellet. At one of the intermediate concentrations of GuCl, i.e., between 0.5 and 2M, refolding is initiated by the addition of 0.3 mM of GSSG and incubation at room temperature for 24–48 hours. The refolded 31 kD is then dialyzed against Buffer A without additives.

3. Purification

Concentration: The large volume of refolded 31 kD is first centrifuged to remove the insoluble pellet that contains no 31 kD and is then dialyzed against Tris-HCl, pH 7.8, before being concentrated and initially purified on a Heparin-Sepharose column.

Improved procedures for refolding/reoxidation and purification of the polypeptide fragments of the FBD are described in Examples 5 and 10.

Example 3

Pharmacodynamics of the r31 kD, r20 kD, r18.5 kD and r12 kD Fibrin Binding Domain polypeptide Fragments The intensity and resolution of a clot (thrombus) image is governed by the interplay of the rate of incorporation of the radiopharmaceutical and its blood clearance rate. In order to elucidate the metabolic behavior of the r31 kD fibrin-binding domain, and to compare it to fibronectin (FN), the r31 kD fibrin binding domain and plasma fibronectin were both iodinated with 125I by the ICl method (24) and injected intravenously into rats. The results are shown in FIG. 7 which represents the pharmacokinetic behavior of $^{125}$I-r31 kD FBD and $^{125}$I-FN. Blood samples were withdrawn at the times shown on the graph.

FIG. 7 demonstrates that the clearance rates of the two radioactive molecules are different and after 5 hours, only 3% of the r31 kD FBD but 20% of FN respectively remain in circulation.

Some of the rats were kept in individual metabolic cages, and accumulated urine and feces were collected at 7 hours and 24 hours. About 30% of the injected $^{125}$I-r31 kD radioactivity was excreted in the urine during the first 7 hours, and more than 90% was excreted after 24 hours. All of the urinary radioactivity was trichloroacetic acid-soluble, which is indicative of proteolytic degradation. The analysis of a variety of organs (kidney, stomach, liver, lung, uterus, ovary, adrenal, colon, ileum, skin, brain, eye, muscle, bladder, heart, spleen, trachea, aorta and vena-cava) did not reveal any specific accumulation, and the kinetics of disappearance of the radioactivity followed a pattern similar to that of the blood. In most of the organs, the specific radioactivity (cpm/gram tissue) was lower than that of the serum.

The results indicate that exogenous recombinant 31 kD amino-terminal polypeptide of FN is moderately degraded and excreted in the body. The pharmacokinetic behavior is not consistent with a first-order kinetics, which may indicate that the polypeptide is moderately distributed in the tissues and body compartments other than blood. This is also evident from the finding that the degree of degradation does not increase during the 4–24 hour period, thus reflecting a gradual release of the polypeptide from body compartments. The exclusive and relatively early appearance of the metabolites in the urine indicates that the polypeptide is readily excreted through the kidneys. The lack of accumulation of the material in the liver may be an indication that this organ is not a major locus of degradation and is not involved in detoxification.

The relatively short half-life of r31 kD FBD is important for its possible use in diagnostic imaging of thrombi. The recombinant 31 kD FBD (r31 kD) may be labeled radioactively or by other means and then introduced into the blood for the purpose of imaging thrombi.

The shorter half-life of the molecule is also important when utilizing it to prevent clot formation. By contrast, heparin, the current therapeutic agent of choice, suffers from a very long half-life.

A similar experiment was performed using iodinated 31 kD fibrin binding domain of plasmatic fibronectin and similar pharmacokinetics and distribution of radioactivity were observed.

The 31 kD polypeptide was obtained by cleavage of plasmatic FN as follows: the plasmatic FN was purified on a Gelatin-Sepharose column from which it was eluted and stored in 1 M guanidinium hydrochloride. Thereafter, 206 mg of FN, after dialysis against 10mM of Tris-HCl, were digested with 0.01% of TPCK-trypsin at 37° C. for 5 minutes. The tryptic digest was loaded on a DE52 column (6 ml) and 1/5 of the flow-through fraction (50 ml) was applied to a CM-Sepharose column (3 ml) and eluted with a NaCl gradient (0–0.5M). About 80% of the polypeptide was recovered in the salt gradient (peak at about 220mM) and after dialysis to remove the salt about ½ of the polypeptide was loaded on a Heparin-Sepharose column (1.5 ml) and eluted with 0.5 M NaCl. Approximately 75% of the polypeptide was recovered in this fraction, i.e., about 1 mg (about 40% of the theoretical yield). This fraction was >90% pure 31 kD polypeptide, and was iodinated by the method described above. In an improved embodiment the CM-Sepharose step is omitted and the Heparin-Sepharose step is performed directly after the DE52 column.

Note that plasmatic 31 kD FBD contains the first 259 amino acids of FN, whereas the recombinant 31 kD FBD contains the first 262 amino acids of FN and an additional N-terminal methionine.

Pharmacokinetics of the r20 kD, r18.5 kD and r12 kD fibrin binding domain polypeptides Similar experiments were performed using labeled r20 kD, r18.5 kD and r12 kD fibrin binding domain polypeptides produced as described in Examples 2, 4, 5 and 10. The pharmacokinetics of these polypeptides was found to be very similar to that of the r31 kD polypeptide.

Example 4

Expression and Fermentation of Additional Fibrin Binding Domain (FBD) Polypeptides In Example 2 the expression of a partial r20 kD FBD and the full-length r31 kD FBD was described and in coassigned PCT Publication No. WO 90/07577, Example 24, an improved procedure for refolding and purification of the 31 kD FBD was disclosed. The construction of plasmids for expression of additional polypeptide fragments of the FBD is now described.

A. Expression of r12 kD FBD polypeptide

Plasmid pFN 975-25, ATCC No. 67832, expresses the full-length r31 kD FBD of fibronectin and from it plasmid pFN 196-2 which expresses a partial FBD was constructed as shown in FIG. 10. This plasmid was transformed into *Escherichia coli* strain A1645 and thence into *Escherichia coli* strain A4255 and deposited in A4255 in the ATCC under Accession No. 68328. These transformed cells were found to be good expressors of the partial FBD polypeptide in amounts comprising about 5% of the total cellular protein. The polypeptide has a mobility of about 14.4 kD on SDS polyacrylamide gels under reducing conditions as determined from the mobility of the size markers. The polypeptide comprises the first 109 amino acids of fibronectin. An additional methionine residue is present at the N-terminus of the final polypeptide. Throughout this specification this polypeptide is referred to as the r12 kD polypeptide fragment or the r12 kD FBD.

B. Expression of a modified 12 kD (12 kD) partial FBD polypeptide

Plasmid pFN 975-25 (ATCC No. 67832), which expresses the full-length r31 kD FBD, was used to construct plasmid pFN 197-10 which expresses a modified r12 kD polypeptide (r12 kD') as shown in FIG. 11. The fibronectin FBD sequence was modified to produce an NdeI site immediately after nucleotide 340. This plasmid was transformed into *Escherichia coli* strain A1645 and thence into *Escherichia coli* strain A4255. These transformed cells were found to be good expressors of the modified r12 kD partial FBD in amounts comprising about 5% of the total cellular protein. The polypeptide has a similar mobility to the unmodified 12 kD FBD as determined on reduced SDS polyacrylamide gels. The polypeptide comprises the first 109 amino acids of fibronectin followed by additional amino acids histidine and methionine. An additional methionine residue is present at the N-terminus of the final polypeptide. This polypeptide is designated the r12 kD polypeptide or the r12 kD' FBD.

C. Expression of a modified r12 kD' FBD fused to the 33 kD cell bindinn domain

Plasmid pFN 197-10 which contains an NdeI site at the 3' terminus of the modified 12 kD FBD was used to construct a plasmid, designated pFN 202-5, which encodes the modified 12 kD FBD fused to the 33 kD cell binding domain (CBD). This construction was performed as shown in FIG. 12 where the 33 kD CBD fragment was taken from plasmid pFN 137-2 (deposited in the ATCC under ATCC Accession No. 67910). Plasmid pFN 202-5 was transformed to *Escherichia coli* strain A1645 and thence to *Escherichia coli* strain A4255 and is a good expressor (8% of total protein). The 45 kD polypeptide consists of the 12 kD' FBD fused to the 33 kD CBD (first 109 amino acids of FBD followed by amino acid residues histidine and methionine followed by the CBD commencing with serine. An additional methionine residue is present at the N-terminus of the final polypeptide).

D. Expression of a 31 kD FBD polypeptide fused to the amino acid sequence DGRGDS In order to obtain expression of a 31 kD FBD polypeptide fused at the carboxy terminus to the sequence asp-gly-arg-gly-asp-ser (DGRGDS) (SEQ ID NO. 4) the following construction was made. Plasmid pFN 975-25 which expresses the 31 kD FBD was digested with PvuII and HindIII and ligated to a synthetic linker as shown in FIG. 13. The resulting plasmid, designated pFN 195-4, was used to transform *Escherichia coli* strain A1645 and thence *Escherichia coli* strain A4255. These cells were found to be good expressors of the 31 kD-DGRGDS polypeptide, at levels of about 8% of total cellular protein. The sequence of this polypeptide is described in the description of FIG. 13.

E. Expression of a fused 31 kD FBD-33 kD CBD

In order to obtain expression of a "full length" r31 kD FBD polypeptide fused to the r33 kD CBD the following construction was made.

Plasmid pFN 975-25 which expresses the 31 kD FBD was digested with PvuII and HindIII, and the large fragment resulting was ligated to a synthetic linker and to the r33 kD cell binding domain obtained from plasmid pFN 137-2 after NdeI and HindIII digestion (as shown in FIG. 14). The resulting plasmid, designated pFN 194-2, encodes the r31 kD FBD linked to the 33 kD CBD. Plasmid pFN 194-2 was transformed to *Escherichia coli* strain A1645 and then to *Escherichia coli* strain A4255, and the resulting cells were low expressors of a 64 kD polypeptide which comprises the 31 kD FBD fused to the 33 kD CBD. The sequence of this polypeptide is described in the description of FIG. 14.

Fermentation and growth conditions

The clone expressing the r12 kD FBD polypeptide was fermented in rich medium (yeast extract and casein hydrolysate) containing ampicillin. Growth was carried out at 30° C. Expression was obtained upon induction at 42° C. for 2 hours and subsequently bacterial cell cake containing the r12 kD FBD polypeptide was obtained. Similarly, cell cake containing other proteins described above was obtained.

F. Additional Plasmid Construction 1. 18.5 kD FBD polypeptide fragment: As described above, (Example 2A) the 20 kD FBD fragment expressed by plasmid pFN 949-2 (ATCC No. 68456) contains up to 20 additional amino acids of the pBR 322 vector due to readthroughpast the end of the FN gene in the absence of a properly located TAA transcription termination codon. In order to provide a more authentic "3 fingered" FBD polypeptide fragment than the 20 kD fragment described in Example 2A, a plasmid encoding an 18.5 kD FBD polypeptide was constructed.

The construction is shown in FIG. 23 and described in the Description of the figures. The resulting plasmid designated pFN 208-13 expresses an 18.5 kD FBD polypeptide fragment under control of the $P_L$ promoter and the β-lactamase ribosomal binding site. Plasmid pFN 208-13 was deposited in ATCC in *E. coli* A4255 under Accession No. 68456. This plasmid expresses the first 154 amino acids of fibronectin with an additional N-terminal methionine.

2. Improved expressor of the 12 kD FBD polypeptide fragment: Plasmid pFN 196-2 (ATCC No. 68328) expressing a 12 kD FBD polypeptide fragment (2 "fingers") under control of the $\lambda P_L$ promoter and β-lactamase ribosomal binding site was described above. In order to further improve the level of expression of the 12 kD fragment, plasmid pFN 203-2 was constructed as shown in FIGS. 26 and 27 and described in the description of the figures. Plasmid pFN 203-2 expresses the 12 kD fragment under control of the $\lambda P_L$ promoter, CII ribosomal binding site and a 36 bp trp transcription termination sequence. Plasmid pFN 203-2 was deposited in ATCC in *E. coli* A4255 under Accession No. 68606. These transformed cells were found to be good expressors of the 12 kD FBD polypeptide fragment in amounts comprising about 12–18% of the total cellular protein.

3. High Expression of fused 31 kD FBD - 33 kD CBD Poltpeptide: Plasmid pFN 194-2, a low-level expressor of a 64 kD fused FBD-CBD polypeptide under control of $\lambda P_L$ promoter and β-lactamase ribosomal binding site was described above. A plasmid was constructed to enable high level expression of the 64 kD polypeptide under control of the $\lambda\ P_L$ promoter, CII ribosomal binding site, and 36 bp trp transcription termination sequence. This plasmid, designated pFN 205-5 was constructed as shown in FIG. 25 and described in the description of the figures.

Fermentation and growth conditions for all these expression plasmids (1-3 above) were essentially as described for production of the other FBD polypeptides (see Example 2C). Purification and refolding were as described in Example 5 and Example 10.

Example 5

Refolding and Purification of Recombinant 20 kD and 12 kD Fibrin-Binding Polypeptides of Fibronectin.

The process for refolding and purification of the r20 kD and r12 kD polypeptides is made up of three stages:
1. Crude processing of the bacterial cake.
2. Refolding/reoxidation.
3. Purification.
   1. Crude processing
   1.1 Washing and extraction of the pellet: The bacterial cell cake, obtained as described in Example 2 for the r20 kD polypeptide and as described in Example 4 for the r12 kD polypeptide, is disrupted and washed essentially as for the r31 kD polypeptide (see coassigned PCTPublication No. WO 90/07577, page 121 et seq.); however, changes were introduced in the extraction procedure used for both the r20 kD and the r12 kD polypeptides. The following is an example of the washing and extraction procedure performed on the bacterial cell cake of the r20 kD polypeptide; the r12 kD polypeptide is extracted in a similar way.
   1.2 procedure: Bacterial cake containing the r20 kD polypeptide was produced as described in Example 2 by fermentation of *Escherichia coli* strain A4255 harboring plasmid pFN 949-2. A portion of this bacterial cake (14.8 g) was suspended in 10 volUmes of 50mMTris HCl, 50 mM EDTA (Buffer B), pH 7.5. The suspension was homogenized for 15–30 seconds at a medium speed, sonicated 3 times for 4 minutes with pulsing, and centrifuged at 15,000 rpm for 30 minutes. The pellet was resuspended in 2.4 volumes (36 ml) of Buffer B. Lysozyme (0.1 mg/ml) was added and the suspension was 5 incubated in a water bath at 37oC for 2 hours with stirring. Triton X-100 was added to a final concentration of 1%, stirred at room temperature for 30 minutes and centrifuged. The pellet was resuspended three times in 148 ml of water (i.e., 10 times the volume of the original pellet), homogenized, stirred for 30 minutes at room temperature and centrifuged. The final pellet weighed approximately 1.5 g, i.e., only 10% of the original weight; however, both the r20 kD and the r12 kD polypeptides stay in the pellet, as evidenced by SDS-polyacrylamide gel-electrophoresis. The washed and extracted pellet was kept frozen at −20° C. until further processed.

2. Solubilization and refolding of the extracted pellet
   2.1 The reagents and procedure used for the refolding/reoxidation are different in this case from those used for the r31 kD polypeptide. The extracted pellet of the r20 kD or the r12 kD polypeptide is dissolved in 6M guanidine-HCl (GuCl) in the presence of 50 mM β-mercaptoethanol and, following a tenfold dilution, is allowed to reoxidize by air.
   2.2 Procedure: The frozen r20 kD pellet (1.5 g) was solubilized and homogenized in 10 volumes of 10mMTris HCl, 5 mM EDTA (Buffer C), pH 8.0, containing additionally 6M Guanidine-HCl. The sample was reduced by the addition of 57 μl of undiluted β-mercaptoethanol (final concentration: 50 mM) and stirred in the absence of air, i.e., in a sealed container, for 30 minutes. It was then dripped at the rate of about 5 ml/min into 10 volumes (148 ml) of Buffer C, pH 8.0 and allowed to oxidize while being constantly and gently stirred, in an open beaker for 48–72 hours at room temperature. Alternatively, the oxidation was performed in a closed container in the presence of 0.3 mM GSSG. Although at this stage some polypeptide precipitation had already occurred, the suspension, including the precipitate, was dialyzed over 24 hours against 15 volumes of Buffer C, pH 8.5 with three changes of buffer. The dialysate was then subjected to centrifugation for 45 minutes at 15,000 rpm (22,500×g) in a high-speed Beckman centrifuge equipped with a JA-17 rotor. This removes many contaminant proteins and aggregates of the r20 kD or r12 kD, which have been produced during reoxidation.

3. purification and Characterization

Since the location of the heparin binding site within the fibrin binding domain was not known, it therefore could not beknown in advance if the new shorter r20 kD and r12 kD polypeptides would bind to Heparin-Sepharose. However, we found that the shorter molecules did in fact bind to Heparin-Sepharose.

We found that there was no need for a phenyl-Sepharose column, as in the case of the r31 kD, in order to purify the reoxidized r20 kD or r12 kD polypeptides. In fact, the material could be directly purified on Heparin-Sepharose, but considerable improvement, with respect to removal of contaminants, incorrectly folded molecules and dimers, was achieved when the sample was chromatographed on a Q-Sepharose column before chromatography on a Heparin-Sepharose column. In some cases, the polypeptide was concentrated on a Pellicon system (Millipore Corp.), using membranes with appropriate cut-off points, i.e., 10 kD for the r20 kD polypeptide and 3 kD for the r12 kD polypeptide, prior to being loaded on the Q-Sepharose column. The Heparin-Sepharose column is also used for concentration of both polypeptides. The following is an example of the purification procedure used in the case of the r20 kD polypeptide.

3.1. O-SeDharose Chromatography: One-third of the reoxidized r20 kD (47 ml) was applied to a 10 ml column of Q-Sepharose Fast Flow column, which had been pre-equilibrated in Buffer C, pH 8.5 at 1.2 ml/min flow-rate. The flow-through fraction was collected and saved (70 ml). The polypeptides which adhered to the columnwere eluted with Buffer C, pH8.5 containing 0.5M NaCl and the column was regenerated with 0.5M NaOH.

3.2 Heparin-Sepharose Chromatography.: The flow-through from the Q-Sepharose column was applied to a 10 ml column of Heparin-Sepharose pre-equilibrated in pH 8.5 buffer at a flow rate of 0.5 ml/min. The flow-through fraction contained mostly contaminants and incorrectly folded r20 kD polypeptide. The purified (>95% pure) r20 kD polypeptide was eluted in Buffer C, pH 8.5 containing 0.5M NaCl and the colEwas regenerated in the same buffer containing additionally 6M Guanidine-HCl. Representative purification tables for the r20 kD (Table A) and r12 kD (Table B) polypeptides are provided.

3.3 Characterization: Supernatants from the processing of the bacterial cake for both ther20 kD and the r12 kD polypeptide, as well as aliquots from subsequent column fractions, were assayed for polypeptide and analyzed by SDS-polyacrylamide gel electrophoresis; their elution profiles were obtained on a Superose 12 column attached to either a FPLC or a HPLC. These profiles at various stages of the refolding, as well as of the purification, are shown for the r20 kD (FIG. 21) and the r12 kD (FIG. 22). The purified r20 kD or rl2 kD polypeptides elute as single sharp bands. These profiles corroborate the results seen on SDS-PAGE gels under non-reducing conditions; the bands of both the 20 kD and the r12 kD polypeptides samples are non-diffuse, indicating a single molecular form. In the case of the r20 kD, the band of the non-reduced polypeptide runs (as in the case of the r31 kD polypeptide) faster than that of the reduced form; this is a similar effect to that seen in the case of the kD polypeptide. However, no such difference is observed in the case of the r12 kD polypeptide. Additional details on characterization of FBD polypeptides are provided in Example 11.

These FBD polypeptides are available for radiolabeling in order to use them as radiopharmaceuticals for imaging of thrombi and atherosclerotic lesions.

The advantages of using the smaller FBD polypeptides (r20 kD and r12 kD) for the above-mentioned purposes as opposed to using the larger r31 kD polypeptide is that we have developed after considerable .effort a simpler method for the preparation of the smaller molecules, i.e., the methods described above for the refolding and purification of the r20 kD and r12 kD polypeptides are faster and easier than the method for refolding and purification of the r31 kD polypeptide. In addition, these methods result in a higher yield than does the method for the r31 kD polypeptide and a higher concentration of polypeptide can be achieved for the shorter FBD polypeptide fragments (up to 10mg/ml).

An improved embodiment of this method for refolding and purification of the FBD polypeptide fragments is described in Example 10.

TABLE A

PURIFICATION OF THE r20 kD FBD

| Step | Volume (ml) | Protein Conc (mg/ml) | Total Protein (mg) | Purity[a] (%) | Amount of FBD (mg) | Yield (%) | Degree of purification |
|---|---|---|---|---|---|---|---|
| Solubilized & Reduced Pellet | 14.8 | 12.4 | 183.5 | 35 | 64.2 | 100 | 1 |
| Oxidized Supernatant | 148 | 0.72 | 106.5 | 45 | 48.0 | 74.7 | 1.3 |
| Oxidized Supernatant (½) | 47 | | 33.8 | | 15.2 | | |
| Q-Sepharose Flow-through | 70 | 0.20 | 14.0 | 80 | 11.2 | 54.9 | 2.3 |
| Heparin-Sepharose 0.5 M NaCl | 9 | 0.71 | 6.1 | 98 | 6.0 | 29.4 | 2.8 |

[a]Estimated from either SDS-PAGE gels under reducing conditions or from Sepharose 12 elution profiles.

This is a representative purification table for the refolding and purification of the r20 kD polypeptide, processed as described in Example 5, Sections 2 and 3.

TABLE B

PURIFICATION OF THE r12 kD FBD

| Step | Volume (ml) | Protein Conc (mg/ml) | Total Protein (mg) | Purity[a] (%) | Amount of FBD (mg) | Yield (%) | Degree of purification |
|---|---|---|---|---|---|---|---|
| Solubilized & Reduced Pellet | 100 | 6.66 | 666 | 10 | 66.6 | 100 | 1 |
| Oxidized[b] Supernatant | 500 | 0.20 | 100 | 58 | 58.0 | 87.1 | 5.8 |
| Q-Sepharose Flow-through | 500 | 0.13 | 65 | 80 | 52 | 78.1 | 8.0 |
| Heparin-Sepharose 0.5 M NaCl | 14 | 0.75 | 10.5 | 98 | 10.3 | 15.4 | 9.8 |

[a]Estimated from either SDS-PAGE gels under reducing conditions or from Sepharose 12 elution profiles.
[b]Concentrated on a Pellicon system.

This is a representative purification table for the refolding and purification of the r12 kD polypeptide, processed as described in Example 5, Sections 2 and 3.

Example 6

Biological Activity of the r31 kD, r20 kD and r12 kD Fibrin Binding Domain Polypeptides The biological activity of the r31 kD FBD was described in coassigned PCT Publication No. WO 90/07577, page 134 et seq. relating to its binding to fibrin clot in vivo and in vitro, binding to bacteria and binding to extracellular matrix. In this example, additional results relating to the r31 kD polypeptide are presented and the biological activity of the 20 kD and 12 kD FBD polypeptides is demonstrated.

In this Example the binding of the recombinant fibrin binding domains to fibrin clots was measured as follows: Binding of $^{125}$I-rFBD (r31 kD, r20 kD or r12 kD) to a preformed fibrin clot (two-step Reaction II)

Step 1 Formation of fibrin clot: This may be done in one of two ways:

Either (a) Incubation at 37° C. of 20 μl citrated human whole blood with 5 mM $CaCl_2$, 1 unit/ml thrombin and PBS in a final volume of 250 μl. The reaction is terminated after 45 minutes bycentrifugation and washing of the pellet (twice) with 1 ml PBS;

or (b) Incubation at 37° C. of 20 μl non-citrated whole human blood ("naive" blood). The reaction is terminated after 150 minutes by centrifugation and washing as in (a).

Step 2 Binding of the $^{125}$I-FBD polypeptide to the preformed fibrin clot Clots are incubated at 37oC in a final volume of 250 μl PBS with 125I-rFBD polypeptide. Other constituents may be added as indicated for each experiment. The binding reaction is terminated after 45 minutes by centrifugation and washing three times with PBS. The tubes containing the $^{125}$I-rFBD - fibrin pellet were measured for radioactivity in a gamma counter.

Results

A. Metabolic stability of $^{125}$I-labeled 731 kD FBD in rats: ex-vivo binding to fibrin versus TCA insolubility As described in the description of FIG. 18, rats were injected intravenously with r31 kD FBD labeled with $^{125}$I and blood samples taken at intervals were added to Na citrate. Aliquots of the blood were treated as follows: either (a) treated with 20% TCA and the TCA insoluble counts were measured; or (b) incubated with preformed clot (using 20 μl whole blood from control rat); binding of the $^{125}$I-31kD FBD to preformed clot was measured under the conditions of the two-step Reaction II described above.

The radioactivity was measured by a gamma counter and the activity of each sample was calculated as a percentage of total cpm present in the reaction mixture.

The results demonstrated in FIG. 18 indicate a good correlation between the physical decay of the r31 kD (as measured by the decrease in TCA insolubility) and the functional decay (as measured by the decrease in ex-vivo binding of the r31 kD to a preformed fibrin clot.) However, at the initial stage of the comparative studies there are marked differences; at 30 min. the functional decay is several fold higher than the physical decay. These results, which suggest a much faster decrease of functional stability than physical degradation, can be explained since the main site for the covalent reaction of the FBD with the fibrin clot is the glutamine residue located at the extreme amino terminus of the FBD molecule at amino acid no. 3; this glutamine residue, being located in a 20 amino acid stretch outside the Type 1 homologystructure, is not protected from degradation by the tertiary structure, which is typical of the rest of the FBD domain.

B. Specificity of binding of r31 kD to fibrin: effect of transglutaminase

The covalent binding of the fibrin binding domain of plasmatic fibronectin to fibrin in a clot is mainly due to the reaction of amino acid no. 3 of fibronectin (glutamine) with fibrin; this binding reaction is enzymatically controlled bythe enzyme transglutaminase which specifically recognizes the amino acid sequence containing this glutamine residue.

The following experiment was performed to investigate if transglutaminase is involved in the binding of the recombinant r31 kD FBD to clots. All the exogenous transglutaminase used in the experiments described in this application is guinea-pig liver transglutaminase (Sigma).

The binding of 0.3 μM solution of the following molecules to preformed fibrin clot derived from 20 μl of whole human blood was measured in the presence and absence of transglutaminase using the two-step Reaction II described above: $^{14}$C-putrescine-r31 kD FBD, $^{125}$I-r31kD FBD and $^{125}$I-recombinant bovine growth hormone (control). The $^{14}$C-putrescine-r31 kD protein complex where the glutamine residue at position 3 is blocked by covalent reaction with $^{14}$C-putrescine, was prepared as follows:

A solution containing 3 μM r31 kD FBD, 10 mM $CaCl_2$, 0.015 units/ml transglutaminase and 60μM $^{14}$C putrescine (specific activity 100 mc/mmole) was incubated at 37° C. for 5 hours. The amount of $^{14}$C-putrescine incorporated into the 31 kD FBD was measured by TCA precipitation of an aliquot of this reaction solution and demonstrated the incorporation of an equivalent amount to 2.8–3 μM solution of $^{14}$C-putrescine into the r31 kD protein; this indicates that more than 90% of the glutamine at position number 3 of the FBD covalently reacted with the 14C-putrescine. The 14C-putrescine r31 kD material was stored at 0° C. and used within a few days without further treatment. The r31 kD FBD and the control recombinant bovine growth hormone analog (bGH) prepared as described in EPO Publication No. 131843 were labeled with 125I using the ICl method described in Example 3.

Results

The counts bound in the two-stepReaction II in the presence and absence of transglutaminase were obtained and the ratio of counts bound in the presence and absence of transglutaminase was calculated for each polypeptide tested. This ratio differs dramatically when intact 31 kD FBD is compared to putrescine-FBD ("blocked" FBD) or to the control bGH. In the two latter cases the ratio of counts is close to 1 which shows that transglutaminase does not affect the binding and total cpm present in the clot is 10–15% of total cpm in the reaction). In the case of the intact 31 kD FBD the ratio is dramatically higher than I (in different experiments the ratio varied between 1.8–7 depending on the quality and freshness of the blood and the transglutaminase) and total cpm present in the clot is 40–70% of total cpm in the reaction) i.e., transglutaminase greatly increased the binding of r31 kD polypeptide to the clot.

These results indicate the strong effectiveness of unblocked glutamine at position number 3 for the binding of the r31 FBD polypeptide to the fibrin clot in the presence of transglutaminase.

Other experiments have shown that the addition of transglutaminase to the two-step Reaction II increases the binding of the r20 kD and r12 kD polypeptides to the clot, comparable to the effect observed with the r31 kD.

C. Characterization of r31 kD FBD-fibrin complex by SDS polyacrylamide gel electrophoresis In order to determine the size of complex formed by the binding of r31 kD to a fibrin clot the following series of experiments was undertaken. Clots were derived from either 20 μl whole human blood (A) or 250 μl of a solution of 0.8 μM human fibrinogen (B). In some of the fibrinogen experiments dental coils (as described in Example 7) were added to the tubes together with the fibrinogen.

The binding of $^{125}$I-r31 FBD to the fibrin clot was measured using the two-step Reaction II described above, in the presence of 0.15 μM $^{125}$-r31 kD FBD and 5 mM $CaCl_2$. The reaction was terminated by three times washing with PBS. The pellet, after the various treatments described below, was centrifuged and 15 μl aliquots of the supernatant (i.e., the soluble material) were electrophoresed on polyacrylamide gels which separates the material of molecular weight $>10^6$ from molecular weight $>10^5$ and from lower molecular weight materials. An autoradiogram was produced which shows the following: in the presence of transglutaminase high molecular weight forms of r31 kD—fibrin complex appear which are resistant to boiling in the presence of the strong ionic detergent SDS and β-mercaptoethanol, which reduces S-S bonds.

Additionally, when 4M urea is included in the boiling reaction the very high molecular weight forms (>$10^6$) are quantitatively converted to the intermediate molecular weight forms (>100,000) as expected for hydrophobic bonded aggregates of high molecular weight fibrin clots. The amount of free r31 kD polypeptide in the clots is normally small; this is the material released on boiling with phosphate-saline buffer only. The resistance of the intermediate molecular weight forms to additional treatment with urea supports the involvement of a covalent linkage between the $^{125}$I-r31 kD and the fibrin.

D. Effect of fibronectin and heparin on the binding of $^{125}$-r31kD to preformed fibrin clots (i) Effect of fibronectin (FN)

Human plasma contains substantial levels of FN (300 μg/ml) which potentially could compete with the binding of $^{125}$I-r31 kD polypeptide to preformed clots. Such competition may affect the efficiency of clot radiolabeling and subsequently the imaging process. To examine the effect of FN, $^{125}$I-r31 kD (0.15 μM) was added together with purified FN (1 μM) to a preformed clot in PBS. Although FN was added in a molar excess of 7 relative to $^{125}$I-r31 kD, the binding of the latter polypeptide was only slightly affected (20% inhibition). The observation that excess FN does not compete with $^{125}$I-r31 kD binding could be interpreted in two ways: the number of sites for crosslinking onto the clot is in excess to accommodate both FN and $^{125}$I-FBD, or the affinity of FBD to the clot is much higher than that of FN. Based on several observations, we believe that both excess binding sites and higher affinity of the $^{125}$I-r31 kD enable its binding to the clot in the presence of plasma concentrations of FN.

(ii) Effect of heparin

Some radioscintigraphic agents such as $^{111}$In-labeled platelets and labeled fibrinogen are ineffective in the presence of therapeutic heparin. It was important, therefore, to analyze the effect of heparin on the incorporation of $^{125}$I-r31 kD to the clots. The results showed that heparin has no significant effect on the binding of r31 kD FBD to preformed clots. Other experiments showed that the same amount of heparin affects dramatically the binding of r31 kD to a fibrin clot during its formation, i.e., Reaction I.

E. Comparison of the binding of various recombinant FBD polypeptides and plasmatic FBD to preformed clots To compare the binding to preformed clots of the various recombinant FBD polypeptides (r31 kD, r20 kD and r12 kD) and plasmatic 31 kD FBD, a series of experiments using the two-step Reaction II was carried out as described in FIG. 19. The results show that the plasmatic 31 kD binds to a similar level as the r31 kD whereas the r20 kD and r12 kD polypeptides both bind at about half the level of the larger (31 kD) molecule. The level of binding of the r20 kD and r12 kD polypeptides is still sufficiently high to demonstrate the potential of radiolabeled r20 kD and r12 kD polypeptides as radiopharmaceuticals for thrombus imaging. Similar experiments using the r31 kD-DGRGDS polypeptide (Example 4, D and FIG. 13) showed that it binds at about the same level as the r31 kD.

F. Binding of $^{125}$I-r12 kD to fresh or frozen clots

In order to study the effect of freezing the clots prior to use in binding experiments with FBD polypeptides, the following experiment was carried out. Fibrin clots were either used fresh or after storage at −70° C. in a two-step Reaction II binding experiment with $^{125}$I-r12 FBD, prepared as described in Example 5.

The experiment was carried out as described in the Description of FIG. 15 (SEQ ID NOS. 31–38)in the presence or absence of transglutaminase. FIG. 20 shows that there is little significant effect of freezing on the abilities of clots to bind r12 kD FBD. Normally, frozen clots without added transglutaminase yield binding results similar to fresh clots in the presence of transglutaminase; there is no effect on the binding reaction when exogenous transglutaminase is added to frozen clots, probably because of the release of endogenous transglutaminase from the frozen red blood cells.

As noted in Section B above, there is a wide range of response to addition of exogenous transglutaminase in Reaction II.

G. Conditions for binding of $^{125}$I-r31 kD FBD to preformed clots

To investigate the conditions for binding of $^{125}$I-r31 kD to preformed clots, the following series of experiments were carried out. The binding of $^{125}$I-r31 kD polypeptide to preformed clots formed from citrated or "naive" blood was examined, using the two step Reaction II method, and in the presence or absence of various constituents (calcium, hirudin, transglutaminase). The pattern of results using the "citrated" blood or "naive" blood clots is similar although the binding of the r31 kD polypeptide is higher to citrated blood.

Hirudin (Sigma) is a specific inhibitor of any thrombin-mediated reaction and the hirudin was therefore added in order to investigate the effect of thrombin on the binding reaction (step 2). No effect of hirudin was shown and therefore thrombin has no effect on the binding of the r31 kD polypeptide to the clot. However, the same amount of hirudin totally inhibits the binding when added at step 1 where fibrin is formed from fibrinogen, as was expected.

These results also show that exogenous transglutaminase increases the binding of r31 kD FBD to clots and furthermore that this transglutaminase reaction is dependent on the presence of calcium ions. Since the exogenous transglutaminase used is tissue transglutaminase (in its active form) we expect that the serum transglutaminase, factor XIII, which has to undergo activation by thrombin to form factor XIIIa, will be highly sensitive to hirudin inhibition.

H. Conditions for binding $^{125}$I-r31 kD FBD to the extracellular matrix (ECM)

The binding of $^{125}$I-r31 kD to the extracellular cell matrix of endothelial cells (ECM) was demonstrated in coassigned PCT Publication No. WO 90/07577, page 144. The binding was now further characterized by examination of the binding of 0.3 μM $^{125}$I-r31 kD FBD to ECM in the presence and absence of exogenous transglutaminase; additionally the binding in the presence of transglutaminase was examined in the presence of each of heparin, fibronectin or spermidine.

The results of these experiments demonstrate that the binding of the r31 kD FBD to ECM is increased by the addition of transglutaminase. Heparin has no significant effect on the binding whereas spermidine, a known inhibitor of transglutaminase, inhibits the binding. Collagen also inhibits the binding, suggesting the possible involvement of collagen as an acceptor molecule on the matrix of the endothelial cells. Fibronectin has little effect on the binding reaction.

These results give more support to the potential use of radiolabeled recombinant FBD polypeptides as radiopharmaceuticals for imaging the initial plaque formation in denudated blood vessels.

Further experiments demonstrating the biological activity of various polypeptide fragments of the FBD of fibronectin are described in Example 9.

Example 7

Uptake of Recombinant $^{125}$I-31 kD FBD and Fragments Thereof by Stainless Steel Coil-Induced Venous Thrombi in Rats The stainless steel coil-induced venous thrombus model in rats was used to study the uptake of labeled r31 kD, r20 kD and r12 kD FBD polypeptides. The model employed was as described by Maffrand et al. [Thrombosis and Haemostasis 59: 225–230 (1988) ].

Experimental Details

A. Investigation of the uptake of $^{125}$I-31 kD by the stainless steel coil-induced venous thrombus Wistar-derived female rats (200-250 g) were anaesthetized by Ketamine HCl plus Xylazin HCl. A midline abdominal incision was made and the inferior vena cava was exposed. A stainless steel wire coil (a dental paste carrier, fine No. 31, 21 mm long) was inserted into the lumen of the vein at the site just below the Junction, and the incision was sutured. Each inserted device was individually weighed before insertion and each weight recorded. Three hours after the operation, the animals were given an i.v. injection of 1 ml of 0.9% NaI solution in order to saturate the thyroid iodide pool. One hour later, the rats received an i.v. injection of $^{125}$I-r31 kD FBD (5×10$^6$ cpm; 100 µg/kg). The r31 kD polypeptide was labeled as described in Example 3. At 24 hours after the administration of the labeled polypeptide, blood was drawn by cardiac puncture, and the rats were sacrificed. The segment of the vein carrying the coil was removed while taking care to drain away all residual blood. In one group, the segments carrying the coil were weighed as such and taken for measurement of radioactivity (the "Thrombus in Situ" group). In another group the vein sections were incised longitudinally, and the coils carrying the thrombi were carefully removed, weighed and the radioactivity was measured. The blood radioactivity levels were measured using peripheral blood.

Calculation of the results:

In the two groups, the initial weight of each coil was subtracted from its final weight, and the specific radioactivity in each case was calculated by division of the cpm value by the net weight. The specific activity of the peripheral blood samples was also calculated.

Results:

At 24 hours, the blood levels of radioactivity were around 5000–10,000 cpm/g, while in the isolated blood clot the specific radioactivity was around 300,000 cpm/g, i.e., 30 to 60 fold higher (see FIG. 16). When the entire segment of the vein carrying the clot was included in the analysis, and a so-called "specific radioactivity" value calculated, the resultant values were 4–5 fold higher than those of the blood, thus indicating that a good signal-to-noise ratio may be obtained for gamma-camera imaging of blood clots in vivo using labeled r31 kD FBD.

The effect of heparin pretreatment was studied in this model. This kind of experiment is essential because patients that are candidates for thrombus imaging are usually treated with this anticoagulation agent. In order to study this question, a group of rats were treated with heparin (500 units/rat intravenously) 10 minutes before administration of the labeled polypeptide. This treatment of heparin did not affect the uptake of label, as measured 24 hours later.

These results demonstrate that thrombus imaging using the FBD of FN may be done in the presence of heparin.

B. Comparison of recombinant 12 kD, 30 kD and 31 kD-FBD polypeptides in the stainless steel coil-induced venous thrombus model The three recombinant polypeptides were labeled with $^{125}$I as described in Example 3 and utilized in the rat model as described in A above. The results, shown in FIG. 17, indicate that each of the three molecules was specifically localized in the clots as compared to the blood, by comparing the specific radioactivities; the specific radioactivity of the clots appeared to be higher with the longer molecules than the shorter polypeptides (143,000, 78,500 and 63,000 cpm/g clot for the r31 kD, r20 kD and r12 kD polypeptides, respectively), but the differences were not statistically significant. The specific radioactivity values for blood (after 24 hours) were similarly related to the molecular size (7040, 5016 and 3300 Cpm/g for the r31 kD, r20 kD and r12 kD polypeptides, respectively) and might reflect differences in the blood clearance rates of these molecular species. Hence, the calculations of the ratio of clot to bloodspecific radioactivity resulted in values that were similar for the three different polypeptides, and ranged around 20. These results suggest that all three FBD species (or other fragments of the FBD) could serve for thrombus imaging.

Example 8

Labeling of the fibrin binding domain polypeptides for imaging atherosclerotic lesions and thrombi The fibrin binding domain polypeptides described in this application (the r31 kD, the r20 kD and the r12 kD polypeptides), or other polypeptide fragments of the FBD, may be radioactively labeled to carry a radiotracer to a thrombus in order to permit its external detection by gamma camera imaging. This application discloses in Example 3 the labeling of these three polypeptidesbymeans of iodine-$^{125}$ ($^{125}$I), which has a long half life of 60 days.

Another radioiodine is iodine-131 ($^{131}$I) which may be used to label the FBD polypeptides using known methods such as described by Uehara et al (1). However, $^{131}$I also has a relatively long half life of 8 days.

Optimally, a radiopharmaceutical for clinical imaging of atherosclerotic lesions and thrombi should yield positive results within the first few hours after injection (33). For such a test a shorter lived radiolabel could be used. Recent studies have suggested that indium-111 ($^{111}$In) or technetium-99m ($^{99m}$Tc) may be more suitable as radiotracers, since they have half-life of 67 hours and 6 hours, respectively (32); another short-lived low energy label is iodine-123 ($^{123}$I) with a half-life of 13.3 hours.

The labeling of the FBD polypeptides by $^{99m}$Tc may be carried out using known methods (21, 33, 34, 35). $^{99m}$Tc is a very suitable diagnostic single photon radionuclide because of its short half-life, a detection level of 140 KeV with the gamma counter, no particulate radiation and inexpensive, convenient availability. These attributes allow the routine administration of doses of 30 m Ci that result in high photon-flux levels facilitating lesion detection by single photon emission computerized tomography (32, 35).

Other radiolabels which may be used to label the FBD polypeptides include krypton-81m (SlmKr) and xenon-133 ($^{133}$Xe), which has a half-life of 5.3 days, as reviewed by Knight (4). Another potential radiolabel is gallium-67 (67Ga) as described by Yamamoto (36); $^{67}$Ga has a half-life of 78 hours.

We have labeled the r31 kD, r20 kD, r18.5 kD and r12 kD polypeptides and the plasmatic 31 kD fragment by means of $^{111}$In using the method described for human serum albumin by Hnatowich, D. J., Layne, W. W. and Childs, R. L. in J. Appl. Radiat. Inst. 33: 327 (1982). Preliminary experiments have shown that the labeled FBD polypeptides bind to preformed thrombi in vitro, measured by the two-step Reaction II (Example 6) and to thrombi in vivo measured by the model described in Example 7, and giving a high thrombus:blood ratio in the range of 80–200 after 24 hours.

Radiolabeling of the 12 kD and 18.5 kD proteins

DTPA modification of the 12 kD and 18.5 kD polypeptide fragments of the FBD was performed, essentially according to published methods (Hnatowich, D. J. Layne, W. W. and Childs, R. L. (1982) Int. J. Appl. Radiat-Isot. 33 327–332; Knight, L. C. Kollman, M, Maurer, A. H. and Budzynski, A. Z (1987) Biochim, Biophys. Acta 924 45–53), using the cyclic anhydride of DTPA. Aliquots of a dry chloroform solution, containing calculated amounts of DTPA equivalents, were evaporated and reacted with the proteins, in either phosphate—or bicarbonate—buffered saline (pH 7.4 and 8.0±0.2, respectively). Excess of (hydrolyzed) DTPA was removed byexhaustive dialysis. Labeling was performed with carrier-free $^{111}$In in a HCl solution neutralized to about pH 6 with sodium acetate. In one experiment (in PBS) the 12 kD polypeptide produced as described in Example 5 was labeled and this resulted in a thrombus to blood ratio (in the rat model) of 86 (see below), a calculated molar excess of DTPA—over the 12 kD protein—of 5 was employed (there are 5 lysyl εamino groups and 1α amino group in the 12 kD protein). Upon labeling with $^{111}$In, free (unbound) $^{111}$In was estimated to be below 15% (by TLC).

In another set of experiments (in BBS), a 1:1 ratio between DTPA anhydride and either the 12 kD or 18.5 kD protein was employed.

In order to estimate the number of DTPA residues incorporated per molecule of 12 kD, DTPA-modified protein (before separation of the excess of DTPA) was labeled with $^{111}$In (Knight et al., see above). The number of DTPA residues incorporated was found to be 0.12 per molecule of 12 kD. The DTPA-labeled 12 and 18.5 kD proteins had identical Supsrose 12 (gel-filtration) slution profiles as those of the control unmodified protein (retention times of 19.17 min and 18.29 min, respectively - control values are in Table E). Upon labeling with 111In, after separation of excess DTPA, the amount of free (unbound) 111In was found to be 28 and 29% for the 12 and 18.5 kD proteins, respectively, which resulted in thrombus to blood ratios (in the rat model) of 27 and 25, respectively.

NMRI, ultrasound and X-ray imaging with metal chelates are described in U.S. Pat. No. 4,647,447. In addition, antibody coupling with metal chelates is mentioned at column7, line 42. Monoclonal antibodies labeled with polymeric paramagnetic chelates and their use in NMRI methods have also been described [Shreve, P. et al., Magnetic Resonance in Medicine 3: 336–340 (1986) and Brady, T. et al. in Proceedings of the Society of Magnetic Resonance in Medicine, SecondAnnual Meeting, Soc. of Magnetic Resonance in Medicine, Inc., San Francisco, p 10, 1983 referenced by Koutcher, J. et al., J. Nucl. Med. 25: 506–513 (1984)].

Example 9

Additional Experiments Demonstrating Biological Activity of Various FBD polypeptides The biological activity of the r31 kD, r20 kD, r12 kD FBD polypeptides has been described in Example 6. This example will disclose additional results observed using the FBD polypeptide fragments; these are the 12 kD obtained as described in Examples 4 and 5, and the 18.5 kD constructed, oxidized/refolded, and purified as shown in Examples 4 and 10.

I. Binding to Fibrin Clot

The clot formation and FBD binding were performed as described below in a modified version of the two-step reaction II described in Example 6. To avoid artifacts of aggregation and precipitation of the FBD polypeptides, the final centrifugation step is eliminated and the clot is transferred to a new tube and then extensively washed.

a. Clottint of "preformed clot"

Reaction mixtures (300 µl ) prepared in siliconized plastic vials (7 ml) of the gamma counter, contained 150 µl of Mix I [0.2×Tyrode's buffer ("b 1×Tyrode's Buffer": 1 mM Hepes pH 7.35; Dextrose 0.2%; 27 mM NaCl; 0.76 mM $NaH_2PO_4$; 0.54 mM KCl1; 0.2 mM $MgCl_2$), 3U/ml Thrombin (Sigma), 0.6% BSA (Sigma), 15 mM $CaCl_2$, 150 mM $NaCl_2$, mM $NaHCO_3$, pH 8.0] and 150 µl fresh citrated whole human blood.

Protocol: Incubation at 37° C. for 3 hrs. The serum is removed by vacuum, and the tubes containing the fibrin clot are kept frozen at −70° C. Preformed clots can be used for several months.

b. Binding of FBD to "preformed clot"

To vials containing "preformed clots" (thawed at room temperature), add 300 µl 150 mM$NaCl_2$ 20 mM $NaHCO_3$, pH 8.0, containing: 1×Tyrode's buffer; 0.6% BSA; 5 mM $CaCl_2$and 0.15 µM $^{125}$I-FBD. The binding reaction is carried out (in the absence or presence of 0.03% sodium iodoacetate may be added to this mixture to inhibit the activity of the endogenous transglutaminase, Factor XIIIa) at 37° C. for 18 hours. The clot is then transferred to a siliconized vial, washed 3 times with 1 ml "wash buffer" 20 mM $NaHCO_3$, 1% BSA, 1 mM PMSF, 2 mM EDTA), and counted in a gamma counter.

The results comparing plasmatic and recombinant 31 kD with recombinant 18.5 kD, 12 kD, 45 kD (12 kD FBD fused to 33 kD CBD produced as shown in FIG. 12), and 33 kD CBD are shown in FIG. 30. All the FBD polypeptide fragments bound to a similar degree while the CBD polypeptide bound only to a very small degree. The 50–75% inhibition caused by the addition of the transglutaminase (Factor XIII) inhibitor iodoacetate shows that transglutaminase is active in the binding reaction. Its lack of effect on 33 kD CBD binding to clot indicates that CBD binding to clot is mediated by a different, possibly non-specific mechanism. As previously shown in coassigned PCT Publication No. WO 90/07577 (page 138, lines 1–24), the FBD is covalently bound to the fibrin clot. The participation of transglutaminase as shown and the biochemical characterization of $^{125}$I-FBD-fibrin complex indicate that at least 70% of the FBD polypeptide covalently bound to the fibrin.

II. Binding to Vascular Components

In addition to specific binding to fibrin, FBD polypeptides also show a certain degree of non-specific binding to other vascular components with which they come in contact. Examples of vascular components are endothelial cells (EC), extra cellular matrix (ECM), and even fibronectin itself (FN). This non-specific binding is one of the factors that determine the background level when performing diagnostic imaging procedures. The lower the non-specific binding, the more effective the imaging and the less the total radioactive reagent it is necessary to administer to the patient. Therefore experiments were performed to compare non-specific binding to vascular components of the 12 kD FBD fragment and 31 kD FBD polypeptide.

1 ml aliquots of 0.3 μM $^{125}$I-12 kD or $^{125}$I-31 kD (5×10$^5$ cpm/μg and 7.5×10$^5$cpm/μg in PBS containing 0.1% BSA, respectively), were added in duplicate to 35 mm petri dishes (Falcon) containing: confluent endothelial cells ("EC"), Extracellular matrix ("ECM"), (Eldor et al., Blood 65: 1477 (1985)) or immobilized human fibronectin ("FN"), (1 ml per plate of PBS containing 50μg/ ml FN, incubated at 4° C. overnight and then incubated for two hours at room temperature with 1 ml of PBS containing 1% BSA for blocking). When indicated "+TG", plates also contained transglutaminase at 0.02 U/ml (Sigma). Experimental plates were incubated for 60 minutes at 37° C. in a $CO_2$ incubator, washed 3 times with i ml "washing solution" (PBS containing 2 mM PMSF and 2 mM (EDTA). Bound radioactivity was then extracted by incubation for 60 min. with "Extraction solution" (washing solution containing 1% deoxycholate, 2 mM PMSF, 2 mM EDTA, 2 mM NME, and 2 mM iodoacetic acid). The solution is then transferred to tubes and the radioactivity measured in a gamma counter.

The results summarized in FIG. 28 show that the 12 kD FBD polypeptide binds only weakly to the vascular components endothelial cells, extracellular matrix, and fibronectin by comparison to the binding of the 31 kD FBD polypeptide.

III. Bacterial Binding

The involvement of fibronectin in adhesion to, and invasion of, wounds by a wide range of gram-positive bacteria is well established (18). The fibrin binding domain of authentic plasma derived FN has been shown to interact with high affinity to specific receptors on the surface of bacteria. The sites at which Staphylococcus aureus typically initiates infection are rich in FN, e.g. blood clots and subendothelium. Furthermore, exogenous FN enhances bacterial adhesion to these sites. FN binds to *S. aureus* through saturable, specific surface protein receptors. Scatchard analysis has revealed high affinity receptors with binding constant of 5×10$^9$ M, and a range of 100–20,000 receptors per bacterium (19). The expression of FN receptors correlates with invasivehess and pathogenicity of the clinical isolates. Removal of the FN receptors from *S. aureus* by mechanical means, orby growth of the bacteria in the presence of antibiotics decreases their ability to adhere to FN. As FN is a divalent molecule consisting of multiple functional domains with cell binding and collagen binding activities in addition to bacterial binding, it can anchor the bacteria to the wound via the various components of the extracellular matrix as well as via the FN receptor in tissue cells.

Another approach to understanding the interaction between FN and *S. aureus* is through the inhibition of the binding of *S. aureus* to endothelial cells by the FBD polypeptide fragments.

Binding of the 31 kD FBD polypeptide to *S. aureus* has previously been disclosed (coassigned PCT Publication No. WO/90/07577, pages 146–153). Similar experiments describe below showed that in contrast to the 31 kD FBD polypeptide, the 12 kD and 18.5 kD FBD polypeptide fragments do not bind *S. aureus*, and do not inhibit *S. aureus* in binding experiments. However, the 20 kD polypeptide does inhibit the binding of *S. aureus* (see FIG. 8); this may be due to the additional (non-authentic) C-terminal amino acids (see Example 2) which may affect its activity directly or indirectly through some specific refolding.

The following sections are presented in order to compare the 31 kD FBD polypeptide to other FBD polypeptide fragments both in terms of direct binding to *S. aureus*, and in terms of inhibition of binding of *S. aureus* to endothelial cells.

Materials and Methoda

A. Binding of labeled FN or FBD to bacteria

1. Direct binding in solution

Various concentrations of $^{125}$I-r31 kD FBD or $^{125}$I-FN, were added to 5×10$^8$ *S. aureus* bacteria in a PBS solution additionally containing 0.1% Tween and 1% BSA. The final volume was 1 ml. Total radioactivity in the reaction was assayed using a 20 μl aliquot taken immediately after the addition of the bacteria.

The mixture was incubated for 2 hours at 20° C. while rocking.

The amount of binding was assayedbyremoving 100 μl of the incubation mixture and layering on top of 0.5 ml PBS layered on 3 ml 10% Percoil-0.15M NaCl in a 5 ml siliconized tube. This was then centrifuged at 1,350×g (4,000 rpm in a SW bucket rotor) for 15 minutes at 20° C. The supernatant was aspirated and the pellet assayed for radioactivity.

2. Competition with unlabeled FN, FBD and related molecules

The procedure followed was identical to the above procedure except that 3 μg/ml $^{125}$I-p31 kD was used and the specified amount of the competing molecule (FN or FBD) was also added to the initial binding mixture.

3. Binding of radioactively labeled bacteria to immobilized FN

Plastic vials were coated with 0.3 ml of 50 μg/ml FN, or 1% BSA.

The tubes were incubated with shaking at 4° C. overnight. The tubes were then washed with 5 ml PBS three times. Then 0.3 ml of 1% BSA in PBS was added and the tubes were further incubated with shaking for 2–3 hours at 20° C. (for blocking free sites).

In indirect-binding experiments, the bacteria were preincubated with inhibitor, at 4° C. for 2 hours.

The bacteria (4×10$^6$ pfu/ml, 3 pfu/cpm) were added to the vials at concentrations indicated in the figure legends. The final volume of the assay mix was 0.3 ml PBS. The mix was slowly agitated at 4° C. for 90–120 minutes.

The tubes were then decanted and washed with 5 ml PBS three times.

5 ml of scintillation-liquid was added when assaying for binding of 3H-labeled bacteria.

B. Inhibition of Binding of *S. aureus* to Endothelial Cells by FBD Fragments

I. Iodination of *S. aureus*

*S. aureus* SA113 (ATCC Accession No. 35556) were grown in Tryptic Soy Broth (Difco Laboratories, U.S.A.) at 37° using a 1l fermentor culture. Bacteria were harvested in the middle of the logarithmic phase when optical density reached 2.30 OD (at 660 nm).The bacterial pellet was resuspended in 500 ml of PBS containing 5 mM PMSF and washed 3 times. The cells were then suspended in 100 ml PBS with 1 mM PMSF and 5mM NEM (N-Ethyl maleimide, Sigma E-3876), heat-inactivated at 88° C. for 20 min. for fixation, cooled in ice-water and then stored in small aliquots at −20° C. Before use, the bacterial concentration was brought to 5×10$^9$ PFU/ml. A 100 μCi aliquot of Bolton-Hunter reagent for protein iodination (Amersham) was evaporated in a glass tube on ice. Bacterial suspension (1 ml) was added to the evaporated reagent and mixed gently for 10' on ice. The reaction was stopped by adding 1 ml of 0.2M glycine in 50 mM potassium phosphate buffer pH 8.5. The reaction mixture was then suspended in 20 ml PBS containing 1 mM PMSF. After centrifugation at 3000 rpm for 10' at 5° C., the wash step was repeated twice. The final pellet was suspended in 2.2 ml PBS containing 1 µM PMSF and stored at −20° C. The specific activity was generally 20–100 PFU/cpm.

II. Growth of Endothelial Cells

Bovine Aortic Endothelial cells $A_5P_7$ (obtained from A. Eldor, Hadassa Hospital, Jerusalem), were maintained in tissue culture as previously described (Ogawa S. K. et al 1985 Infect. Immunol. 50: 218–224). The culture media contained DMEM/+1% D-Glucose and 10% FCS (both from Biological Industries, Kibbutz Beth-Haemek, Israel) supplemented with L-glutamine and gentamycin (7 mM and 5mg/ml, respectively, both from Sigma Chemicals).

The cells were maintained at 37° C. and 5.5% $CO_2$ in 150 ml tissue culture flasks (Falcon).

Confluent monolayers for binding experiments were prepared in either 24 well tissue culture plates or 35 mm tissue culture plates (Corning Glassware, Corning N.Y.). Wells and plates were preincubated for 30 min. with 0.5 ml or 1 ml complete medium, respectively, prior to the addition of cell suspension. In a typical experiment, wells and plates were seeded with $5 \times 10^4$ and $10^5$ cells, respectively, and used after 3–4 days when culture became confluent.

III. Bindina of $^{125}$I-S. aureus to Endothelial Cells

This procedure is essentially as described in the above mentioned reference (Ogawa et al. 1985). An aliquot of labeled S. aureus prepared as described above was diluted in PBS to $10^8$/ml. 3.5 µl of labeled bacteria were added to a mix containing 200uL DMEM +10% FCS, 33uL 150 mM NaCl containing 20 mMNaHCO₃, 17 µl of PBS or the competitor to be tested, and then incubated for 2 hours with gentle mixing. The bacteria were then added to confluent monolayers of endothelial cells pregrown as described above. The endothelial cells were washed with saline immediately prior to performing the assay. The mixture was incubated at 4° C. for 1 hour with gentle shaking or 2 hours at 37° C. in 5% $CO_2$ without shaking. The unbound labeled bacteria were removed by washing 3 times with cold PBS containing 2 mMPMSF and 2 mM EDTA. The bound labeled bacteria were then extracted by shaking at room temperature for one hour in PBS containing 1% deoxycholate, 20 mM Tris HCl pH 8.3, 2 mM PMSF, 2 mM EDTA, 2 mM NEM, and 2 mM iodoacetic acid. The extraction was repeated once, and the combined extract was counted in a gamma counter.

Results

A. Binding of bacteria to $^{125}$I-FN or FBD in solution

1. Direct Binding

Experiments were performed in order to determine the binding of $^{125}$I-FN or $^{125}$I-rFBD to S. aureus bacteria in suspension. Various amounts of radioactive FN or r31 kD were added to $5 \times 10^8$ bacteria incubated for 2 hours and then centrifuged over a 10% Percoil-saline solution. Radioactivity was monitored in the pellet.

The results showed increased binding of $^{125}$I-rFBD (r31 kD) to the bacteria in suspension as compared to the binding of the $^{125}$I-FN.

This increased binding of $^{125}$I-rFBD to S. aureus as compared to $^{125}$I-FN binding to S. aureus can be attributed to a higher affinity of a monovalent domain in comparison to bivalent multidomain of intact plasma derived FN.

Similar experiments performed with the 12 kD and 18.5 kD FBD fragments showed no binding whatsoever.

2. Competition with "native" unlabeled FN, FBD and Related Molecules

A fixed amount of $^{125}$I-p31 kD (3 µg/ml) was incubated with $5 \times 10^8$ bacteria in the presence of increasing amounts of various FBD molecules as competitors.

The results demonstrate that "native" FN, as well as properly folded p31 kD or r31 kD FBD inhibited the binding of $^{125}$I-p31 kD to S. aureus in a similar fashion, indicating that recombinant 31 kD is as active as the natural plasma-derived molecules. However, the reduced ("scrambled") forms of recombinant or plasma derived FBD only minimally inhibit the binding of $^{125}$I-FBD to the bacteria, indicating that proper folding is necessary for binding. Furthermore, r18.5 kD and r12 kD FBD polypeptides as well as a CBD polypeptide (33 kD cell binding domain of FN) did not compete with binding of $^{125}$I-pFBD to S. aureus, showing conclusively that only the complete 31 kD FBD domain has bacterial binding activity while the shorter FBD fragments do not bind bacteria.

B. Binding of labeled S. aureus to immobilized FN

To estimate the capacity of rFBD (r31 kD) to interfere with the adherence of bacteria to the extracellular matrix in wounds, a competition assay was developed. In this assay, adherence of S. aureus to plastic surface coated with FN, and the interference of FBD with the binding was measured. The results demonstrate that the adhesion of 8, aureus to FN coated plastic vials was inhibited following pre-incubation of S. aureus with FN, pFBD (31 kD) or rFBD (31 kD). The extent of inhibition bythese molecules was similar. A nonrelated protein, BSA, which does not have S. aureus binding sites, did not cause any inhibition in adhesion of radioactive labeled S. aureus to FN coated plastic vials.

In similar experiments performed with the 12 kD FBD fragments, no inhibition of binding of S. aureus to immobilized FN was detected.

C. Inhibition of Binding of S. aureus to Endothelial Cells

FIG. 29 shows the inhibition by FBD fragments of binding of S. aureus to endothelial cells as described above. The 31 kD shows a dramatic and dose dependent effect on S. aureus binding to endothelial cells. However, neither the 18.5 kD nor the 12 kD have any inhibitory effect, showing that the binding site on the FBD for the S. aureus receptor is not found on the 12 kD and 18.5 kD fragments. This is a surprising result since this is the first demonstration that the FBD of fibronectin can be separated from the S. aureus binding domain.

Summary and Conclusion

Table C summarizes and compares the activities of various FBD polypeptide fragments as described above.

TABLE C

Comparison of Activities and Binding Specificity of Various FBD Polypeptide Fragments

| Activity | 31 kD | 18.5 kD | 12 kD |
| --- | --- | --- | --- |
| Fibrin Binding | High | High | High |
| Binding to Vascular Components | High | Low | Low |
| Bacterial Binding | Yes | No | No |
| Inhibition of Binding S. aureus to Endothelial Cells | Yes | No | No |

It is thus seen that the 18.5 kD and 12 kD FBD polypeptide fragments have a high covalent binding specificity for fibrin, together with a narrower spectrum of activities and lower specificity for other ligands such as vascular components and bacteria than the 31 kD. This is an advantageous characteristic for a thrombus imaging agent, ensuring that as a diagnostic reagent it has a high affinity for fibrin-containing thrombi, while maintaining low background levels. An in vivo example of this is provided in Example 13.

Example 10

An Improved Method of Refolding/Oxidation and Purification of Shorter FBD polypeptides Fragments The recombinant FBD proteins—r31 kD ("5 fingers"), 18.5 kD (a more authentic version of the "3 fingers" than the previously described 20 kD) and r12 kD ("2 fingers")—are expressed in *E. coli* and refolded/reoxidized, before being purified to homogeneity (>98% purity). The refolding/reoxidation processes used for the full 31 kD FBD polypeptide (5-fingered) and for the shorter 12 kD and 18.5 kD FBD polypeptide fragments (2- and 3-fingered) are different and have been described above in Examples 2 and 5. The method of Example 5 has been found to be applicable to all 2- and 3-fingered FBD proteins, that have so far been refolded, but not to the 5-fingered protein, the 31 kD, even when the reduction (followed by reoxidation) is performed on purified plasma-derived 31 kD, i.e., "opening" and refolding the protein. This procedure has recently been improved without affecting the principle of the refolding process, and the improved procedure has been found applicable to the 12 kD, 18.5 kD, and 20 kD polypeptides, and to the 45 kD FBD-CBD hybrid polypeptide (12 kD-33 kD) but not to the 31 kD polypeptide.

The process is essentially as described in Example 5. The following description relates to the 12 kD polypeptide and similar results were obtained for the 18.5 kD FBD polypeptide and 45 kD FBD-CBD hybrid polypeptides; these polypeptides were expressed. by plasmids pFN 203-2 (FIG. 27), pFN 208-13 (FIG. 23) and plasmid pFN 202-5 (FIG. 12), respectively.

The bacterial cake was produced as described in Example 2 by fermentation of *E. coli* strain A4255 harboring plasmid pFN 203-2 (as described in FIG. 27).

A. Crude processing of the bacterial cake: The washing and extraction of the pellet was performed in a similar manner to that of the two- and three-fingered FBD proteins (see Example 5). The bacterial cake was suspended in 20 volumes of 50 mM Tris HCl, 50 mM EDTA, pH 7.4. After 15 minutes of stirring, the suspension was disrupted by twice passing it through a Dynomill kD 5 bead mill at 50 liters/hour. The disrupted suspension was centrifuged (14000×g in a Cepa 101 centrifuge at a feed rate of 80 liter per hour. The pellet was suspended in the above buffer to a final volume 10 times that of the original bacterial cake's dry cell weight. The suspension was brought to 37° C. and lysozyme added (2500 U/ml). After 2 hours of stirring at 37° C., Triton X-100 (1%) was added and incubation with stirring continued for 30 min at room temperature. The suspension was then diluted with an equal volume of deionized water, sonicated by a W 370 sonicator and centrifuged at 14000×g under the same conditions as above. The pellet was washed twice by resuspending in deionized water to a final volume 16 times that of the dry cell weight of the bacterial cake, and stirring for 15 min at room temperature at pH 7.4. After stirring the suspension was sonicated with a W 370 sonicator and centrifuged at 14000×g under the same conditions as above. The washed and extracted pellet containing inclusion bodies of the FBD polypeptide is kept frozen at −20° C. until further processing.

B. Refolding/reoxidation: The resulting washed inclusion bodies (100 g - representing 19.2 g of dry weight) were solubilized in 5 volumes of 10 mM Tris HCl pH 8.0, 5 mM EDTA, 1 mM phenylmethanesulfonyl fluoride (PMSF), 10 mM ε-aminocaproic acid, containing additionally 6M guanidine HCl (final volume 600 ml). The sample was reduced by the addition of 2.27 ml of β-mercaptoethanol (final concentration: 50 mM) and stirred at room temperature in the absence of air, i.e., in a sealed container, for 90 minutes. The reduced protein was reoxidized (at a protein concentration of 0.81 mg/ml) in 0.54M guanidine HCl, as follows: 6 liters of the Oxidation Buffer (10 mM Tris HCl pH 8.0, 5 mM EDTA, 1 mM PMSF 10 mM ε-aminocaproic acid, containing additionally 0.3 mMoxidized glutathione (GSSG), were added to the solution of the reduced protein while stirring at a rate of 150 ml per min. The oxidation process was continued for 65 hours at room temperature in a closed container, while being constantly and gently stirred. The solution of the reoxidized protein was filtered through Whatman No. 3 filter paper to remove the precipitates and then concentrated 10-fold on a Pellicon tangential flow ultrafiltration unit equipped with a 3 kD MW cut off membrane and diafiltered on the same membrane, in order to remove the guanidine HCl, the β-mercaptoethanol and the GSSG. A further precipitate, which developed upon standing at 4° C. overnight, was removedby centrifugation at 22,500×g for 45 minutes. (For the 18.5 kD and 45 kD polypeptides, ultrafiltration and diafiltration were performed with a 10 kD molecular weight cutoff membrane.)

C. Purification: The concentrated and clarified solution (700 ml) was loaded on a Q-Sepharose column (2.5×28.5 cm), equilibrated in 10 mM Tris HCl, 5 mM EDTA, 1 mM PMSF 10 mM ε-aminocaproic acid, pH8.0. The flow-through of the column, containing the 45 kD protein, was applied—in portions of 170–350 mg) onto a Heparin-Sepharose column (2×6.5 cm), equilibrated in 10 mM Tris HCl, pH 8.0, 5 mM EDTA. After washing the unbound protein with this buffer, the bound protein was eluted with the same buffer, containing additionally 500 mM NaCl. The eluates were pooled and kept frozen at −20° C.

As stated above, this procedure was applied with minor modifications to both the 18.5 kD polypeptide and the 45 kD FBD-CBD hybrid polypeptide. The results for both these polypeptides were very similar to those obtained for the 12 kD polypeptide.

Use of buffer containing at least 0.5M NaCl for elution from Heparin-Sepharose and storage was found to be necessary to ensure stability of the polypeptides, which otherwise tended to rapidly lose their activity; this applies particularly to the 31 kD polypeptide.

Example 11

Characterization of FBD Polypeptide Fraqments

I. Procedures

The FBD polypeptide fragments produced by the methods of this application were evaluated and compared in a series of characterization tests by the following methods known in the art.

1. SDS-PAGE +ME (ME=β-mercaptoethanol): 12.5 % acrylamide slab gels are loaded with protein, which had previously been treated by boiling 5 minutes in sample buffer containing 1% SDS—under reducing conditions (+1% ME). Electrophoresis was performed with 20 µg per lane and the gels stained with Coomassie Brilliant Blue. The parameters measured are: a) the mobility, which, when compared with molecular weight markers (94, 67, 43, 30, 20.1 and 14.4 kD) can be expressed in terms of an apparent molecular weight for the protein studied; b) the homogeneity or purity, which can be assessed from the relative intensities of the major and minor bands.

2. SDS-PAGE –ME: 12.5 % acrylamide slab gels are loaded with protein, which had previously been treated—5 min boiling in sample buffer containing 1% SDS—under non-reducing conditions (—ME). Electrophoresis is performed with 20 µg per lane and the gels stained with Coomassie Brilliant Blue. The parameters measured are: a) the mobility, which, when compared with molecular weight markers (94, 67, 43, 30, 20.1 and 14.4 kD) can be expressed in terms of an apparent molecular weight for the protein studied; b) the homogeneity or purity, which can be assessed from the relative intensities of the major and minor bands—in particular, under these conditions, one can evaluate the amounts of disulfide-linked dimers.

3. Gel filtration on Supsrose 12: The apparent molecular weight and the homogeneity of the protein preparations were evaluated from slution profiles obtained on a Superose 12 column (HR10/30, Pharmacia Fine Chemicals), attached to either an FPLC apparatus, equipped with a liquid chromatography controller LCC-500 and recorder (Pharmacia Fine Chemicals) or to an HPLC system (Waters Associates), consisting of 2 pumps (Model 501), an injector (Model U6K) and an automated gradient controller (Model 580) equipped with a variable wavelength detector—Spectro-Monitor 3000 (LDC/Milton Roy)—and a Chromato-Integrator (Merck-Hitachi, Model 2000). The column was calibratedby the following molecular weight standards, whose retention times were determined: bovine serum albumin (67 kD), ovalbumin (43 kD), chymotrypsinogen (25 kD) and ribonuclease (13.7 kD). The flow rate was 0.8 ml/min, using the standard running buffer,i.e., 150 mM NaCl—20 mM Tris. HCl, pH 7.8–8.0. Two parameters were monitored: the retention time and the half-height bandwidth.

4. UV spectroscopy: Spectra were obtained at room temperature in BBS or PBS at concentrations of 0.2–1 mg/ml on a Philips UV/Vis scanning spectrophotometer Model PU8720 (bandwidth 2 nm) equipped with a printer/plotter. The spectra were measured in Pye Unicam UV silica cells of 10 mm path-length. Both the absorption coefficient, i.e., $\epsilon_{1\%}$ at the spectrum's $\lambda_{max}$, and the ratio between the absorbances at $\lambda_{max}$ and $\lambda_{min}$ were monitored.

5. Intrinsic fluorescence: Data were obtained on a Jasco spectrofluorometer, Model FP-770 at 25° C.±0.1° C. Excitation wavelength was 280 nm and both excitation and emission slits were set at 5 nm. The concentration of proteins in the assay was 8–25 µg/ml in either PBS or fresh BBS, pH 7.5. There is a marked pH dependence of both measured parameters, i.e., $\lambda_{max}$ (the wavelength of the spectrum's maximum) and the specific intensity (the fluorescence intensity at the spectrum's maximum normalized by the protein concentration in mg/ml).

6. Amino acid composition: This test is performed according to the Stein & Moore proven methodology for amino acid analysis. Protein hydrolysis is performed on dried protein following treatment in a Speed Vac centrifuge (Savant): 6.0N HCl is added, i ml per each mg of protein; nitrogen is substituted for air by successive evacuations and rinsingby nitrogen. The tube is sealed and heated for 22 h at 110°±0.1° C. The currently used method is essentially in compliance with the USP Drafts of Biotechnology-Derived Products, 1989 USP Convention, Inc.. <954>pp 96–98. The analyzer in use is a Biotronic LC 5000, serial number 515-01. The parameter evaluatedby this method is the number of residues of each amino acid, except for Cys and Trp.

7. Heparin-Sepharose chromatography: Samples of up to 200 µl were injected onto an analytical Heparin-Sepharose column (5.5×0.5 cm), attached to an HPLC system (Waters Associates), consisting of 2 pumps (Model 501), an injector (Model U6K) and an automated gradient controller (Model 580) equipped with a variable wavelength detector—Spectro-Monitor 3000 (LDC/Milton Roy)—and a Chromato-Integrator (Merck-Hitachi, Model 2000). The column was preequilibrated in 10 mM Na-phosphate pH 6.5, 75 mM NaCl at a flow rate of 0.5 ml/min and washed for 5 minutes in the same buffer. The proteins were eluted in a linear gradient from 75 to 500 mM NaCl in buffer in 37.5 minutes. Two parameters were evaluated, the retention time (ret. time), which is proportional to the salt concentration at which the protein elutes and the half-height band width (half-ht. b.w.), which assesses the peak's homogeneity.

8. Reverse phase-HPLC chromatography: Samples were injected onto an analytical Waters C18 Bondapak reverse phase column (30×0.39 cm), attached to an HPLC system as in Section 1.7. The column was preequilibrated in 80% $H_2O$, 0.1% TFA/20% acetonitrile, 0.08% TFA at a flow rate of 1 ml/min and washed for 5 min with the same solvents. The proteins were eluted in a linear gradient to 40% $H_2O$—0.1% TFA: 60% acetonitrile—0.08% TFA in 40 minutes. Two parameters were evaluated, the retention time (ret. time) and the half-height band width (half-ht. b.w.), which assesses the peak's homogeneity.

9. Tryptic maps: 200 µg samples of the various batches were digested for 10 min at 37° at various trypsin w/w ratios, in %: 0.25, 0.5, 1.0, 2.5, 5.0 & 10.0. The reaction was stopped with 5 mM PMSF, and following 30 min on ice, was treated with sample buffers ±ME (see Sections 1.1.& 1.2.) and run on 20 % acrylamide slab gels—as above. The degree of equivalence between the band patterns was assessed after staining with Coomassie Brilliant Blue.

10. Ellman's method for thiol determination in proteins: The determination is performed on denatured proteins, in order to enable full exposure of thiolgroups.

Stock solutions: 1. Guanidine-HCl (of purest quality available) 7.2 M in 10 mM Tris-HCl, pH 8 (GuCl); 2. DTNB (Ellman's reagent) 5×10 −3M in 100 mM K—phosphate buffer, pH 7.

Method: A protein sample containing 10–100 µM of thiol groups is made up to 0.15 ml; a DTNB blank, (i.e. without protein included); 0.75 ml of GuCl 7.2 M is added to give a final concentration of 6M. After incubation for 15–30 minutes at room temperature, the blank of the protein solutions is read at 412 nm. 100 µl DTNB is then added to a final concentration of $5 \times 10^{-4}$M. After incubation for 30 minutes at room temperature, the samples are read at 412 nm versus the DTNB blank. The concentration is calculated using $\epsilon = 13{,}600$ $M^{-cm-1}$, i.e., 100 µM of thiol groups give an absorbance value of 1.36.

11. Precipitation/Adsorption

Eppendorf tubes containing frozen $^{125}$I-FBD are allowed to thaw at room temperature, and then mixed byvortexing. Two 5 µl aliquots are removed for radioactivity monitoring. When high specific activity $^{125}$I-FBD is used, dilution in siliconized tubes with high salt buffer (0.6 M NaCl- 20 mM, $NaHCO_3$ pH 8–9) should be carried out before counting. The stock solution is then centrifuged at top speed in an Eppendorf centrifuge and the supernatant removed to another siliconized tube. Two5 µl aliquots are counted again. The differences between the radioactivity obtained before and after centrifugation represent the "percent precipitation".

When $^{125}$I-FBD is kept frozen (at −70° C.) in siliconized tubes and in the high salt (0.6 M NaCl) buffer the protein is quite stable. We found only minimal precipitation of $^{125}$I-FBD of 0–7% within a period of 2 weeks. However, when kept in non-siliconized tubes and in a low salt (150 mM NaCl) buffer, $^{125}$I-FBD precipitation couldbe as high as to 60–80% in 2–3 days. Under these conditions both precipitation and adsorption to the tube are substantial.

12. Reaction of FBD with $^{14}$C-putrescine

The reaction measures the accessibility of Gln #3 of the FBD to the transglutaminase reaction of Factor XIIIa).

Method: The reaction mixtures (100 µl) in siliconized Eppendorf tubes contain: 10 mM CaCl$_2$, 50 mM Tris-HCl (pH 7.5), 5 mM DTT, 120 µM $^{14}$C-putrescine (Sigma), 6 µM FBD and 0.05U/ml guinea pig liver transglutaminase (Sigma). After incubation at room temperature for 0,15,30 and 60 min, aliquots (10 µl) are added to tubes containing 200 µl stop reagent (0.4 mg/ml BSA, 50 mM EDTA, 150 mM NaCl, 20 mM NaHCO$_3$, pH 8.0) at 0° C (on ice). Cold 20% TCA (250 µl) is added and following 10 min incubation on ice, an additional 3 ml of cold 20% TCA is added and the tube content is filtered on a glass fiber filter (Whatman GFC). The filters are washed 3 times with cold 20% TCA and once with 70% ethanol. TCA precipitable radioactive material was monitored in a beta counter. The accessibility of Gln #3 in the FBD to transglutamination was calculated based on the specific activity of $^{14}$C- putrescine and on the concentration of FBD in the reaction mixture; incorporation of 5% of the total counts is equivalent to 100% accessibility.

13. Self Association

The reaction is carried out in 300 µl of a 150mM NaCl-20 mM NaHCO$_3$, pH 8.0, containing also: 0.1×Tyrode's buffer; 0.6% BSA; 5 mM CaCl$_2$; 0.15 µM $^{125}$I-FBD; 6 µl Transglutaminase (0.02U/ml)—see Section 12.

Reaction mixtures were incubated at 37° C. for 18 hours, followed by vacuum aspiration of the reaction solution, washing 3 times with 1 ml "wash buffer" and measuring the radioactivity in a gamma counter.

II. Results

All the FBD proteins contain an extra methionine at the amino terminus, and instead of the pyroglutamate residue, which is the blocked N-terminus of the p31 kD (obtained by post-translational modification from the coded Gln), their N-terminal Met is followed by a Gln residue. The positive identification of FBD proteins was also confirmed byWestern blot analysis of the gels—developed with anti-20 kD. The 45 kD was identified by developing its blots with both anti-20 kD and anti-33 kD of the cell binding domain.

The FBD fragments and the 45 kD FBD-CBDhybrid were further characterized bya.variety of: a) physico-chemical tests as described above in comparison to the 31 kD (see Tables C and D).

b) biochemical and biological tests an vitro: accessibility of Gln #3 to transglutaminase-catalyzed transamidation (see Tables C and D); and self association. Binding to preformed fibrin clots is described in Example 9.

c) biological tests in vivo: binding to venous thrombi in rats is described in Example 13.

Table D details the parameters assayed in the chemical and physico-chemical characterization of FBD polypeptides and of the FBD-CBD hybrid. The 12 kD, 18.5 kD and 45 kD polypeptides were produced by plasmids pFN 203-2, pFN 208-13, and pFN 202-5, respectively.

Table E provides actual measured values for the FBD polypeptides assayed.

TABLE D

Characterization Parameters for the FBD proteins

| METHOD | PARAMETERS |
| --- | --- |
| 1. SDS-PAGE +ME | molecular weight (cf. markers.); purity & homogeneity |
| 2. SDS-PAGE –ME | molecular weight (cf. markers); purity & homogeneity |
| 3. Gel filt. (Superose 12) | retention time; half-height bandwidth |
| 4. UV spectroscopy | absorption coeffic. –$\lambda_{max}$–1%.; absorbance ratio $\lambda_{max}/\lambda_{min}$ |
| 5. Intrinsic fluorescence | specific intensity (I/prot. conc.); $\lambda_{max}$ |
| 6. Amino acid composition | residue number – equivalence to theoretical value |
| 7. Keparin-Sepharose | retention time; half-height bandwidth |
| 8. RP-HPLC | retention time; half-height bandwidth |
| 9. Ellman | Free thiols. |
| 10. Reaction with $^{14}$C-putrescine | Percent of theoretical binding – representing accessibility of Gln #3 to transglutaminase dependent transamidation (<0.5% binding in the absence of the enzyme). |

TABLE E

MEASURED VALUES FOR FBD PROTEINS

| PROTEIN | r18.5 kD | r12 kD | r45 kD | r31 kD |
| --- | --- | --- | --- | --- |
| 1. SDS-PAGE +ME | 18.5 kD; ≧98% | 14.2 kD; ≧98% | 42 kD; ≧90% | 31 kD; ≧98% |
| 2. SDS-PAGE –ME | 17.7 kD; ≧98% | 14.4 kD; ≧98% | 41 kD; ≧90% | 28 kD; ≧98% |
| 3. Gel filt. (Superose 12) | 18.29 min; 3 mm | 19.03 min; 2.5 mm | 16.56 min; 2 mm | 17.41 min; 3 mm |
| 4. UV spectroscopy | 19.2; 1.84 | 13.5; 2.02 | not done | 17.7; 1.55 |
| 5. Intrinsic fluorescence | 340 nm; 10.3 | 339 nm; 14.4 | not done | 343 nm; 18.1 |
| 6. Amino acid composition | Equivalent to theoretical value | Equivalent to theoretical value | not done | Equivalent to theoretical value |
| 7. Heparin-Sepharose | 32.77 min; 8 mm | 31.14 min; 8 mm | 34.00 min; 8.5 mm | 36.50 min; 9 mm |
| 8. RP-HPLC | 23.02 min; 1 mm | 22.50 min; 1 mm | not done | 23.76 min; 2 mm |

TABLE E-continued

MEASURED VALUES FOR FBD PROTEINS

| PROTEIN | r18.5 kD | r12 kD | r45 kD | r31 kD |
|---|---|---|---|---|
| 9. Ellman | ≦0.2% | ≦0.2% | not done | ≦1% |
| 10. Reaction with 14C-putrescine | 86.0% | 100.0* | not done | 91% |

Example 12

Directed thrombolysis ultilizing FBD-SK complexes

I. Introduction

Simple and efficient fibrin-directed thrombolytic agents are a major goal of the pharmaceutical industry. Our approach for the development of such a drug is based on the observation that the N-terminal fibrin binding domain of fibronectin (FBD) can be specifically cross-linked to fibrin clots by Factor XIIIa. Since newly formed thrombi are the only environment which is enriched in activated Factor XIII, FBD may display preferential binding to new over old thrombi and become an ultimate targeting vehicle. We therefore generated, by chemical cross-linking, chimeric FBD-Streptokinase conjugates and analyzed their activity in clot dissolution.

Tissue plasminogen activator (TPA) and Streptokinase (SK) are known as the best fibrinolytic agents used in cardiovascular therapy. TPA and SK both degrade fibrin, but they differ in their mode of action. TPA exhibits fibrin—selective plasminogen activation. The selectivity of TPA is due to the presence of fibrin binding sites at the amino terminal region of the molecule. TPA binds to fibrin with a $K_d$ of 0.16 µM. When bound to fibrin, its $K_m$ for the process of plasminogen activation decreases from 83 µM to 0.18 µM resulting in an efficient enzymatic conversion of plasminogen to plasmin.

SK interacts with plasminogen to forman activation complex capable of catalyzing the formation of plasmin. This interaction is not dependent on fibrin binding. The activated SK-plasminogen complex in the blood stream may catalyze a systemic conversion of circulating plasminogen to plasmin. The activated plasmin is preferentially inhibited by $\alpha_2$-antiplasmin. Once the inhibitor capacity is exhausted, free fibrinogen, fibrin and some other plasma proteins are degraded by plasmin. The resulting fibrinogenolysis causes disruption of the normal coagulation mechanisms, increasing thereby the risk of hemorrhage.

Due to the affinity of TPA to fibrin it is assumed to be advantageous as a fibrinolytic agent relative to SK which does not bind fibrin. TPA and SK were recently compared for their therapeutic efficiency in several large scale human clinical trials. According to the accumulated data SK is the agent of choice for most patients (Scrip No. 1597, pages 22–23, Mar. 8, 1991). A major interest still exists in developing an improved fibrinolytic agent with increased fibrin selectivity. Both chemical cross-linking and recombinant DNA methods are used to design the desired molecules. Several chimeric plasminogen activator molecules have been constructed containing various high affinity fibrin binding domains of several plasma-derived proteins or anti-fibrin monoclonal antibodies bound to the catalytic domain of TPA. These molecules are being analyzed by several pharmaceutical companies for their therapeutic efficacy.

Activated factor XIII (transglutaminase) catalyzes the cross-linking of fibrin molecules in the final step of blood coagulation, thereby increasing the mechanical stability of the clot. As described in Example 6B, intact plasmatic fibronectin (FN) is also cross linked to fibrin by factor XIIIa.

As described in Examples 2 and 4, applicants have cloned and expressed FBD polypeptide fragments of the FN (12 kD, 18.5 kD, 20 kD and 31 kD). These polypeptides have been studied in vitro and in vivO for their ability to become covalently bound to fibrin clots and thrombi in the presence of factor XIIIa (Example 6, 9, 13). We decided to take advantage of this intrinsic ability of the FBD molecules with respect to their covalent binding to fibrin and to generate by chemical cross-linking (or by recombinant DNA methods) chimeric FBD-SK molecules in order to target SK to the thrombi, thereby reducing the risk of hemorrhage.

II. Chemical derivatization and Cross-linking of FBD and SK

FBD polypeptides and fragments spanning the amino terminal region of FN were derivatized with N-succinimidyl-3- (2-pyridyldithio) propionate (SPDP)—a heterobifunctional cross-linker.

SPDP reacts at alkaline pH with primary amines introducing 2-pyridyl- disulfide groups into the protein. By measuring the absorbance at 343 nm, which in this pH range is specific for the thio-pyridine group released after the reduction of the modified FBD, the number of cross-linker groups per FBD molecule was calculated. With the plasmatic 31 kD FBD molecule very poor reaction yields were obtained as it tended to precipitate under the conditions of the chemical modification. Further experiments were performed with the recombinant 12 kD FBD molecule produced byplasmid pFN 196-2 (FIG. 10). Approximately 2 residues of cross-linker were found to be introduced per each 12 kD FBD molecule.

SK, which lacks cysteine residues was derivatized with 2-iminothiolane. This reagent reacts with primary amines, introducing a charged spacer ending witha thiol group. The number of the thiolgroups introduced in the SK molecule was determined by the use of Ellman's reagent. Under the conditions of the modification it was found that about 2 thiol groups were introduced per SK molecule.

By mixing the two derivatized polypeptides the free thiol group will exchange with the 2-pyridyl-sulfide group, forming a disulfide bond between the two proteins and releasing pyridine-2-thiol. Conjugation was found to be optimal at 4 to 8 times molar excess of the derivatized FBD. Under these conditions essentially all derivatized SK molecules had reacted with FBD molecules. The conjugation process was analyzed by SDS-PAGE and by gel filtration on FPLC attached Superose 12. Complex formation was complete in about 10 minutes, yielding a mixture of molecules with variable FBD and SK content.

The chemical modification and cross linking reactions were performed according to Runge et al., PNAS, USA, 84: 7659–7662 (1987).

Under the optimized conditions established for the chemical modification reactions, the calculated number of pyridyldisulfide and thiol groups on each of the FBD and SK molecules is about 2. The conjugation mixture thus formed contained mostly the desired 1:1 hybrid.

Isolation of the FBD-SK complex

Separation between conjugated and free SK and FBD molecules was carried out in two steps as follows: First, gel filtration on Superose 6 was performed in order to remove excess 12 kD FBD. Second, chromatography on Heparin-Sepharose was used to separate free streptokinase from the conjugate which binds to the resin at 25 mM NaCl, 10 mMTris/HCl, pH 7.4, and was then eluted with 0.5M NaCl in the same buffer. Contamination by free SK, as. Judged by gel electrophoresis accounts for less than 5% of the final preparation.

Functional characterization of the FBD-SK complex

The cross-linked FBD-SK complex, purified by Heparin-Sepharose chromatography, was compared to native SK using the following criteria:

1. Kinetics of plasminogen activation using the chromogenic substrate S-2251 of plasmin (FIG. 33).
2. Fibrinolytic activity utilizing the fibrin-plate assay (FIG. 34), according to Neville Marsh, Fibrinolysis, 1981.
3. Human plasma clot lysis, using $^{125}$I-fibrinogen, for clot formation.

The results indicate that the complex retained a level of plasminogen activator activity comparable to that of SK. From FIG. 33 the apparent $K_m$ values for the plasminogen substrate, $K_{plg}$, were $3.1 \times 10^6$M and $1.8 \times 10^{-6}$M for the SK and the FBD-SK complex, respectively, whereas the catalytic rate constant for the complex, $k_{plg}$, was found to be lower by a factor of 2 than that for SK. Furthermore, FIG. 34 demonstrates no significant difference between the lysis zones formed after overnight incubationby either SK or the FBD-SK complex.

In addition, $^{14}$C-putrescine was incorporated into the complexes byguinea pig liver transglutaminase to about 40% of the level incorporated into the 12 kD FBD (FIG. 35); compare with Table E, Example 11. DTT increased incorporation into the complex up to 140%. No incorporation into SK was observed. These findings indicate that the FBD-SK conjugate has retained the potential of becoming cross-linked to thrombi by activated Factor XIII.

Applicants additionally envisage construction of a chimera FBD-SK polypeptide encoded by a recombinant plasmid.

Example 13

In vivo Labelling of Thrombi by $^{111}$In-labelled 12 kD and 18.5 kD-FBD in the Rat Stainless-steel Coil Model The model employed is essentially that described in Example 7. Recombinant 12 kD-, 18.5 kD- and 31 kD-FBD polypeptide fragments were labelled with $^{111}$In by the DTPA method (Example 8). The labelled materials (specific activity approx. $5 \times 10^6$ cpm/µg) were administered intravenously ($5 \times 10^6$ cpm/rat) into coil- bearing rats (Example 7) 5h after insertion of the coils. The coils bearing the thrombi were removed and counted 24 h after administration of the label. FIG. 31 presents the results of the specific radioactivity in the clots and blood, and FIG. 32 presents the respective thrombus to blood ratios. As shown, high thrombus specific radioactivity values were obtained with the three compounds. Higher values were found in the thrombi of the 31 kD FBD group, than in those of the 12 kD- and 18.5 kD-FBD fragments. However, the thrombus/blood ratios were higher for the 12 kD and 18.5 kD-FBD fragments, due to lower blood levels, as compared with the 31 kD-FBD. This maybe due to the narrow spectrum of specifities and activities of the shorter fragments by comparison with the 31 kD polypeptide (Example 9, Table C).

Example 14

Use of FBD polypeptides in Wound Healing

In early events of wound healing the epithelium migrates over a gel layer of fibrin and fibronectin, before the permanent basement membrane components, such as laminin and type IV collagen, are reformed. The initial plasma-derived gel, that contains both fibrin and fibronectin, is readily invaded by fibroblasts and serves hemostatic and adhesive functions, providing a provisional matrix for cell migration and a reservoir of chemotactic and growth factors ("wound hormones"). The fibrin extravascular gel, which rapidly forms a lattice, incorporates fibronectin. It has been shown that the fibroblasts in vivo attach to the fibrin lattice primarily via fibronectin (Grinnell, F. et al. (1980) Cell 19 517–525; Colvin, R. B. et. al., (1979) Lab Invest. 41 464–473; Knox, P. et. al. (1986), J. Cell Biol. 102 2318–2323). It is therefore believed that the initial processes of wound healing require both the fibrin binding and cell binding domains of fibronectin. Since the attachment of fibronectin to fibrin occurs presumably via the transglutaminase—catalyzed transamidation of Gln-3 of fibronectin to fibrin lysine residues, any fibrin binding domain polypeptide that contains an intact structure of the region surrounding Gln-3 should be able to act in this system. Thus applicant's 12kD and 18.5kD polypeptide fragments of the FBD may also be used together with a CBD polypeptide to enhance wound healing. Note that recombinant CBD polypeptide may be used, such as the r33kD and r40kD described in copending PCT patent application No. WO 90/07577.

In order to assess the potential of the FBD of human fibronectin in promoting wound healing, it was tested in a cell spreading assay. In this assay fibroblasts are allowed to spread on glass coverslips to which a CBD polypeptide has been absorbed in the absence or presence of a FBD polypeptide. Thus, the FBD domain polypeptide is tested for its ability to act as an enhancer of cellular focal adhesion, as a co-substrate with fibronectin's cell binding domain. When used in combination with the 75 kD cell-binding domain (CBD) derived from bovine plasma fibronectin, the plasma-derived FBD, p31kD, and the recombinant FBD, r31kD, both from human origin, were found to be indistinguishable in their ability to promote focal adhesion of NRK fibroblasts. Both human protein domains were much more effective than the corresponding fragment from bovine origin when used at the same concentrations, i.e., 100µl of 10 µg/ml of a 1:1 mixture of FBD and CBD proteins (see below for experimental details). The difference between the effects of the 75 kD CBD alone and in combination with FBD was striking. Interference reflection microscopy (IRM) of cells spread on the 75kD CBD alone, showed only amorphous 'grey' patches and spots (which, from electron microscopy—EM—of ventral membrane replicates, are known to be associated with clathrin-based structures), but incorporation of FBD (recombinant or plasma-derived) as co-substrate induced formation of clearly-defined focal adhesion structures, visualized in IRM as dense black streaks (the density of color showing closer contact of the ventral surface to the substrate). IRM/EM correlations showed that these tight, ordered adhesions corresponded to the termini of cytoskeletal stress fibers.

For further investigation of the combined effects of the FBD and CBD on wound healing the 45 kD polypeptide (12 kD FBD–33 kD CBD) and 64 kD polypeptide (31 kD FBD–33 kD CBD) were constructed (FIGS. 12 and 25 respectively). Similar hybrid polypeptides are envisaged using 12 kD or 18.5 kD FBD instead of the 31 kD FBD and using the 40 kD CBD polypeptide instead of the 33 kD CBD polypeptide.

Experimental Details

Both the p75kD CBD (from bovine origin) and the 31kD FBD (from recombinant human origin) polypeptides at a concentration of 10μg/ml in PBS, total volume 100μl, were allowed to adsorb in a humid atmosphere for 1 hour at room temperature to 13mm glass coverslips (Chance Propper Ltd. Warley, UK), which had been treated overnight with conc. $H_2SO_4$ and rinsed extensively with distilled water. Following washing with PBS pH 7.1 the coverslips were incubated with ovalbumin (1mg/ml in PBS, Sigma Chemical Co.) for 10 min at room temperature in order to reduce non-specific attachment. The spreading assay was performed with NRK cells, subcultured for 18 hours before being detached by 0.1 mg/ml TPCK-trypsin (Sigma Chemical Co.) and resuspended in $Ca^{2+}$-containing Eagle's minimum essential medium (EMEM) for 20 min at 37°. These cells were obtained in a single-cell suspension by gentle sucking into a 5ml syringe fitted with a hypodermic needle, followed by 3 washes with EMEM containing 2% w/v ovalbumin. The spreading of the cells was monitored by resuspending the washed NRK cells on the coverslip with the protein substrate at a density of $1 \times 10^4$ cells/cm$^2$. They were examined by interference reflection and phase contrast microscopy, using a Leitz Ortholux II microscope equipped with ×50/1.0 and ×100/1.32 PHACO RK objectives and photographs were taken (Kodak technical Pan 2415 35mm film). After 2 hours the live cells were fixed with 2.5% v/v glutaraldehyde (TAAB Labs, Reading, Berks, U.K.) in 0.1M sodium cacodylate buffer and the fixed cells were examined by EM.

Example 15

$^{111}$In-DTPA modified FBD proteins with high radiochemical purity in order to obtain high thrombus to blood ratios in a rat model.

1. Modification and radiolabeling of DTPA-modified FBD proteins

The methodology of DTPA modification and the radiolabeling of DTPA-modified FBD proteins described in Example 8 have been improved. These improvements have enabled the obtaining of high thrombus to blood ratios in the coil model in rats.

1.1 DTPA-modification: All three recombinant molecules, the r31kD, r18.5 kD and r12kD, were modified with a 20-fold excess of DTPA in 0.1M HEPES buffer pH 7.0, and the excess of DTPA was removedby gel filtration.

1.2 Radiolabeling: One of the changes introduced was to perform the radiolabeling with $^{111}$InCl$_3$ at a low pH (0.2M citrate buffer, pH 5.7) in order to reduce to a minimum the amount of radiocolloids. An additional precautionary measure was taken to ensure the removal of contaminating heavy metal ions that could displace the chelated $^{111}$In from the DTPA-modified protein by exchanging the buffers of the radiolabeled FBD solution with Chelex-100-treated buffers.

2. Protocol for modification and radiolabeling of FBD proteins

The detailed improved procedure for the DTPA modification and radiolabeling of the r31 kD, the r18.5 kD and the r12 kD polypeptide fragments of the FBD is given below.

2.1. Desairing: The proteins (all in 0.5M NaCl, including millimolar concentrations of EDTA and other protease inhibitors) were desalted and transferred to HEPES buffer (0.1M pH 7). The 31 kD FBD (27 ml, 0.6 mg/ml) was desalted by dialysis, whereas both the 18.5 kD FBD (5 ml, 8.7 mg/ml) and the 12 kD FBD (5 ml, 5.6 mg/ml) were desalted on PD-10 gel filtration columns.

2.2 DTPA modification: This was carried out with a 20-fold excess of DTPA anhydride for 1 hour at room temperature in a volume of 27 ml in the case of the 31 kD FBD and 7 ml in both the cases of the 12 kD and 18.5 kD FBD proteins. Aliquots (100 μl) of the modification mixture were set aside for the determination of the number of DTPA residues that had been incorporated into the proteins and the free DTPA was removed from the rest of the materialby gel filtration on 2.6×60 cm Sephadex G-25 column, which had been pre-equilibrated and developed with the HEPES buffer. The protein-containing fractions (30 ml) were collected and the protein concentrations obtained were 0.35 mg/ml, 0.5 mg/ml and 0.9 mg/ml for the r31 kD, r18.5kD and r12kDFBD proteins, respectively. The degree of modification, which was determined byTLC on silica gel (developed in 85% methanol), was found to be 1.1, 0.8 and 1.6 for the above FBD proteins, respectively. DTPA-modified FBD proteins were stored frozen at −20° C. and thawed aliquots gave reproducible results upon radiolabeling with $^{111}$In.

2.3.Radiolabeling: The labeling was carried out with $^{111}$InCl$_3$, which had been brought to 0.2M sodium citrate, pH 5.7, by adding 125 μl of 1M sodium citrate pH 5.7 to 500 μl of the carrier-free $^{111}$InCl$_3$ stock solution ($^{111}$In: 3.2 mCi/ml). The reaction mixture for radiolabeling contained (final concentrations): FBD protein 0.2 μg/μl, HEPES 60 mM, HCl 10 mM, sodium citrate 0.2M and 111In 0.8 μCi/μl. The reaction was allowed to proceed for 1 hr at room temperature. The radiochemical purity was analyzed by TLC on silica gel (developed in 85% methanol) and for all the polypeptide fragments of the FBD it was in the range of 91%–95%. Thus, the specific activity of the radiolabeled FBD proteins is about 3.6 μCi/μg (~$8 \times 10^6$ cpm/μg). Since heavy metal ions, potentially present as trace contaminants in the buffers used during radiolabeling, might displace the $^{111}$In which is bound to the DTPA-modified FBD proteins, the radiolabeled FBD proteins were passed through a bed of 10ml of Sephadex G-25, which had been pre- equilibrated, and which was developed, with a BSA-containing BBS buffer, which had been pretreated by Chelex-100 (to remove metal ion contaminants)., 3. Biological activity The biological activity was tested with in vitro by binding of the $^{111}$In-labeled DTPA-modified FBD to preformed clots and in vivo in the steel coil-induced venous thrombi model in rats.

3.1 Binding to preformed Clots

This was performed exactly as described in Example 6 for iodinated FBD. The specific activity of the three $^{111}$In-labeled DTPA-modified FBD proteins was $6 \times 10^6$ cpm/μg protein. Results of the experiments are given in Table F (second column).

3.2 Venous thrombi in rats

The model used (coil-induced venous thrombi in rats) has been described in Example 7. In the experiments of this Example each group consisted of 7 rats to which $5\times10^6$ cpm (with a specific activity of $6\times10^6$ cpm/µg protein) of $^{111}$In labeled DTPA modified FDB protein was injected. Results of the experiments are given in Table F (3 last columns).

TABLE F

| | Binding FBD proteins thrombi in vitro and in vivo | | | |
|---|---|---|---|---|
| | In vitro | Venous thrombi in rats | | |
| FBD protein | clot assay Percent of input counts[a] | Specific radioactivity (cpm/g) | | Thrombus to Blood Ratio |
| | | Thrombus | Blood | |
| r12kD | 24% | 24264 ± 2700 | 375 ± 77 | 78.2 ± 17.3 |
| r18.5kD | 26% | 28548 ± 5028 | 289 ± 41 | 98.3 ± 13.3 |
| r31kD | 24% | 19796 ± 4144 | 1198 ± 83 | 15.6 ± 2.4 |

[a]Approximately 50% of these values are obtained in the presence of iodoacetate, an inhibitor of transglutaminase.

REFERENCES

1. Uehara, A., et al., J. Nuclear Med. 29:1264–1267 (1988).
2. Zoghbi, S. S., et al., Invest. Radio. 20:198–202 (1985).
3. Kakkar, V. V., et al., Lancet 1: 540–542 (1970).
4. Knight, L. C., Nuclear Med. Commun. 2: 849–857 (1988).
5. Knight, L. C., Nuclear Med. Commun. 2: 823–829 (1988).
6. Som. P., et al., J. Nuc. Med. 57: 1315–1320 (-1986).
7. Palabrica, T. M., et al., Proc. Nat. Acad. Sci. USA 86: 1036–40 (1989).
8. Akiyama, S. K. and Yamada, K. M., Adv. Enzymol. 57: 1–57 (1987).
9. Pierschbacher, M. D., et al., J. Biol. Chem. 257: 9593–9597 (1982).
10. Pande, H. and Shively, J. E., Arch. Biochem. Biophys. 213: 258–265 (1982).
11. Hayashi, M. and Yamada, K. M., J. Biol. Chem. 258: 3332–3340 (1983).
12. Sekiguchi, K. and Hakomori, S.-I., Proc. Natl. Acad. Sci. USA 77: 2661–2665 (1980).
13. Ruoslahti, E., et al., J. Biol. Chem. 256: 7277–7281 (1981).
14. Owens, R. J. and Baralle, F. E., EMBO J. 5: 2825–2830 (1988).
15. Obara, M., et al., FEBS Letters 213: 261–264 (-1987).
16. Obara, M., et al., Cell 53: 699 (1988).
17. Ichihara-Tanaka, K., et al., J. Biol. Chem. 265: 401–407 (1990).
18. Mandel, et al., Principal and Practice of Infectious Disease 2: 1531–1552 (1979).
19. Proctor, R. A., et al., J. Biol. Chem. 255: 1181–1188 (1980).
20. Eldor, A., et al., Thrombosis and Haemostatis 56(3): 333–339 (1986).
21. Fritzberg, A. R., Nucl. Med. 26:7–12 (1987).
22. Young, R. A. and Davis, R. W., Proc. Natl. Acad. Sci. USA 80: 1194–1198 (1983).
23. Hugh, T., et al., In DNA cloning: A practical Approach (D. Glover, ed.), IRL Press, Oxford (1984).
24. Vogel, et al., Proc. Natl. Acad. Sci. USA 69: 3180–3184 (1972).
25. Bagly, D., et al., Methods in Enzymol. 45: 669–678 (1976).
26. Wagner and Hynes, J. Biol. Chem. 254: 6746–6754 (1979).
27. McDonagh, R. P., et al., FEBS Lett. 127: 174–178 (1981).
28. Mosher, et al., J. Biol. Chem. 255: 1181–1188 (1980).
29. Russel, P. B., et al., J. Clin. Micro. 25: 1083–1087 (1987).
30. Bolton, A. E. and Hunter, W. M., Biochem. J. 133: 529 (1973).
31. Obara, et al., Cell 53: 649–657 (1988).
32. Fritzberg, A. R., et al., Proc. Natl. Acad. Sci. 85: 4025–4029 (1988).
33. Knight, L. C., et al., Radiology 173: 163–169 (-1989).
34. Wasser, M. N. J. M., et al., Blood 74: 708–714 (-1989).
35. Burger, J. J., et al., Methods in Enzymology 112: 43–56 (1985).
36. Yamamoto, K., et al., Eur. J. Nucl. Med. 14: 60–64 (1988).
37. Peterson, et al., in *Fibronectin*, edited by Moshen, Academic Press, USA, 1989: page 1–24, particularly FIG. 2 on page 5.

What is claimed is:

1. A method for imaging a fibrin-containing substance which comprises contacting the fibrin-containing substance to be imaged with an imaging agent which comprises a polypeptide labeled with an imageable marker, such polypeptide havinq an amino acid sequence substantially identical to a sequence present in the fibrin binding domain of naturally occurrinq human fibronectin, beinq capable of binding to fibrin, having a molecular weiqht above about 6 kD but less than about 20 kD, and having the amino acid sequence gln-ala-gln-gln or met-gln-ala-gln-gln at the N-terminus of the polypeptide under conditions such that the agent binds to the fibrin-containing substance and imaging bound agent and thereby imaging the fibrin-containing substance.

2. A method of claim 1, wherein the fibrin-containing substance is a thrombus.

3. A method of claim 1, wherein the fibrin-containing substance is atherosclerotic plaque.

4. A method for imaging a fibrin-containing substance in a subject which comprises:

(a) administering to the subject a composition comprising an effective imaging amount of the imaging agent used in claim 1 and a physiologically. acceptable carrier under conditions permitting the imaging agent container therein to enter the blood stream and bind to fibrin present in the blood vessels;

(b) imaging bound agent within the blood vessels; and thereby (c) imaging the fibrin-containing substance.

5. A method of claim 4, wherein the fibrin-containing substance is a thrombus.

6. A method of claim 4, wherein the fibrin-containing substance is atherosclerotic plaque.

7. A method of claim 1, wherein the polypeptide is an 18.5 kD polypeptide wherein the amino acid sequence substantially identical to a sequence present in the fibrin binding domain of human fibronectin is the sequence of amino acids 1-154 as shown in FIG. 2.

8. A method of claim 16, wherein the polypeptide comprises a 20 kD polypeptide wherein the amino acid sequence substantially identical to a sequence present in the fibrin binding domain of human fibronectin is the sequence of amino acids 1-153 as shown in FIG. 2 (SEQ ID NO. 16).

9. A method of claim 8, wherein the 20 kD polypeptide comprises less than about 20 additional amino acids to the C-terminal of the sequence of amino acids 1-153 as shown in FIG. 2A.

10. A method of claim 1, wherein the polypeptide is a 12 kD polypeptide wherein the amino acid sequence substantially identical to a sequence present in the fibrin binding domain of human fibronectin is the sequence of amino acids 1-109 as shown in FIG. 2 (SEQ ID NO. 16).

11. A method of claim 1, wherein the marker is a radioactive isotope, an element which is opaque to X-rays, or a paramagnetic ion.

12. A method of claim 1, wherein the imaging is carried out using a gamma camera.

13. A method for imaging a fibrin-containing substance which comprises contacting the fibrin-containing substance to be imaged with an imaging agent which comprises a polypeptide labeled with an imageable marker, such polypeptide comprising a 12 kD amino acid sequence encoded by plasmid pFN 203-2 (ATCC 68606), being capable of binding to fibrin, and having a molecular weight from about 12 kD up to about 20 kD, and having the amino acid sequence gln-ala-gln-gln or met-gln-ala-gln-gln at the N-terminus of the potypeptide under conditions such that the agent binds to the fibrin-containing substance and imaging bound agent and thereby imaging the fibrin-containing substance.

* * * * *

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
  ( A ) LENGTH: 4 amino acids
  ( B ) TYPE: amino acid
  ( C ) STRANDEDNESS: single
  ( D ) TOPOLOGY: linear ( i i ) MOLECULE TYPE: protein ( i i i ) HYPOTHETICAL: NO (iv) ANTI-SENSE: NO (v) FRAGMENT TYPE: N-terminal (ix) FEATURE:
        (A) NAME/KEY: Peptide
        (B) LOCATION: 1..4

(xi) SEQUENCE DESCRIPTION: SEQ ID NO:1:

Gln Ala Gln Gln
    1

(2) INFORMATION FOR SEQ ID NO:2:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

CTGTTTAAGC A 11

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:3:

GATCTGCTTA AACAG 15

(2) INFORMATION FOR SEQ ID NO:4:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:4:

Asp Gly Arg Gly Asp Ser
    1               5

(2) INFORMATION FOR SEQ ID NO:5:

(i) SEQUENCE CHARACTERISTICS:
        (A) LENGTH: 5 amino acids
        (B) TYPE: amino acid
        (C) STRANDEDNESS: single ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:5:

His Asp Val Leu Lys
1               5

( 2 ) INFORMATION FOR SEQ ID NO:6:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:6:

Arg Ala Ala Val
1

( 2 ) INFORMATION FOR SEQ ID NO:7:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:7:

Gly Arg Gly Asp Ser
1               5

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:8:

Met Gln Ala Gln Gln
1               5

( 2 ) INFORMATION FOR SEQ ID NO:9:

( i ) SEQUENCE CHARACTERISTICS:
        ( A ) LENGTH: 38 base pairs (B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:9:

CCTCCTGTTT CTCCGTAAGT GATCCTGTAA TATCTCAC 38

(2) INFORMATION FOR SEQ ID NO:10:

(i) SEQUENCE CHARACTERISTICS:
(A) LENGTH: 33 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:10:

GAATCAAGAC CTGTTTTCTG TCTTCCTCTA AGA 33

(2) INFORMATION FOR SEQ ID NO:11:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:11:

CCAGGTCCCT CGGAACATCA GAAACTGTTG ATTGTTGGCC 40

(2) INFORMATION FOR SEQ ID NO:12:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:12:

AATTCTGTGA CACAGTGGCC ATAGGGAGGC TGGGGG 36

(2) INFORMATION FOR SEQ ID NO:13:

(i) SEQUENCE CHARACTERISTICS:
(A) LENGTH: 42 base pairs
(B) TYPE: nucleic acid
(C) STRANDEDNESS: single
(D) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:13:

CATGACCCCT TCATTGGTTG TGCAGATTTC CTCGTGGCCA GC   42

( 2 ) INFORMATION FOR SEQ ID NO:14:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:14:

CTGTTTAATA AGCA   14

( 2 ) INFORMATION FOR SEQ ID NO:15:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:15:

GATCTGCTTA AACAG   15

( 2 ) INFORMATION FOR SEQ ID NO:16:

( i ) SEQUENCE CHARACTERISTICS:
        ( A ) LENGTH: 7705 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 5..7681

( x i ) SEQUENCE DESCRIPTION: SEQ ID NO:16:

```
GAAG AGC AAG AGG CAG GCT CAG CAA ATG GTT CAG CCC CAG TCC CCG GTG      49
     Ser Lys Arg Gln Ala Gln Gln Met Val Gln Pro Gln Ser Pro Val
      1               5                  10                  15

GCT GTC AGT CAA AGC AAG CCC GGT TGT TAT GAC AAT GGA AAA CAC TAT       97
Ala Val Ser Gln Ser Lys Pro Gly Cys Tyr Asp Asn Gly Lys His Tyr
                 20                  25                  30

CAG ATA AAT CAA CAG TGG GAG CGG ACC TAC CTA GGT AAT GTG TTG GTT      145
Gln Ile Asn Gln Gln Trp Glu Arg Thr Tyr Leu Gly Asn Val Leu Val
             35                  40                  45
```

| | | | | | | | | | | | | | | | | |
|---|---|---|---|---|---|---|---|---|---|---|---|---|---|---|---|---|
| TGT | ACT | TGT | TAT | GGA | GGA | AGC | CGA | GGT | TTT | AAC | TGC | GAA | AGT | AAA | CCT | 193 |
| Cys | Thr | Cys 50 | Tyr | Gly | Gly | Ser 55 | Arg | Gly | Phe | Asn | Cys 60 | Glu | Ser | Lys | Pro | |
| GAA | GCT | GAA | GAG | ACT | TGC | TTT | GAC | AAG | TAC | ACT | GGG | AAC | ACT | TAC | CGA | 241 |
| Glu | Ala 65 | Glu | Glu | Thr | Cys 70 | Phe | Asp | Lys | Tyr | Thr 75 | Gly | Asn | Thr | Tyr | Arg | |
| GTG | GGT | GAC | ACT | TAT | GAG | CGT | CCT | AAA | GAC | TCC | ATG | ATC | TGG | GAC | TGT | 289 |
| Val 80 | Gly | Asp | Thr | Tyr | Glu 85 | Arg | Pro | Lys | Asp | Ser 90 | Met | Ile | Trp | Asp | Cys 95 | |
| ACC | TGC | ATC | GGG | GCT | GGG | CGA | GGG | AGA | ATA | AGC | TGT | ACC | ATC | GCA | AAC | 337 |
| Thr | Cys | Ile | Gly | Ala 100 | Gly | Arg | Gly | Arg | Ile 105 | Ser | Cys | Thr | Ile | Ala 110 | Asn | |
| CGC | TGC | CAT | GAA | GGG | GGT | CAG | TCC | TAC | AAG | ATT | GGT | GAC | ACC | TGG | AGG | 385 |
| Arg | Cys | His | Glu 115 | Gly | Gly | Gln | Ser | Tyr 120 | Lys | Ile | Gly | Asp | Thr 125 | Trp | Arg | |
| AGA | CCA | CAT | GAG | ACT | GGT | GGT | TAC | ATG | TTA | GAG | TGT | GTG | TGT | CTT | GGT | 433 |
| Arg | Pro | His 130 | Glu | Thr | Gly | Gly | Tyr 135 | Met | Leu | Glu | Cys | Val 140 | Cys | Leu | Gly | |
| AAT | GGA | AAA | GGA | GAA | TGG | ACC | TGC | AAG | CCC | ATA | GCT | GAG | AAG | TGT | TTT | 481 |
| Asn | Gly 145 | Lys | Gly | Glu | Trp | Thr 150 | Cys | Lys | Pro | Ile | Ala 155 | Glu | Lys | Cys | Phe | |
| GAT | CAT | GCT | GCT | GGG | ACT | CCC | TAT | GTG | GTC | GGA | GAA | ACG | TGG | GAG | AAG | 529 |
| Asp 160 | His | Ala | Ala | Gly | Thr 165 | Pro | Tyr | Val | Val | Gly 170 | Glu | Thr | Trp | Glu | Lys 175 | |
| CCC | TAC | CAA | GGC | TGG | ATG | ATG | GTA | GAT | TGT | ACT | TGC | CTG | GGA | GAA | GGC | 577 |
| Pro | Tyr | Gln | Gly | Trp 180 | Met | Met | Val | Asp | Cys 185 | Thr | Cys | Leu | Gly | Glu 190 | Gly | |
| AGC | GGA | CGC | ATC | ACT | TGC | ACT | TCT | AGA | AAT | AGA | TGC | AAC | GAT | CAG | GAC | 625 |
| Ser | Gly | Arg | Ile 195 | Thr | Cys | Thr | Ser | Arg 200 | Asn | Arg | Cys | Asn | Asp 205 | Gln | Asp | |
| ACA | AGG | ACA | TCC | TAT | AGA | ATT | TGA | GAC | ACC | TGG | AGC | AAG | AAG | GAT | AAT | 673 |
| Thr | Arg | Thr 210 | Ser | Tyr | Arg | Ile | * 215 | Asp | Thr | Trp | Ser | Lys 220 | Lys | Asp | Asn | |
| CGA | GGA | AAC | CTG | CTC | CAG | TGC | ATC | TGC | ACA | GGC | AAC | GGC | CGA | GGA | GAG | 721 |
| Arg | Gly | Asn 225 | Leu | Leu | Gln | Cys | Ile 230 | Cys | Thr | Gly | Asn | Gly 235 | Arg | Gly | Glu | |
| TGG | AAG | TGT | GAG | AGG | CAC | ACC | TCT | GTG | CAG | ACC | ACA | TCG | AGC | GGA | TCT | 769 |
| Trp 240 | Lys | Cys | Glu | Arg | His 245 | Thr | Ser | Val | Gln | Thr 250 | Thr | Ser | Ser | Gly | Ser 255 | |
| GGC | CCC | TTC | ACC | GAT | GTT | CGT | GCA | GCT | GTT | TAC | CAA | CCG | CAG | CCT | CAC | 817 |
| Gly | Pro | Phe | Thr | Asp 260 | Val | Arg | Ala | Ala | Val 265 | Tyr | Gln | Pro | Gln | Pro 270 | His | |
| CCC | CAG | CCT | CCT | CCC | TAT | GGC | CAC | TGT | GTC | ACA | GAC | AGT | GGT | GTG | GTC | 865 |
| Pro | Gln | Pro | Pro 275 | Pro | Tyr | Gly | His | Cys 280 | Val | Thr | Asp | Ser | Gly 285 | Val | Val | |
| TAC | TCT | GTG | GGG | ATG | CAG | TGG | TTG | AAG | ACA | CAA | GGA | AAT | AAG | CAA | ATG | 913 |
| Tyr | Ser | Val | Gly 290 | Met | Gln | Trp | Leu | Lys 295 | Thr | Gln | Gly | Asn | Lys 300 | Gln | Met | |
| CTT | TGC | ACG | TGC | CTG | GGC | AAC | GGA | GTC | AGC | TGC | CAA | GAG | ACA | GCT | GTA | 961 |
| Leu | Cys | Thr 305 | Cys | Leu | Gly | Asn | Gly 310 | Val | Ser | Cys | Gln | Glu 315 | Thr | Ala | Val | |
| ACC | CAG | ACT | TAC | GGT | GGC | AAC | TTA | AAT | GGA | GAG | CCA | TGT | GTC | TTA | CCA | 1009 |
| Thr | Gln | Thr 320 | Tyr | Gly | Gly | Asn 325 | Leu | Asn | Gly | Glu | Pro 330 | Cys | Val | Leu | Pro 335 | |
| TTC | ACC | TAC | AAT | GGC | AGG | ACG | TTC | TAC | TCC | TGC | ACC | ACG | GAA | GGG | CGA | 1057 |
| Phe | Thr | Tyr | Asn | Gly 340 | Arg | Thr | Phe | Tyr | Ser 345 | Cys | Thr | Thr | Glu | Gly 350 | Arg | |
| CAG | GAC | GGA | CAT | CTT | TGG | TGC | AGC | ACA | ACT | TCG | AAT | TAT | GAG | CAG | GAC | 1105 |
| Gln | Asp | Gly | His | Leu 355 | Trp | Cys | Ser | Thr 360 | Thr | Ser | Asn | Tyr | Glu 365 | Gln | Asp | |

| | | | | | | | | | | | | | | | | |
|---|---|---|---|---|---|---|---|---|---|---|---|---|---|---|---|---|
| CAG | AAA | TAC | TCT | TTC | TGC | ACA | GAC | CAC | ACT | GTT | TTG | GTT | CAG | ACT | CAA | 1153 |
| Gln | Lys | Tyr 370 | Ser | Phe | Cys | Thr 375 | Asp | His | Thr | Val | Leu 380 | Val | Gln | Thr | Gln | |
| GGA | GGA | AAT | TCC | AAT | GGT | GCC | TTG | TGC | CAC | TTC | CCC | TTC | CTA | TAC | AAC | 1201 |
| Gly | Gly | Asn 385 | Ser | Asn | Gly | Ala 390 | Leu | Cys | His | Phe | Pro 395 | Phe | Leu | Tyr | Asn | |
| AAC | CAC | AAT | TAC | ACT | GAT | TGC | ACT | TCT | GAG | GGC | AGA | AGA | GAC | AAC | ATG | 1249 |
| Asn 400 | His | Asn | Tyr | Thr | Asp 405 | Cys | Thr | Ser | Glu | Gly 410 | Arg | Arg | Asp | Asn | Met 415 | |
| AAG | TGG | TGT | GGG | ACC | ACA | CAG | AAC | TAT | GAT | GCC | GAC | CAG | AAG | TTT | GGG | 1297 |
| Lys | Trp | Cys | Gly | Thr 420 | Thr | Gln | Asn | Tyr | Asp 425 | Ala | Asp | Gln | Lys | Phe 430 | Gly | |
| TTC | TGC | CCC | ATG | GCT | GCC | CAC | GAG | GAA | ATC | TGC | ACA | ACC | AAT | GAA | GGG | 1345 |
| Phe | Cys | Pro | Met 435 | Ala | Ala | His | Glu | Glu 440 | Ile | Cys | Thr | Thr | Asn 445 | Glu | Gly | |
| GTC | ATG | TAC | CGC | ATT | GGA | GAT | CAG | TGG | GAT | AAG | CAG | CAT | GAC | ATG | GGT | 1393 |
| Val | Met | Tyr 450 | Arg | Ile | Gly | Asp | Gln 455 | Trp | Asp | Lys | Gln | His 460 | Asp | Met | Gly | |
| CAC | ATG | ATG | AGG | TGC | ACG | TGT | GTT | GGG | AAT | GGT | CGT | GGG | GAA | TGG | ACA | 1441 |
| His | Met 465 | Met | Arg | Cys | Thr | Cys 470 | Val | Gly | Asn | Gly | Arg 475 | Gly | Glu | Trp | Thr | |
| TGC | ATT | GCC | TAC | TCG | CAA | CTT | CGA | GAT | CAG | TGC | ATT | GTT | GAT | GAC | ATC | 1489 |
| Cys 480 | Ile | Ala | Tyr | Ser | Gln 485 | Leu | Arg | Asp | Gln | Cys 490 | Ile | Val | Asp | Asp | Ile 495 | |
| ACT | TAC | AAT | GTG | AAC | GAC | ACA | TTC | CAC | AAG | CGT | CAT | GAA | GAG | GGG | CAC | 1537 |
| Thr | Tyr | Asn | Val | Asn 500 | Asp | Thr | Phe | His | Lys 505 | Arg | His | Glu | Glu | Gly 510 | His | |
| ATG | CTG | AAC | TGT | ACA | TGC | TTC | GGT | CAG | GGT | CGG | GGC | AGG | TGG | AAG | TGT | 1585 |
| Met | Leu | Asn | Cys 515 | Thr | Cys | Phe | Gly | Gln 520 | Gly | Arg | Gly | Arg | Trp 525 | Lys | Cys | |
| GAT | CCC | GTC | GAC | CAA | TGC | CAG | GAT | TCA | GAG | ACT | GGG | ACG | TTT | TAT | CAA | 1633 |
| Asp | Pro | Val | Asp 530 | Gln | Cys | Gln | Asp | Ser 535 | Glu | Thr | Gly | Thr | Phe 540 | Tyr | Gln | |
| ATT | GGA | GAT | TCA | TGG | GAG | AAG | TAT | GTG | CAT | GGT | GTC | AGA | TAC | CAG | TGC | 1681 |
| Ile | Gly | Asp | Ser | Trp 545 | Glu | Lys | Tyr | Val | His 550 | Gly | Val | Arg | Tyr | Gln 555 | Cys | |
| TAC | TGC | TAT | GGC | CGT | GGC | ATT | GGG | GAG | TGG | CAT | TGC | CAA | CCT | TTA | CAG | 1729 |
| Tyr 560 | Cys | Tyr | Gly | Arg | Gly 565 | Ile | Gly | Glu | Trp | His 570 | Cys | Gln | Pro | Leu | Gln 575 | |
| ACC | TAT | CCA | AGC | TCA | AGT | GGT | CCT | GTC | GAA | GTA | TTT | ATC | ACT | GAG | ACT | 1777 |
| Thr | Tyr | Pro | Ser | Ser 580 | Ser | Gly | Pro | Val | Glu 585 | Val | Phe | Ile | Thr | Glu 590 | Thr | |
| CCG | AGT | CAG | CCC | AAC | TCC | CAC | CCC | ATC | CAG | TGG | AAT | GCA | CCA | CAG | CCA | 1825 |
| Pro | Ser | Gln | Pro 595 | Asn | Ser | His | Pro | Ile 600 | Gln | Trp | Asn | Ala | Pro 605 | Gln | Pro | |
| TCT | CAC | ATT | TCC | AAG | TAC | ATT | CTC | AGG | TGG | AGA | CCT | AAA | AAT | TCT | GTA | 1873 |
| Ser | His | Ile 610 | Ser | Lys | Tyr | Ile | Leu 615 | Arg | Trp | Arg | Pro | Lys 620 | Asn | Ser | Val | |
| GGC | CGT | TGG | AAG | GAA | GCT | ACC | ATA | CCA | GGC | CAC | TTA | AAC | TCC | TAC | ACC | 1921 |
| Gly | Arg 625 | Trp | Lys | Glu | Ala | Thr 630 | Ile | Pro | Gly | His | Leu 635 | Asn | Ser | Tyr | Thr | |
| ATC | AAA | GGC | CTG | AAG | CCT | GGT | GTG | GTA | TAC | GAG | GGC | CAG | CTC | ATC | AGC | 1969 |
| Ile 640 | Lys | Gly | Leu | Lys | Pro 645 | Gly | Val | Val | Tyr | Glu 650 | Gly | Gln | Leu | Ile | Ser 655 | |
| ATC | CAG | CAG | TAC | GGC | CAC | CAA | GAA | GTG | ACT | CGC | TTT | GAC | TTC | ACC | ACC | 2017 |
| Ile | Gln | Gln | Tyr | Gly 660 | His | Gln | Glu | Val | Thr 665 | Arg | Phe | Asp | Phe | Thr 670 | Thr | |
| ACC | AGC | ACC | AGC | ACA | CCT | GTG | ACC | AGC | AAC | ACC | GTG | ACA | GGA | GAG | ACG | 2065 |
| Thr | Ser | Thr | Ser 675 | Thr | Pro | Val | Thr | Ser 680 | Asn | Thr | Val | Thr | Gly 685 | Glu | Thr | |

| | | | | | | | | | | | | | | | | |
|---|---|---|---|---|---|---|---|---|---|---|---|---|---|---|---|---|
| ACT | CCC | TTT | TCT | CCT | CTT | GTG | GCC | ACT | TCT | GAA | TCT | GTG | ACC | GAA | ATC | 2113 |
| Thr | Pro | Phe 690 | Ser | Pro | Leu | Val | Ala 695 | Thr | Ser | Glu | Ser | Val 700 | Thr | Glu | Ile | |
| ACA | GCC | AGT | AGC | TTT | GTG | GTC | TCC | TGG | GTC | TCA | GCT | TCC | GAC | ACC | GTG | 2161 |
| Thr | Ala 705 | Ser | Ser | Phe | Val | Val 710 | Ser | Trp | Val | Ser | Ala 715 | Ser | Asp | Thr | Val | |
| TCG | GGA | TTC | CGG | GTG | GAA | TAT | GAG | CTG | AGT | GAG | GAG | GGA | GAT | GAG | CCA | 2209 |
| Ser | Gly 720 | Phe | Arg | Val | Glu 725 | Tyr | Glu | Leu | Ser | Glu 730 | Glu | Gly | Asp | Glu | Pro 735 | |
| CAG | TAC | CTG | GAT | CTT | CCA | AGC | ACA | GCC | ACT | TCT | GTG | AAC | ATC | CCT | GAC | 2257 |
| Gln | Tyr | Leu | Asp | Leu 740 | Pro | Ser | Thr | Ala | Thr 745 | Ser | Val | Asn | Ile | Pro 750 | Asp | |
| CTG | CTT | CCT | GGC | CGA | AAA | TAC | ATT | GTA | AAT | GTC | TAT | CAG | ATA | TCT | GAG | 2305 |
| Leu | Leu | Pro | Gly 755 | Arg | Lys | Tyr | Ile | Val 760 | Asn | Val | Tyr | Gln | Ile 765 | Ser | Glu | |
| GAT | GGG | GAG | CAG | AGT | TTG | ATC | CTG | TCT | ACT | TCA | CAA | ACA | ACA | GCG | CCT | 2353 |
| Asp | Gly | Glu 770 | Gln | Ser | Leu | Ile | Leu 775 | Ser | Thr | Ser | Gln | Thr 780 | Thr | Ala | Pro | |
| GAT | GCC | CCT | CCT | GAC | CCG | ACT | GTG | GAC | CAA | GTT | GAT | GAC | ACC | TCA | ATT | 2401 |
| Asp | Ala 785 | Pro | Pro | Asp | Pro 790 | Thr | Val | Asp | Gln | Val 795 | Asp | Asp | Thr | Ser | Ile | |
| GTT | GTT | CGC | TGG | AGC | AGA | CCC | CAG | GCT | CCC | ATC | ACA | GGG | TAC | AGA | ATA | 2449 |
| Val 800 | Val | Arg | Trp | Ser | Arg 805 | Pro | Gln | Ala | Pro | Ile 810 | Thr | Gly | Tyr | Arg | Ile 815 | |
| GTC | TAT | TCG | CCA | TCA | GTA | GAA | GGT | AGC | AGC | ACA | GAA | CTC | AAC | CTT | CCT | 2497 |
| Val | Tyr | Ser | Pro | Ser 820 | Val | Glu | Gly | Ser | Ser 825 | Thr | Glu | Leu | Asn | Leu 830 | Pro | |
| GAA | ACT | GCA | AAC | TCC | GTC | ACC | CTC | AGT | GAC | TTG | CAA | CCT | GGT | GTT | CAG | 2545 |
| Glu | Thr | Ala | Asn 835 | Ser | Val | Thr | Leu | Ser 840 | Asp | Leu | Gln | Pro | Gly 845 | Val | Gln | |
| TAT | AAC | ATC | ACT | ATC | TAT | GCT | GTG | GAA | GAA | AAT | CAA | GAA | AGT | ACA | CCT | 2593 |
| Tyr | Asn | Ile 850 | Thr | Ile | Tyr | Ala | Val 855 | Glu | Glu | Asn | Gln | Glu 860 | Ser | Thr | Pro | |
| GTT | GTC | ATT | CAA | CAA | GAA | ACC | ACT | GGC | ACC | CCA | CGC | TCA | GAT | ACA | GTG | 2641 |
| Val | Val 865 | Ile | Gln | Gln | Glu | Thr 870 | Thr | Gly | Thr | Pro | Arg 875 | Ser | Asp | Thr | Val | |
| CCC | TCT | CCC | AGG | GAC | CTG | CAG | TTT | GTG | GAA | GTG | ACA | GAC | GTG | AAG | GTC | 2689 |
| Pro | Ser | Pro 880 | Arg | Asp | Leu | Gln | Phe 885 | Val | Glu | Val | Thr | Asp 890 | Val | Lys | Val 895 | |
| ACC | ATC | ATG | TGG | ACA | CCG | CCT | GAG | AGT | GCA | GTG | ACC | GGC | TAC | CGT | GTG | 2737 |
| Thr | Ile | Met | Trp 900 | Thr | Pro | Pro | Glu | Ser 905 | Ala | Val | Thr | Gly | Tyr 910 | Arg | Val | |
| GAT | GTG | ATC | CCC | GTC | AAC | CTG | CCT | GGC | GAG | CAC | GGG | CAG | AGG | CTG | CCC | 2785 |
| Asp | Val | Ile | Pro 915 | Val | Asn | Leu | Pro | Gly 920 | Glu | His | Gly | Gln | Arg 925 | Leu | Pro | |
| ATC | AGC | AGG | AAC | ACC | TTT | GCA | GAA | GTC | ACC | GGG | CTG | TCC | CCT | GGG | GTC | 2833 |
| Ile | Ser | Arg 930 | Asn | Thr | Phe | Ala | Glu 935 | Val | Thr | Gly | Leu | Ser 940 | Pro | Gly | Val | |
| ACC | TAT | TAC | TTC | AAA | GTC | TTT | GCA | GTG | AGC | CAT | GGG | AGG | GAG | AGC | AAG | 2881 |
| Thr | Tyr 945 | Tyr | Phe | Lys | Val | Phe 950 | Ala | Val | Ser | His | Gly 955 | Arg | Glu | Ser | Lys | |
| CCT | CTG | ACT | GCT | CAA | CAG | ACA | ACC | AAA | CTG | GAT | GCT | CCC | ACT | AAC | CTC | 2929 |
| Pro | Leu | Thr 960 | Ala | Gln | Gln | Thr | Thr 965 | Lys | Leu | Asp | Ala | Pro 970 | Thr | Asn | Leu 975 | |
| CAG | TTT | GTC | AAT | GAA | ACT | GAT | TCT | ACT | GTC | CTG | GTG | AGA | TGG | ACT | CCA | 2977 |
| Gln | Phe | Val | Asn 980 | Glu | Thr | Asp | Ser | Thr 985 | Val | Leu | Val | Arg | Trp 990 | Thr | Pro | |
| CCT | CGG | GCC | CAG | ATA | ACA | GGA | TAC | CGA | CTG | ACC | GTG | GGC | CTT | ACC | CGA | 3025 |
| Pro | Arg | Ala | Gln | Ile 995 | Thr | Gly | Tyr | Arg | Leu 1000 | Thr | Val | Gly | Leu | Thr 1005 | Arg | |

-continued

| | | | | | | | | | | | | | | | | |
|---|---|---|---|---|---|---|---|---|---|---|---|---|---|---|---|---|
| AGA | GGC | CAG | CCC | AGG | CAG | TAC | AAT | GTG | GGT | CCC | TCT | GTC | TTC | AAG | TAC | 3073 |
| Arg | Gly | Gln | Pro | Arg | Gln | Tyr | Asn | Val | Gly | Pro | Ser | Val | Phe | Lys | Tyr | |
| | | 1010 | | | | 1015 | | | | 1020 | | | | | | |
| CCC | CTG | AGG | AAT | CTG | CAG | CCT | GCA | TCT | GAG | TAC | ACC | GTA | TCC | CTC | GTG | 3121 |
| Pro | Leu | Arg | Asn | Leu | Gln | Pro | Ala | Ser | Glu | Tyr | Thr | Val | Ser | Leu | Val | |
| | | 1025 | | | | 1030 | | | | 1035 | | | | | | |
| GCC | ATA | AAG | GGC | AAC | CAA | GAG | AGC | CCC | AAA | GCC | ACT | GGA | GTC | TTT | ACC | 3169 |
| Ala | Ile | Lys | Gly | Asn | Gln | Glu | Ser | Pro | Lys | Ala | Thr | Gly | Val | Phe | Thr | |
| 1040 | | | | 1045 | | | | 1050 | | | | | | | 1055 | |
| ACA | CTG | CAG | CCT | GGG | AGC | TCT | ATT | CCA | CCT | TAC | AAC | ACC | GAG | GTG | ACT | 3217 |
| Thr | Leu | Gln | Pro | Gly | Ser | Ser | Ile | Pro | Pro | Tyr | Asn | Thr | Glu | Val | Thr | |
| | | | | 1060 | | | | 1065 | | | | 1070 | | | | |
| GAG | ACC | ACC | ATC | GTG | ATC | ACA | TGG | ACG | CCT | GCT | CCA | AGA | ATT | GGT | TTT | 3265 |
| Glu | Thr | Thr | Ile | Val | Ile | Thr | Trp | Thr | Pro | Ala | Pro | Arg | Ile | Gly | Phe | |
| | | | | 1075 | | | | 1080 | | | | | | 1085 | | |
| AAG | CTG | GGT | GTA | CGA | CCA | AGC | CAG | GGA | GGA | GAG | GCA | CCA | CGA | GAA | GTG | 3313 |
| Lys | Leu | Gly | Val | Arg | Pro | Ser | Gln | Gly | Gly | Glu | Ala | Pro | Arg | Glu | Val | |
| | | | 1090 | | | | 1095 | | | | 1100 | | | | | |
| ACT | TCA | GAC | TCA | GGA | AGC | ATC | GTT | GTG | TCC | GGC | TTG | ACT | CCA | GGA | GTA | 3361 |
| Thr | Ser | Asp | Ser | Gly | Ser | Ile | Val | Val | Ser | Gly | Leu | Thr | Pro | Gly | Val | |
| | | 1105 | | | | 1110 | | | | | | 1115 | | | | |
| GAA | TAC | GTC | TAC | ACC | ATC | CAA | GTC | CTG | AGA | GAT | GGA | CAG | GAA | AGA | GAT | 3409 |
| Glu | Tyr | Val | Tyr | Thr | Ile | Gln | Val | Leu | Arg | Asp | Gly | Gln | Glu | Arg | Asp | |
| 1120 | | | | | 1125 | | | | 1130 | | | | | | 1135 | |
| GCG | CCA | ATT | GTA | AAC | AAA | GTG | GTG | ACA | CCA | TTG | TCT | CCA | CCA | ACA | AAC | 3457 |
| Ala | Pro | Ile | Val | Asn | Lys | Val | Val | Thr | Pro | Leu | Ser | Pro | Pro | Thr | Asn | |
| | | | | | 1140 | | | | 1145 | | | | | 1150 | | |
| TTG | CAT | CTG | GAG | GCA | AAC | CCT | GAC | ACT | GGA | GTG | CTC | ACA | GTC | TCC | TGG | 3505 |
| Leu | His | Leu | Glu | Ala | Asn | Pro | Asp | Thr | Gly | Val | Leu | Thr | Val | Ser | Trp | |
| | | | | 1155 | | | | | 1160 | | | | 1165 | | | |
| GAG | AGG | AGC | ACC | ACC | CCA | GAC | ATT | ACT | GGT | TAT | AGA | ATT | ACC | ACA | ACC | 3553 |
| Glu | Arg | Ser | Thr | Thr | Pro | Asp | Ile | Thr | Gly | Tyr | Arg | Ile | Thr | Thr | Thr | |
| | | 1170 | | | | 1175 | | | | | | 1180 | | | | |
| CCT | ACA | AAC | GGC | CAG | CAG | GGA | AAT | TCT | TTG | GAA | GAA | GTG | GTC | CAT | GCT | 3601 |
| Pro | Thr | Asn | Gly | Gln | Gln | Gly | Asn | Ser | Leu | Glu | Glu | Val | Val | His | Ala | |
| | 1185 | | | | | 1190 | | | | | 1195 | | | | | |
| GAT | CAG | AGC | TCC | TGC | ACT | TTT | GAT | AAC | CTG | AGT | CCC | GGC | CTG | GAG | TAC | 3649 |
| Asp | Gln | Ser | Ser | Cys | Thr | Phe | Asp | Asn | Leu | Ser | Pro | Gly | Leu | Glu | Tyr | |
| 1200 | | | | | 1205 | | | | | 1210 | | | | | 1215 | |
| AAT | GTC | AGT | GTT | TAC | ACT | GTC | AAG | GAT | GAC | AAG | GAA | AGT | GTC | CCT | ATC | 3697 |
| Asn | Val | Ser | Val | Tyr | Thr | Val | Lys | Asp | Asp | Lys | Glu | Ser | Val | Pro | Ile | |
| | | | | 1220 | | | | | 1225 | | | | | 1230 | | |
| TCT | GAT | ACC | ATC | ATC | CCA | GCT | GTT | CCT | CCT | CCC | ACT | GAC | CTG | CGA | TTC | 3745 |
| Ser | Asp | Thr | Ile | Ile | Pro | Ala | Val | Pro | Pro | Pro | Thr | Asp | Leu | Arg | Phe | |
| | | | 1235 | | | | 1240 | | | | | 1245 | | | | |
| ACC | AAC | ATT | GGT | CCA | GAC | ACC | ATG | CGT | GTC | ACC | TGG | GCT | CCA | CCC | CCA | 3793 |
| Thr | Asn | Ile | Gly | Pro | Asp | Thr | Met | Arg | Val | Thr | Trp | Ala | Pro | Pro | Pro | |
| | | | 1250 | | | | 1255 | | | | | 1260 | | | | |
| TCC | ATT | GAT | TTA | ACC | AAC | TTC | CTG | GTG | CGT | TAC | TCA | CCT | GTG | AAA | AAT | 3841 |
| Ser | Ile | Asp | Leu | Thr | Asn | Phe | Leu | Val | Arg | Tyr | Ser | Pro | Val | Lys | Asn | |
| | 1265 | | | | | 1270 | | | | 1275 | | | | | | |
| GAG | GAA | GAT | GTT | GCA | GAG | TTG | TCA | ATT | TCT | CCT | TCA | GAC | AAT | GCA | GTG | 3889 |
| Glu | Glu | Asp | Val | Ala | Glu | Leu | Ser | Ile | Ser | Pro | Ser | Asp | Asn | Ala | Val | |
| 1280 | | | | 1285 | | | | 1290 | | | | | | 1295 | | |
| GTC | TTA | ACA | AAT | CTC | CTG | CCT | GGT | ACA | GAA | TAT | GTA | GTG | AGT | GTC | TCC | 3937 |
| Val | Leu | Thr | Asn | Leu | Leu | Pro | Gly | Thr | Glu | Tyr | Val | Val | Ser | Val | Ser | |
| | | | | 1300 | | | | 1305 | | | | 1310 | | | | |
| AGT | GTC | TAC | GAA | CAA | CAT | GAG | AGC | ACA | CCT | CTT | AGA | GGA | AGA | CAG | AAA | 3985 |
| Ser | Val | Tyr | Glu | Gln | His | Glu | Ser | Thr | Pro | Leu | Arg | Gly | Arg | Gln | Lys | |
| | | | 1315 | | | | 1320 | | | | | 1325 | | | | |

```
ACA GGT CTT GAT TCC CCA ACT GGC ATT GAC TTT TCT GAT ATT ACT GCC        4033
Thr Gly Leu Asp Ser Pro Thr Gly Ile Asp Phe Ser Asp Ile Thr Ala
        1330            1335            1340

AAC TCT TTT ACT GTG CAC TGG ATT GCT CCT CGA GCC ACC ATC ACT GGC        4081
Asn Ser Phe Thr Val His Trp Ile Ala Pro Arg Ala Thr Ile Thr Gly
        1345            1350            1355

TAC AGG ATC CGC CAT CAT CCC GAG CAC TTC AGT GGG AGA CCT CGA GAA        4129
Tyr Arg Ile Arg His His Pro Glu His Phe Ser Gly Arg Pro Arg Glu
1360            1365            1370            1375

GAT CGG GTG CCC CAC TCT CGG AAT TCC ATC ACC CTC ACC AAC CTC ACT        4177
Asp Arg Val Pro His Ser Arg Asn Ser Ile Thr Leu Thr Asn Leu Thr
        1380            1385            1390

CCA GGC ACA GAG TAT GTG GTC AGC ATC GTT GCT CTT AAT GGC AGA GAG        4225
Pro Gly Thr Glu Tyr Val Val Ser Ile Val Ala Leu Asn Gly Arg Glu
        1395            1400            1405

GAA AGT CCC TTA TTG ATT GGC CAA CAA TCA ACA GTT TCT GAT GTT CCG        4273
Glu Ser Pro Leu Leu Ile Gly Gln Gln Ser Thr Val Ser Asp Val Pro
        1410            1415            1420

AGG GAC CTG GAA GTT GTT GCT GCG ACC CCC ACC AGC CTA CTG ATC AGC        4321
Arg Asp Leu Glu Val Val Ala Ala Thr Pro Thr Ser Leu Leu Ile Ser
        1425            1430            1435

TGG GAT GCT CCT GCT GTC ACA GTG AGA TAT TAC AGG ATC ACT TAC GGA        4369
Trp Asp Ala Pro Ala Val Thr Val Arg Tyr Tyr Arg Ile Thr Tyr Gly
1440            1445            1450            1455

GAA ACA GGA GGA AAT AGC CCT GTC CAG GAG TTC ACT GTG CCT GGG AGC        4417
Glu Thr Gly Gly Asn Ser Pro Val Gln Glu Phe Thr Val Pro Gly Ser
        1460            1465            1470

AAG TCT ACA GCT ACC ATC AGC GGC CTT AAA CCT GGA GTT GAT TAT ACC        4465
Lys Ser Thr Ala Thr Ile Ser Gly Leu Lys Pro Gly Val Asp Tyr Thr
        1475            1480            1485

ATC ACT GTG TAT GCT GTC ACT GGC CGT GGA GAC AGC CCC GCA AGC AGC        4513
Ile Thr Val Tyr Ala Val Thr Gly Arg Gly Asp Ser Pro Ala Ser Ser
        1490            1495            1500

AAG CCA ATT TCC ATT AAT TAC CGA ACA GAA ATT GAC AAA CCA TCC CAG        4561
Lys Pro Ile Ser Ile Asn Tyr Arg Thr Glu Ile Asp Lys Pro Ser Gln
        1505            1510            1515

ATG CAA GTG ACC GAT GTT CAG GAC AAC AGC ATT AGT GTC AAG TGG CTG        4609
Met Gln Val Thr Asp Val Gln Asp Asn Ser Ile Ser Val Lys Trp Leu
1520            1525            1530            1535

CCT TCA AGT CCC CCT GTT ACT GGT TAC AGA GTA ACC ACC ACT CCC AAA        4657
Pro Ser Ser Ser Pro Val Thr Gly Tyr Arg Val Thr Thr Thr Pro Lys
        1540            1545            1550

AAT GGA CCA GGA CCA ACA AAA ACT AAA ACT GCA GGT CCA GAT CAA ACA        4705
Asn Gly Pro Gly Pro Thr Lys Thr Lys Thr Ala Gly Pro Asp Gln Thr
        1555            1560            1565

GAA ATG ACT ATT GAA GGC TTG CAG CCC ACA GTG GAG TAT GTG GTT AGT        4753
Glu Met Thr Ile Glu Gly Leu Gln Pro Thr Val Glu Tyr Val Val Ser
        1570            1575            1580

GTC TAT GCT CAG AAT CCA AGC GGA GAG AGT CAG CCT CTG GTT CAG ACT        4801
Val Tyr Ala Gln Asn Pro Ser Gly Glu Ser Gln Pro Leu Val Gln Thr
        1585            1590            1595

GCA GTA ACC AAC ATT GAT CGC CCT AAA GGA CTG GCA TTC ACT GAT GTG        4849
Ala Val Thr Asn Ile Asp Arg Pro Lys Gly Leu Ala Phe Thr Asp Val
1600            1605            1610            1615

GAT GTC GAT TCC ATC AAA ATT GCT TGG GAA AGC CCA CAG GGG CAA GTT        4897
Asp Val Asp Ser Ile Lys Ile Ala Trp Glu Ser Pro Gln Gly Gln Val
        1620            1625            1630

TCC AGG TAC AGG GTG ACC TAC TCG AGC CCT GAG GAT GGA ATC CAT GAG        4945
Ser Arg Tyr Arg Val Thr Tyr Ser Ser Pro Glu Asp Gly Ile His Glu
        1635            1640            1645
```

| | |
|---|---|
| CTA TTC CCT GCA CCT GAT GGT GAA GAA GAC ACT GCA GAG CTG CAA GGC<br>Leu Phe Pro Ala Pro Asp Gly Glu Glu Asp Thr Ala Glu Leu Gln Gly<br>          1650                   1655                   1660 | 4993 |
| CTC AGA CCG GGT TCT GAG TAC ACA GTC AGT GTG GTT GCC TTG CAC GAT<br>Leu Arg Pro Gly Ser Glu Tyr Thr Val Ser Val Val Ala Leu His Asp<br>       1665                   1670                   1675 | 5041 |
| GAT ATG GAG AGC CAG CCC CTG ATT GGA ACC CAG TCC ACA GCT ATT CCT<br>Asp Met Glu Ser Gln Pro Leu Ile Gly Thr Gln Ser Thr Ala Ile Pro<br>1680                   1685                   1690                   1695 | 5089 |
| GCA CCA ACT GAC CTG AAG TTC ACT CAG GTC ACA CCC ACA AGC CTG AGC<br>Ala Pro Thr Asp Leu Lys Phe Thr Gln Val Thr Pro Thr Ser Leu Ser<br>          1700                   1705                   1710 | 5137 |
| GCC CAG TGG ACA CCA CCC AAT GTT CAG CTC ACT GGA TAT CGA GTG CGG<br>Ala Gln Trp Thr Pro Pro Asn Val Gln Leu Thr Gly Tyr Arg Val Arg<br>               1715                   1720                   1725 | 5185 |
| GTG ACC CCC AAG GAG AAG ACC GGA CCA ATG AAA GAA ATC AAC CTT GCT<br>Val Thr Pro Lys Glu Lys Thr Gly Pro Met Lys Glu Ile Asn Leu Ala<br>      1730                   1735                   1740 | 5233 |
| CCT GAC AGC TCA TCC GTG GTT GTA TCA GGA CTT ATG GTG GCC ACC AAA<br>Pro Asp Ser Ser Ser Val Val Val Ser Gly Leu Met Val Ala Thr Lys<br>     1745                   1750                   1755 | 5281 |
| TAT GAA GTG AGT GTC TAT GCT CTT AAG GAC ACT TTG ACA AGC AGA CCA<br>Tyr Glu Val Ser Val Tyr Ala Leu Lys Asp Thr Leu Thr Ser Arg Pro<br>1760                   1765                   1770                   1775 | 5329 |
| GCT CAG GGT GTT GTC ACC ACT CTG GAG AAT GTC AGC CCA CCA AGA AGG<br>Ala Gln Gly Val Val Thr Thr Leu Glu Asn Val Ser Pro Pro Arg Arg<br>                  1780                   1785                   1790 | 5377 |
| GCT CGT GTG ACA GAT GCT ACT GAG ACC ACC ATC ACC ATT AGC TGG AGA<br>Ala Arg Val Thr Asp Ala Thr Glu Thr Thr Ile Thr Ile Ser Trp Arg<br>             1795                   1800                   1805 | 5425 |
| ACC AAG ACT GAG ACG ATC ACT GGC TTC CAA GTT GAT GCC GTT CCA GCC<br>Thr Lys Thr Glu Thr Ile Thr Gly Phe Gln Val Asp Ala Val Pro Ala<br>          1810                   1815                   1820 | 5473 |
| AAT GGC CAG ACT CCA ATC CAG AGA ACC ATC AAG CCA GAT GTC AGA AGC<br>Asn Gly Gln Thr Pro Ile Gln Arg Thr Ile Lys Pro Asp Val Arg Ser<br>         1825                   1830                   1835 | 5521 |
| TAC ACC ATC ACA GGT TTA CAA CCA GGC ACT GAC TAC AAG ATC TAC CTG<br>Tyr Thr Ile Thr Gly Leu Gln Pro Gly Thr Asp Tyr Lys Ile Tyr Leu<br>1840                   1845                   1850                   1855 | 5569 |
| TAC ACC TTG AAT GAC AAT GCT CGG AGC TCC CCT GTG GTC ATC GAC GCC<br>Tyr Thr Leu Asn Asp Asn Ala Arg Ser Ser Pro Val Val Ile Asp Ala<br>              1860                   1865                   1870 | 5617 |
| TCC ACT GCC ATT GAT GCA CCA TCC AAC CTG CGT TTC CTG GCC ACC ACA<br>Ser Thr Ala Ile Asp Ala Pro Ser Asn Leu Arg Phe Leu Ala Thr Thr<br>            1875                   1880                   1885 | 5665 |
| CCC AAT TCC TTG CTG GTA TCA TGG CAG CCG CCA CGT GCC AGG ATT ACC<br>Pro Asn Ser Leu Leu Val Ser Trp Gln Pro Pro Arg Ala Arg Ile Thr<br>       1890                   1895                   1900 | 5713 |
| GGC TAC ATC ATC AAG TAT GAG AAG CCT GGG TCT CCT CCC AGA GAA GTG<br>Gly Tyr Ile Ile Lys Tyr Glu Lys Pro Gly Ser Pro Pro Arg Glu Val<br>     1905                   1910                   1915 | 5761 |
| GTC CCT CGG CCC CGC CCT GGT GTC ACA GAG GCT ACT ATT ACT GGC CTG<br>Val Pro Arg Pro Arg Pro Gly Val Thr Glu Ala Thr Ile Thr Gly Leu<br>1920                   1925                   1930                   1935 | 5809 |
| GAA CCG GGA ACC GAA TAT ACA ATT TAT GTC ATT GCC CTG AAG AAT AAT<br>Glu Pro Gly Thr Glu Tyr Thr Ile Tyr Val Ile Ala Leu Lys Asn Asn<br>                1940                   1945                   1950 | 5857 |
| CAG AAG AGC GAG CCC CTG ATT GGA AGG AAA AAG ACA GAC GAG CTT CCC<br>Gln Lys Ser Glu Pro Leu Ile Gly Arg Lys Lys Thr Asp Glu Leu Pro<br>         1955                   1960                   1965 | 5905 |

```
CAA CTG GTA ACC CTT CCA CAC CCC AAT CTT CAT GGA CCA GAG ATC TTG        5953
Gln Leu Val Thr Leu Pro His Pro Asn Leu His Gly Pro Glu Ile Leu
        1970            1975            1980

GAT GTT CCT TCC ACA GTT CAA AAG ACC CCT TTC GTC ACC CAC CCT GGG        6001
Asp Val Pro Ser Thr Val Gln Lys Thr Pro Phe Val Thr His Pro Gly
    1985            1990            1995

TAT GAC ACT GGA AAT GGT ATT CAG CTT CCT GGC ACT TCT GGT CAG CAA        6049
Tyr Asp Thr Gly Asn Gly Ile Gln Leu Pro Gly Thr Ser Gly Gln Gln
2000            2005            2010            2015

CCC AGT GTT GGG CAA CAA ATG ATC TTT GAG GAA CAT GGT TTT AGG CGG        6097
Pro Ser Val Gly Gln Gln Met Ile Phe Glu Glu His Gly Phe Arg Arg
        2020            2025            2030

ACC ACA CCG CCC ACA ACG GCC ACC CCC ATA AGG CAT AGG CCA AGA CCA        6145
Thr Thr Pro Pro Thr Thr Ala Thr Pro Ile Arg His Arg Pro Arg Pro
            2035            2040            2045

TAC CCG CCG AAT GTA GGA CAA GAA GCT CTC TCT CAG ACA ACC ATC TCA        6193
Tyr Pro Pro Asn Val Gly Gln Glu Ala Leu Ser Gln Thr Thr Ile Ser
        2050            2055            2060

TGG GCC CCA TTC CAG GAC ACT TCT GAG TAC ATC ATT TCA TGT CAT CCT        6241
Trp Ala Pro Phe Gln Asp Thr Ser Glu Tyr Ile Ile Ser Cys His Pro
2065            2070            2075

GTT GGC ACT GAT GAA GAA CCC TTA CAG TTC AGG GTT CCT GGA ACT TCT        6289
Val Gly Thr Asp Glu Glu Pro Leu Gln Phe Arg Val Pro Gly Thr Ser
2080            2085            2090            2095

ACC AGT GCC ACT CTG ACA GGC CTC ACC AGA GGT GCC ACC TAC AAC ATC        6337
Thr Ser Ala Thr Leu Thr Gly Leu Thr Arg Gly Ala Thr Tyr Asn Ile
            2100            2105            2110

ATA GTG GAG GCA CTG AAA GAC CAG CAG AGG CAT AAG GTT CGG GAA GAG        6385
Ile Val Glu Ala Leu Lys Asp Gln Gln Arg His Lys Val Arg Glu Glu
        2115            2120            2125

GTT GTT ACC GTG GGC AAC TCT GTC AAC GAA GGC TTG AAC CAA CCT ACG        6433
Val Val Thr Val Gly Asn Ser Val Asn Glu Gly Leu Asn Gln Pro Thr
        2130            2135            2140

GAT GAC TCG TGC TTT GAC CCC TAC ACA GTT TCC CAT TAT GCC GTT GGA        6481
Asp Asp Ser Cys Phe Asp Pro Tyr Thr Val Ser His Tyr Ala Val Gly
    2145            2150            2155

GAT GAG TGG GAA CGA ATG TCT GAA TCA GGC TTT AAA CTG TTG TGC CAG        6529
Asp Glu Trp Glu Arg Met Ser Glu Ser Gly Phe Lys Leu Leu Cys Gln
2160            2165            2170            2175

TGC TTA GGC TTT GGA AGT GGT CAT TTC AGA TGT GAT TCA TCT AGA TGG        6577
Cys Leu Gly Phe Gly Ser Gly His Phe Arg Cys Asp Ser Ser Arg Trp
            2180            2185            2190

TGC CAT GAC AAT GGT GTG AAC TAC AAG ATT GGA GAG AAG TGG GAC CGT        6625
Cys His Asp Asn Gly Val Asn Tyr Lys Ile Gly Glu Lys Trp Asp Arg
        2195            2200            2205

CAG GGA GAA AAT GGC CAG ATG ATG AGC TGC ACA TGT CTT GGG AAC GGA        6673
Gln Gly Glu Asn Gly Gln Met Met Ser Cys Thr Cys Leu Gly Asn Gly
        2210            2215            2220

AAA GGA GAA TTC AAG TGT GAC CCT CAT GAG GCA ACG TGT TAC GAT GAT        6721
Lys Gly Glu Phe Lys Cys Asp Pro His Glu Ala Thr Cys Tyr Asp Asp
    2225            2230            2235

GGG AAG ACA TAC CAC GTA GGA GAA CAG TGG CAG AAG GAA TAT CTC GGT        6769
Gly Lys Thr Tyr His Val Gly Glu Gln Trp Gln Lys Glu Tyr Leu Gly
2240            2245            2250            2255

GCC ATT TGC TCC TGC ACA TGC TTT GGA GGC CAG CGG GGC TGG CGC TGT        6817
Ala Ile Cys Ser Cys Thr Cys Phe Gly Gly Gln Arg Gly Trp Arg Cys
            2260            2265            2270

GAC AAC TGC CGC AGA CCT GGG GGT GAA CCC AGT CCC GAA GGC ACT ACT        6865
Asp Asn Cys Arg Arg Pro Gly Gly Glu Pro Ser Pro Glu Gly Thr Thr
        2275            2280            2285
```

```
GGC CAG TCC TAC AAC CAG TAT TCT CAG AGA TAC CAT CAG AGA ACA AAC        6913
Gly Gln Ser Tyr Asn Gln Tyr Ser Gln Arg Tyr His Gln Arg Thr Asn
            2290            2295            2300

ACT AAT GTT AAT TGC CCA ATT GAG TGC TTC ATG CCT TTA GAT GTA CAG        6961
Thr Asn Val Asn Cys Pro Ile Glu Cys Phe Met Pro Leu Asp Val Gln
            2305            2310            2315

GCT GAC AGA GAA GAT TCC CGA GAG TAA ATC ATC TTT CCA ATC CAG AGG        7009
Ala Asp Arg Glu Asp Ser Arg Glu  *  Ile Ile Phe Pro Ile Gln Arg
2320            2325            2330            2335

AAC AAG CAT GTC TCT CTG CCA AGA TCC ATC TAA ACT GGA GTG ATG TTA        7057
Asn Lys His Val Ser Leu Pro Arg Ser Ile  *  Thr Gly Val Met Leu
                2340            2345            2350

GCA GAC CCA GCT TAG AGT TCT TCT TTC TTT CTT AAG CCC TTT GCT CTG        7105
Ala Asp Pro Ala  *  Ser Ser Ser Phe Phe Leu Lys Pro Phe Ala Leu
            2355            2360            2365

GAG GAA GTT CTC CAG CTT CAG CTC AAC TCA CAG CTT CTC CAA GCA TCA        7153
Glu Glu Val Leu Gln Leu Gln Leu Asn Ser Gln Leu Leu Gln Ala Ser
            2370            2375            2380

CCC TGG GAG TTT CCT GAG GGT TTT CTC ATA AAT GAG GGC TGC ACA TTG        7201
Pro Trp Glu Phe Pro Glu Gly Phe Leu Ile Asn Glu Gly Cys Thr Leu
    2385            2390            2395

CCT GTT CTG CTT CGA AGT ATT CAA TAC CGC TCA GTA TTT TAA ATG AAG        7249
Pro Val Leu Leu Arg Ser Ile Gln Tyr Arg Ser Val Phe  *  Met Lys
2400            2405            2410            2415

TGA TTC TAA GAT TTG GTT TGG GAT CAA TAG GAA AGC ATA TGC AGC CAA        7297
 *  Phe  *  Asp Leu Val Trp Asp Gln  *  Glu Ser Ile Cys Ser Gln
            2420            2425            2430

CCA AGA TGC AAA TGT TTT GAA ATG ATA TGA CCA AAA TTT TAA GTA GGA        7345
Pro Arg Cys Lys Cys Phe Glu Met Ile  *  Pro Lys Phe  *  Val Gly
            2435            2440            2445

AAG TCA CCC AAA CAC TTC TGC TTT CAC TTA AGT GTC TGG CCC GCA ATA        7393
Lys Ser Pro Lys His Phe Cys Phe His Leu Ser Val Trp Pro Ala Ile
            2450            2455            2460

CTG TAG GAA CAA GCA TGA TCT TGT TAC TGT GAT ATT TTA AAT ATC CAC        7441
Leu  *  Glu Gln Ala  *  Ser Cys Tyr Cys Asp Ile Leu Asn Ile His
    2465            2470            2475

AGT ACT CAC TTT TTC CAA ATG ATC CTA GTA ATT GCC TAG AAA TAT CTT        7489
Ser Thr His Phe Phe Gln Met Ile Leu Val Ile Ala  *  Lys Tyr Leu
2480            2485            2490            2495

TCT CTT ACC TGT TAT TTA TCA ATT TTT CCC AGT ATT TTT ATA CGG AAA        7537
Ser Leu Thr Cys Tyr Leu Ser Ile Phe Pro Ser Ile Phe Ile Arg Lys
            2500            2505            2510

AAA TTG TAT TGA AAA CAC TTA GTA TGC AGT TGA TAA GAG GAA TTT GGT        7585
Lys Leu Tyr  *  Lys His Leu Val Cys Ser  *   *  Glu Glu Phe Gly
            2515            2520            2525

ATA ATT ATG GTG GGT GAT TAT TTT TTA TAC TGT ATG TGC CAA AGC TTT        7633
Ile Ile Met Val Gly Asp Tyr Phe Leu Tyr Cys Met Cys Gln Ser Phe
            2530            2535            2540

ACT ACT GTG GAA AGA CAA CTG TTT TAA TAA AAG ATT TAC ATT CCA CAA        7681
Thr Thr Val Glu Arg Gln Leu Phe  *   *  Lys Ile Tyr Ile Pro Gln
            2545            2550            2555

AAAAAAAAAA AAAAAAAAAA AAAA                                             7705
```

( 2 ) INFORMATION FOR SEQ ID NO:17:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:17:

AATTCATATG CAGGCACAGC AAATGGTTCA GCCCCAGTCC CCGGTGGCTG TCAGTCAAAG    60

CAAGCCCGGT T    71

(2) INFORMATION FOR SEQ ID NO:18:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:18:

ATAACAACAA CCGGGCTTGC TTTGACTGAC AGCCACGGG GACTGGGGCT GAACCATTTG    60

CTGTGCCTGC ATATG    75

(2) INFORMATION FOR SEQ ID NO:19:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:19:

GTTATGACAA TGGAAAACAC TATCAGATAA ATCAACAGTG GGAGCGGACC TACCTAGGTG    60

AATGTGTTG    69

(2) INFORMATION FOR SEQ ID NO:20:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:20:

TTACCTAGGT AGGTCCGCTC CCACTGTTGA TTTATCTGAT AGTGTTTCC ATTGTC    56

(2) INFORMATION FOR SEQ ID NO:21:

(i) SEQUENCE CHARACTERISTICS:
        (A) LENGTH: 57 base pairs
        (B) TYPE: nucleic acid
        (C) STRANDEDNESS: single ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:21:

GTTTGTACTT GTTATGGAGG AAGCCGAGGT TTTAACTGCG AAAGTAAACC TGAAGCT    57

( 2 ) INFORMATION FOR SEQ ID NO:22:

( i ) SEQUENCE CHARACTERISTICS:
( A ) LENGTH: 70 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:22:

TCTCTTCAGC TTCAGGTTTA CTTTCGCAGT TAAAACCTGG CTTCCTCCAT AACAAGTACA    60

AACCAACACA    70

( 2 ) INFORMATION FOR SEQ ID NO:23:

( i ) SEQUENCE CHARACTERISTICS:
( A ) LENGTH: 69 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:23:

GAAGAGACTT GCTTTGACAA GTACACTGGG AACACTTACC GAGTGGGTGA CACTTATGAG    60

CGTCCTAAA    69

( 2 ) INFORMATION FOR SEQ ID NO:24:

( i ) SEQUENCE CHARACTERISTICS:
( A ) LENGTH: 58 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:24:

GACGCTCATA AGTGTCACCC ACTCGGTAAG TGTTCCCAGT GTACTTGTCA AAGCAAGG    58

( 2 ) INFORMATION FOR SEQ ID NO:25:

( i ) SEQUENCE CHARACTERISTICS:
( A ) LENGTH: 60 base pairs
( B ) TYPE: nucleic acid
( C ) STRANDEDNESS: single (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:25:

GACTCCATGA TCTGGGACTG TACCTGCATC GGGGCTGGGC GAGGGAGAAT AAGCTGTACC 60

(2) INFORMATION FOR SEQ ID NO:26:

(i) SEQUENCE CHARACTERISTICS:
  (A) LENGTH: 58 base pairs
  (B) TYPE: nucleic acid
  (C) STRANDEDNESS: single
  (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:26:

CTTATTCTCC CTCGCCCAGC CCCGATGCAG GTACAGTCCC AGATCATGGA GTCTTTAG 58

(2) INFORMATION FOR SEQ ID NO:27:

(i) SEQUENCE CHARACTERISTICS:
  (A) LENGTH: 71 base pairs
  (B) TYPE: nucleic acid
  (C) STRANDEDNESS: single
  (D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:27:

ATCGCCAACG CTGCCATGAA GGGGGTCAGT CCTACCAGAT TGGTGACACC TGGAGGAGAC 60

CACATGAGAC T 71

(2) INFORMATION FOR SEQ ID NO:28:

(i) SEQUENCE CHARACTERISTICS:
  (A) LENGTH: 85 base pairs
  (B) TYPE: nucleic acid
  (C) STRANDEDNESS: single
  (D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:28:

AACCACCAGT CTCATGTGGT CTCCTCCAGG TGTCACCAAT CTGGTAGGAC TGACCCCCTT 60

CATGGCAGCG TTTGCGATGG TACAG 85

(2) INFORMATION FOR SEQ ID NO:29:

(i) SEQUENCE CHARACTERISTICS:
  (A) LENGTH: 72 base pairs
  (B) TYPE: nucleic acid
  (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:29:

GGTGGTTACA TGTTAGAGTG TGTGTGTCTT GGTAATGGAA AAGGAGAATG GACCTGCAAG    60

CCCATAGCTG AG    72

(2) INFORMATION FOR SEQ ID NO:30:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:30:

GATCCTCAGC TATGGGCTTG CAGGTCCATT CTCCTTTTCC ATTACCAAGA CACACACACT    60

CTAACATGT    69

(2) INFORMATION FOR SEQ ID NO:31:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:31:

GGGCTGGGCG AGGGAGAATA AGCTGTACCA TCGCAAACCG CTAACAGCTG A    51

(2) INFORMATION FOR SEQ ID NO:32:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:32:

AGCTTCAGCT GTTAGCGGTT TGCGATGGTA CAGCTTATTC TCCCTCGCCC A    51

(2) INFORMATION FOR SEQ ID NO:33:

(i) SEQUENCE CHARACTERISTICS:
        (A) LENGTH: 51 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:33:

GGGCTGGGCG AGGGAGAATA AGCTGTACCA TCGCAAACCG CCATATGTAA A 51

(2) INFORMATION FOR SEQ ID NO:34:

(i) SEQUENCE CHARACTERISTICS:
(A) LENGTH: 51 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:34:

AGCTTTTACA TATGGCGGTT TGCGATGGTA CAGCTTATTC TCCCTCGCCC A 51

(2) INFORMATION FOR SEQ ID NO:35:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:35:

ATGGCCGTGG AGACAGCTAA CAGCTGA 27

(2) INFORMATION FOR SEQ ID NO:36:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:36:

AGCTTCAGCT GTTAGCTGTC TCCACGGCCA T 31

(2) INFORMATION FOR SEQ ID NO:37:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: cDNA -continued (i i i) HYPOTHETICAL: NO (i v) ANTI-SENSE: NO (x i) SEQUENCE DESCRIPTION: SEQ ID NO:37:

CTGTATACCA ACC    13

(2) INFORMATION FOR SEQ ID NO:38:

(i) SEQUENCE CHARACTERISTICS:
(A) LENGTH: 15 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: YES (x i) SEQUENCE DESCRIPTION: SEQ ID NO:38:

TAGGTTGGTA TACAG    15

(2) INFORMATION FOR SEQ ID NO:39:

(i) SEQUENCE CHARACTERISTICS:
(A) LENGTH: 33 base pairs
(B) TYPE: nucleic acid
(C) STRANDEDNESS: single
(D) TOPOLOGY: linear (i i) MOLECULE TYPE: cDNA (i i i) HYPOTHETICAL: NO (i v) ANTI-SENSE: NO (x i) SEQUENCE DESCRIPTION: SEQ ID NO:39:

GCCCATAGCT GAAAAGTAAT TTGATCATGC TGC    33